US008008327B2

(12) United States Patent
DiSalvo et al.

(10) Patent No.: US 8,008,327 B2
(45) Date of Patent: Aug. 30, 2011

(54) INDAZOLE COMPOUNDS AS CCR1 RECEPTOR ANTAGONISTS

(75) Inventors: Darren DiSalvo, New Milford, CT (US); Daniel Kuzmich, Danbury, CT (US); Can Mao, New Milford, CT (US); Hossein Razavi, Danbury, CT (US); Christopher Ronald Sarko, New Milford, CT (US); Alan David Swinamer, Woodbury, CT (US); David Smith Thomson, Ridgefield, CT (US); Qiang Zhang, Woodbury, CT (US)

(73) Assignee: Boehringer Ingelheim International GmbH, Ingelhem am Rhein (DE)

( * ) Notice: Subject to any disclaimer, the term of this patent is extended or adjusted under 35 U.S.C. 154(b) by 0 days.

(21) Appl. No.: 12/937,378

(22) PCT Filed: Apr. 23, 2009

(86) PCT No.: PCT/US2009/041485
§ 371 (c)(1),
(2), (4) Date: Oct. 12, 2010

(87) PCT Pub. No.: WO2009/134666
PCT Pub. Date: Nov. 5, 2009

(65) Prior Publication Data
US 2011/0034512 A1    Feb. 10, 2011

Related U.S. Application Data

(60) Provisional application No. 61/048,678, filed on Apr. 29, 2008.

(51) Int. Cl.
*A61K 31/416* (2006.01)
*A61K 31/4439* (2006.01)
*C07D 231/56* (2006.01)
*C07D 401/02* (2006.01)

(52) U.S. Cl. ........ 514/322; 514/338; 514/403; 546/200; 546/275.5; 548/362.5

(58) Field of Classification Search ................. None
See application file for complete search history.

(56) References Cited

U.S. PATENT DOCUMENTS

| | | | |
|---|---|---|---|
| 4,999,363 A | 3/1991 | Oshima et al. |
| 5,118,701 A | 6/1992 | Oshima et al. |
| 5,242,931 A | 9/1993 | Oshima et al. |
| 5,302,596 A | 4/1994 | Oshima et al. |
| 5,534,481 A | 7/1996 | Suzuki et al. |
| 5,612,360 A | 3/1997 | Boyd et al. |
| 5,616,537 A | 4/1997 | Yokota et al. |
| 5,670,452 A | 9/1997 | Suzuki et al. |
| 5,760,028 A | 6/1998 | Jadhav et al. |
| 5,763,616 A | 6/1998 | Suzuki et al. |
| 5,770,544 A | 6/1998 | Yokota et al. |
| 5,973,156 A | 10/1999 | Chambers et al. |
| 6,025,374 A | 2/2000 | Castro Pineiro et al. |
| 6,107,321 A | 8/2000 | Madin |
| 6,211,219 B1 | 4/2001 | MacLeod et al. |
| 6,326,382 B1 | 12/2001 | Villalobos et al. |
| 6,331,640 B1 | 12/2001 | Fotouhi et al. |
| 6,498,255 B2 | 12/2002 | Villalobos et al. |
| 6,716,978 B2 | 4/2004 | Marfat |
| 6,784,182 B2 | 8/2004 | Liebeschuetz et al. |
| 6,803,384 B2 | 10/2004 | Fotouhi et al. |
| 6,855,715 B1 | 2/2005 | Liebeschuetz et al. |
| 6,878,725 B2 | 4/2005 | Liebeschuetz et al. |
| 6,900,196 B2 | 5/2005 | Liebeschuetz et al. |
| 6,936,611 B2 | 8/2005 | Liebeschuetz et al. |
| 7,049,297 B2 | 5/2006 | Zhang et al. |
| 7,053,078 B2 | 5/2006 | Liebeschuetz et al. |
| 7,129,264 B2 | 10/2006 | Smallheer et al. |
| 7,223,782 B2 | 5/2007 | Atkinson et al. |
| 7,429,609 B2 | 9/2008 | Ohi et al. |
| 2002/0037860 A1 | 3/2002 | D'Andrea et al. |
| 2002/0052373 A1 | 5/2002 | Zorn et al. |
| 2004/0127536 A1 | 7/2004 | Bhagwat et al. |
| 2005/0009876 A1 | 1/2005 | Bhagwat et al. |
| 2005/0020564 A1 | 1/2005 | Atkinson et al. |
| 2005/0108582 A1 | 5/2005 | Fung |
| 2005/0208582 A1 | 9/2005 | Ohi et al. |
| 2005/0261339 A1 | 11/2005 | Ohi et al. |
| 2006/0252781 A1 | 11/2006 | Basarab et al. |
| 2006/0281739 A1 | 12/2006 | Gadek et al. |
| 2007/0004761 A1 | 1/2007 | Basarab et al. |
| 2008/0262040 A1 | 10/2008 | Callahan et al. |
| 2009/0054397 A1 | 2/2009 | Ohi et al. |
| 2010/0093724 A1 | 4/2010 | Cook et al. |
| 2011/0034512 A1 | 2/2011 | Disalvo et al. |
| 2011/0086846 A1 | 4/2011 | Cook et al. |

FOREIGN PATENT DOCUMENTS

EP     345747 A2    12/1989
(Continued)

OTHER PUBLICATIONS

Bruneau et al, caplus an 1990:478384.*
Kitamura, capus an 2008:94643.*
Doherty, caplus an 2009:583109.*
International Search Report for PCT/US2009/041485 mailed Jun. 29, 2009.
Alzheimer's Disease. Retrieved online Dec. 15, 2010. http:/www.cnn.com/HEALTH/mentalhealt/alzheimers.
Carter, P.H. et al., "N-aryl pyrazoles,indazoles and azaindazoles as antagonists of CC chemokine receptor 1: patent cooperation treaty applications WO2010036632, WO2009134666 and WO2009137337". Expert Opinion Ther. Patents, 2010, 20(11), p. 1-10.
Cheng, J-F, et al., "CCR1 Antagonists". Molecular Diversity, Kluwer Academic Publishers, vol. 12, No. 1, Jun. 17, 2008, p. 17-23.

*Primary Examiner* — Sun Jae Loewe
(74) *Attorney, Agent, or Firm* — Michael P. Morris; Anthony P. Bottino

(57) ABSTRACT

Disclosed indazoles compounds that are useful as antagonists of CCR1 activity and are thus useful for treating a variety of diseases and disorders that are mediated or sustained through the activity of CCR1 including autoimmune diseases, such as rheumatoid arthritis and multiple sclerosis. Also disclosed are pharmaceutical compositions comprising these compounds, methods of using these compounds in the treatment of various diseases and disorders, processes for preparing these compounds and intermediates useful in these processes.

7 Claims, No Drawings

FOREIGN PATENT DOCUMENTS

| | | | |
|---|---|---|---|
| EP | 1201268 | A2 | 5/2002 |
| JP | 10001478 | A | 1/1998 |
| WO | 9217475 | A1 | 10/1992 |
| WO | 9401415 | A1 | 1/1994 |
| WO | 9500509 | | 5/1995 |
| WO | 9617842 | A1 | 6/1996 |
| WO | 9711945 | A1 | 4/1997 |
| WO | 9719073 | A1 | 5/1997 |
| WO | 9723480 | A1 | 7/1997 |
| WO | 9803504 | A1 | 1/1998 |
| WO | 9923076 | A1 | 5/1999 |
| WO | 0021920 | A1 | 4/2000 |
| WO | 0076970 | A2 | 12/2000 |
| WO | 0076971 | A2 | 12/2000 |
| WO | 0100656 | A2 | 1/2001 |
| WO | 0210137 | A2 | 2/2002 |
| WO | 03087085 | A1 | 10/2003 |
| WO | 03101968 | A1 | 12/2003 |
| WO | 03105853 | A1 | 12/2003 |
| WO | 2004043924 | A1 | 5/2004 |
| WO | 2004056831 | A1 | 7/2004 |
| WO | 2004094372 | A2 | 11/2004 |
| WO | 2005016929 | A1 | 2/2005 |
| WO | 2006091496 | A2 | 8/2006 |
| WO | 2006125119 | A1 | 11/2006 |
| WO | 2007002293 | A2 | 1/2007 |
| WO | 2007028083 | A2 | 3/2007 |
| WO | 2007102883 | A2 | 9/2007 |
| WO | 2008011131 | | 1/2008 |
| WO | 2009024585 | A2 | 2/2009 |
| WO | 2009037570 | A2 | 3/2009 |
| WO | 2009134666 | A1 | 11/2009 |
| WO | 2009137338 | A1 | 11/2009 |
| WO | 2010036632 | A1 | 4/2010 |

* cited by examiner

INDAZOLE COMPOUNDS AS CCR1 RECEPTOR ANTAGONISTS

FIELD OF THE INVENTION

This invention relates to indazoles that are useful as antagonists of CCR1 activity and are thus useful for treating a variety of diseases and disorders that are mediated or sustained through the activity of CCR1 including autoimmune diseases, such as rheumatoid arthritis and multiple sclerosis. This invention also relates to pharmaceutical compositions comprising these compounds, methods of using these compounds in the treatment of various diseases and disorders, processes for preparing these compounds and intermediates useful in these processes.

BACKGROUND OF THE INVENTION

Chemotactic Cytokine Receptor 1 (CCR1) belongs to a large family (>20) of chemotactic cytokine (chemokine) receptors that interact with specific chemokines (>50) to mediate leukocyte trafficking, granule exocytosis, gene transcription, mitogenic effects and apoptosis. Chemokines are best known for their ability to mediate basal and inflammatory leukocyte trafficking. The binding of at least three chemokines (MIP-1 alpha/CCL3, MCP3/CCL7 and RANTES/CCL5) to CCR1 is responsible for the trafficking of monocytes, macrophages and TH1 cells to inflamed tissues of rheumatoid arthritis (RA) and multiple sclerosis (MS) patients (Trebst et al. (2001) American J of Pathology 159 p. 1701). Macrophage inflammatory protein 1 alpha (MIP-1 alpha), macrophage chemoattractant protein 3 (MCP-3) and regulated on activation, normal T-cell expressed and secreted (RANTES) are all found in the CNS of MS patients, while MIP-1 alpha and RANTES are found in the CNS in the experimental autoimmune encephalomyelitis (EAE) model of MS (Review: Gerard and Rollins (2001) Nature Immunology). Macrophages and Th1 cells in the inflamed synovia of RA patients are also major producers of MIP-1 alpha and RANTES, which continuously recruit leukocytes to the synovial tissues of RA patients to propagate chronic inflammation (Volin et al. (1998) Clin. Immunol. Immunopathology; Koch et al. (1994) J. Clin. Investigation; Conlon et al. (1995) Eur. J. Immunology). Antagonizing the interactions between CCR1 and its chemokine ligands is hypothesized to block chemotaxis of monocytes, macrophages and Th1 cells to inflamed tissues and thereby ameliorate the chronic inflammation associated with autoimmune diseases such as RA and MS.

Evidence for the role of CCR1 in the development and progression of chronic inflammation associated with experimental autoimmune encephalitis (EAE), a model of multiple sclerosis, is based on both genetic deletion and small molecule antagonists of CCR1. CCR1 deficient mice were shown to exhibit reduced susceptibility (55% vs. 100%) and reduced severity (1.2 vs. 2.5) of active EAE (Rottman et al. (2000) Eur. J. Immunology). Furthermore, administration of small molecule antagonist of CCR1, with moderate affinity ($K_i$=120 nM) for rat CCR1, was shown to delay the onset and reduce the severity of EAE when administered intravenously (Liang et al. (2000) J. Biol. Chemistry). Treatment of mice with antibodies specific for the CCR1 ligand MIP-1 alpha have also been shown to be effective in preventing development of acute and relapsing EAE by reducing the numbers of T cells and macrophages recruited to the CNS (Karpus et al. (1995) J. Immunology; Karpus and Kennedy (1997) J. Leukocyte Biology). Thus, at least one CCR1 ligand has been demonstrated to recruit leukocytes to the CNS and propagate chronic inflammation in EAE, providing further in vivo validation for the role of CCR1 in EAE and MS.

In vivo validation of CCR1 in the development and propagation of chronic inflammation associated with RA is also significant. For example, administration of a CCR1 antagonist in the collagen induced arthritis model (CIA) in DBA/1 mice has been shown to be effective in reducing synovial inflammation and joint destruction (Plater-Zyberk et al. (1997) Immunology Letters). Another recent publication described potent antagonists of murine CCR1 that reduced severity (58%) in LPS-accelerated collagen-induced arthritis (CIA), when administered orally (Biorganic and Medicinal Chemistry Letters (15 (2005) 5160-5164). Published results from a Phase I clinical trial with an oral CCR1 antagonist demonstrated a trend toward clinical improvement in the absence of adverse side effects (Haringman et al. (2003) Ann. Rheum. Dis.). One third of the patients achieved a 20% improvement in rheumatoid arthritis signs and symptoms (ACR20) on day 18 and CCR1 positive cells were reduced by 70% in the synovia of the treated patients, with significant reduction in specific cell types including 50% reduction in $CD4^+$ T cells, 50% reduction in $CD8^+$ T cells and 34% reduction in macrophages.

Studies such as those cited above support a role for CCR1 in MS and RA and provide a therapeutic rationale for the development of CCR1 antagonists.

BRIEF SUMMARY OF THE INVENTION

The present invention provides novel compounds which block the interaction of CCR1 and its ligands and are thus useful for treating a variety of diseases and disorders that are mediated or sustained through the activity of CCR1 including autoimmune diseases, such as rheumatoid arthritis and multiple sclerosis. This invention also relates to pharmaceutical compositions comprising these compounds, methods of using these compounds in the treatment of various diseases and disorders, processes for preparing these compounds and intermediates useful in these processes.

DETAILED DESCRIPTION OF THE INVENTION

In its broadest generic aspect the invention provides compounds of the formula (I)

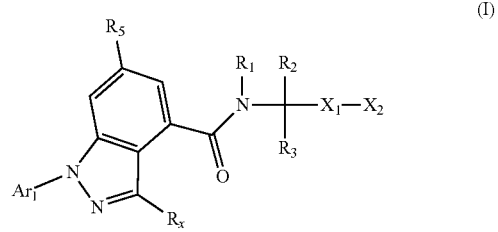

wherein
$Ar_1$ is carbocycle, heteroaryl or heterocycle each optionally substituted by one to three $R_a$;
$X_1$ is a —$(CH_2)_n$— wherein one or more hydrogen atoms can be replaced by $R_a$;
$X_2$ is $Ar_2$, —$S(O)_m$—$Ar_2$, —$S(O)_m NR_e R_f$ or —$S(O)_m NH$—$Ar_2$,
$Ar_2$ is carbocycle, heteroaryl or heterocycle each optionally substituted by one to three $R_b$;

$R_1$ is hydrogen, $C_{1-6}$ alkyl or $C_{1-6}$alkoxy$C_{1-6}$alkyl;

$R_2$, $R_3$ are each independently hydrogen or $C_{1-6}$ alkyl optionally substituted by $R_a$;

$R_a$ is $C_{1-6}$ alkyl, $C_{3-10}$cycloalkyl, $C_{1-6}$ alkoxy, $C_{1-6}$ alkylthio, $C_{1-6}$ alkylsulfonyl, $C_{1-6}$ alkoxycarbonyl, amino, mono- or di-$C_{1-6}$ alkylamino, $C_{3-6}$ cycloalkylamino, $C_{1-6}$ alkylaminocarbonyl, $C_{1-6}$ acyl, $C_{1-6}$ acylamino, $C_{1-6}$ dialkylaminocarbonyl, hydroxyl, halogen, cyano, nitro, oxo, $R_4$—S$(O)_m$—NH—, $R_4$—NH—S$(O)_m$—, aryl or carboxyl;

$R_b$ is hydroxyl, carboxyl, halogen, —(CH$_2)_n$—CN, nitro, oxo, $C_{1-6}$ alkyl, $C_{2-6}$ alkenyl, $C_{2-6}$ alkynyl, $C_{3-10}$cycloalkyl, $C_{1-6}$ alkoxy, $C_{1-6}$ alkoxycarbonyl, —(CH$_2)_n$—NR$_c$R$_d$, $R_4$—S$(O)_m$—, $R_4$—S$(O)_m$—NR$_e$—, $R_4$—NR$_e$—S$(O)_m$—, —NR$_f$—C(O)—R$_e$, —(CH$_2)_x$—C(O)—(CH$_2)_n$—NR$_c$R$_d$, heterocyclyl, aryl or heteroaryl, each substituent on $R_b$ where possible is optionally halogenated or substituted with 1 to 3 $C_{1-6}$ alkyl, $C_{1-6}$ acyl, $C_{1-6}$ alkoxycarbonyl, $C_{1-6}$ alkyl-S$(O)_m$—, aryl or carboxyl;

each $R_c$, $R_d$ are independently hydrogen, $C_{1-6}$ alkyl, $C_{1-6}$ acyl, $C_{3-10}$cycloalkyl, $C_{1-6}$ alkoxy, hydroxy$C_{1-6}$ alkyl, $C_{1-6}$ alkyl$C_{1-6}$ alkoxy, $C_{1-6}$ alkylsulfonyl, $C_{1-6}$ alkoxycarbonyl or —(CH$_2)_n$—NR$_e$R$_f$;

each $R_e$, $R_f$ are independently hydrogen, $C_{1-6}$ alkyl, $C_{3-10}$cycloalkyl, $C_{1-6}$ alkoxy, hydroxy$C_{1-6}$ alkyl or $C_{1-6}$ acyl;

$R_4$ is hydrogen, $C_{1-6}$ alkyl, heterocyclyl, aryl or heteroaryl each optionally substituted with $C_{1-6}$ alkyl, $C_{1-6}$ alkoxy, halogen, hydroxyl, amino, mono- or di-$C_{1-6}$ alkylamino, $C_{1-6}$ alkoxycarbonyl, $C_{1-6}$ acylamino;

$R_5$ is hydrogen or $R_a$;

$R_x$ is hydrogen or halogen;

each n, x are independently 0-3;

each m is independently 0-2;

or the pharmaceutically acceptable salts thereof.

The compound as described in the embodiment immediately above and wherein

Ar$_1$ is aryl, thienyl, furanyl, pyranyl, oxazolyl, isoxazolyl, thiazolyl, pyrazolyl, pyrrolyl, imidazolyl, thiadiazolyl, pyridinyl, pyrimidinyl, pyridazinyl, pyrazinyl or triazinyl each optionally substituted by one to three $R_a$;

X$_1$ is a —(CH$_2)_n$—;

Ar$_2$ is aryl, furanyl, pyranyl, benzoxazolyl, benzothiazolyl, benzimidazolyl, benzimidazolonyl, tetrahydropyranyl, dioxanyl, tetrahydrofuranyl, oxazolyl, isoxazolyl, thiazolyl, pyrazolyl, pyrrolyl, imidazolyl, thienyl, thiadiazolyl, thiomorpholinyl, 1,1-dioxo-1$\lambda^6$-thiomorpholinyl, morpholinyl, pyridinyl, pyridinonyl, pyrimidinyl, pyridazinyl, pyrazinyl, triazinyl, pyrrolidinyl, piperidinyl, piperazinyl, purinyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl or benzodioxolyl each optionally substituted by one to three $R_b$;

$R_1$ is hydrogen or $C_{1-4}$ alkyl;

$R_2$, $R_3$ are each independently hydrogen or $C_{1-3}$ alkyl;

$R_a$ is $C_{1-5}$ alkyl, $C_{3-7}$ cycloalkyl, $C_{1-5}$ alkoxy, $C_{1-5}$ alkoxycarbonyl, amino, $C_{1-5}$ acyl, $C_{1-5}$ acylamino, halogen, cyano, nitro, hydroxyl, $C_{1-5}$ alkyl-S$(O)_m$—NH—, $C_{1-5}$ alkyl-NH—S$(O)_m$— or carboxyl;

$R_b$ is hydroxyl, carboxyl, halogen, cyano, —CH$_2$—CN, $C_{1-5}$ alkyl, $C_{2-5}$ alkynyl, $C_{3-7}$ cycloalkyl, $C_{1-5}$ alkoxy, $C_{1-5}$ alkoxycarbonyl, —(CH$_2)_n$—NR$_c$R$_d$, $R_4$—S$(O)_m$—, $R_4$—S$(O)_m$—NR$_e$—, $R_4$—NR$_e$—S$(O)_m$—, —NR$_f$—C(O)—R$_e$, —(CH$_2)_x$—C(O)—(CH$_2)_n$—NR$_c$R$_d$, phenyl, pyrazolyl, pyrrolyl, imidazolyl, thiadiazolyl, pyridinyl, pyridinonyl, pyrimidinyl, pyridazinyl, pyrazinyl, pyrrolidinyl, piperidinyl or piperazinyl, each substituent on $R_b$ where possible is optionally halogenated or substituted with 1 to 3 $C_{1-6}$ alkyl, $C_{1-6}$ acyl, $C_{1-6}$ alkoxycarbonyl, $C_{1-6}$ alkyl-S$(O)_m$—, phenyl, naphthyl or carboxyl;

$R_4$ is hydrogen, $C_{1-5}$ alkyl, phenyl, naphthyl, oxazolyl, isoxazolyl, thiazolyl, pyrazolyl, pyrrolyl, imidazolyl, thienyl, thiadiazolyl, thiomorpholinyl, 1,1-dioxo-1$\lambda^6$-thiomorpholinyl, morpholinyl, pyridinyl, pyridinonyl, pyrimidinyl, pyridazinyl, pyrazinyl, triazinyl, pyrrolidinyl, piperidinyl, piperazinyl or tetrahydropyranyl, each optionally substituted with halogen, hydroxyl, $C_{1-5}$alkyl, $C_{1-5}$ alkoxy, amino, mono- or di-$C_{1-5}$ alkylamino, $C_{1-5}$ alkoxycarbonyl, $C_{1-5}$ acylamino;

$R_x$ is hydrogen.

The compound as described in the embodiment immediately above and wherein

Ar$_1$ is phenyl, naphthyl, thienyl, furanyl, pyranyl, oxazolyl, isoxazolyl, thiazolyl, thiadiazolyl, pyridinyl, pyrimidinyl, pyridazinyl or pyrazinyl each optionally substituted by one to three $R_a$;

Ar$_2$ is phenyl, naphthyl, benzimidazolyl, benzimidazolonyl, thiomorpholinyl, 1,1-dioxo-1$\lambda^6$-thiomorpholinyl, morpholinyl, pyridinyl, pyridinonyl, pyrimidinyl, pyridazinyl, pyrazinyl, piperidinyl, piperazinyl, indolyl, isoindolyl, benzofuranyl or benzopyranyl each optionally substituted by one to three $R_b$;

$R_1$ is hydrogen or $C_{1-3}$ alkyl;

$R_2$, $R_3$ are each independently hydrogen or $C_{1-3}$ alkyl;

$R_a$ is $C_{1-5}$ alkyl, $C_{3-6}$ cycloalkyl, $C_{1-5}$ alkoxy, $C_{1-5}$ alkoxycarbonyl, halogen, cyano, hydroxyl, $C_{1-5}$ alkyl-S$(O)_m$—NH—, $C_{1-5}$ alkyl-NH—S$(O)_m$— or carboxyl;

$R_b$ is hydroxyl, carboxyl, halogen, cyano, —CH$_2$—CN, $C_{1-5}$ alkyl, $C_{2-4}$ alkynyl, $C_{3-7}$ cycloalkyl, $C_{1-5}$ alkoxy, $C_{1-5}$ alkoxycarbonyl, —(CH$_2)_n$—NR$_c$R$_d$, $R_4$—S$(O)_m$—, $R_4$—S$(O)_m$—NR$_e$—, $R_4$—NR$_e$—S$(O)_m$—, —NR$_f$—C(O)—R$_e$, —(CH$_2)_x$—C(O)—(CH$_2)_n$—NR$_c$R$_d$, phenyl, pyrazolyl, pyrrolyl, imidazolyl, thiadiazolyl, pyridinyl, pyridinonyl, pyrimidinyl, pyridazinyl, pyrazinyl, pyrrolidinyl, piperidinyl or piperazinyl, each substituent on $R_b$ where possible is optionally halogenated or substituted with 1 to 3 $C_{1-6}$ alkyl, $C_{1-6}$ acyl, $C_{1-6}$ alkoxycarbonyl, $C_{1-6}$ alkyl-S$(O)_m$—, phenyl, naphthyl or carboxyl;

each $R_c$, $R_d$ are independently hydrogen, $C_{1-6}$ alkyl, $C_{1-6}$ acyl, $C_{3-10}$ cycloalkyl, $C_{1-6}$ alkoxy, hydroxy$C_{1-6}$ alkyl, $C_{1-6}$ alkyl$C_{1-6}$ alkoxy, $C_{1-6}$ alkylsulfonyl, $C_{1-6}$ alkoxycarbonyl or —(CH$_2)_n$—NR$_e$R$_f$;

each $R_e$, $R_f$ are independently hydrogen, $C_{1-6}$ alkyl, $C_{3-10}$ cycloalkyl, $C_{1-6}$ alkoxy, hydroxy$C_{1-6}$ alkyl or $C_{1-6}$ acyl;

$R_4$ is hydrogen, $C_{1-5}$ alkyl, phenyl, naphthyl, oxazolyl, isoxazolyl, thiazolyl, pyrazolyl, pyrrolyl, imidazolyl, thienyl, thiadiazolyl, thiomorpholinyl, 1,1-dioxo-1$\lambda^6$-thiomorpholinyl, morpholinyl, pyridinyl, pyridinonyl, pyrimidinyl, pyridazinyl, pyrazinyl, triazinyl, pyrrolidinyl, piperidinyl or piperazinyl, each optionally substituted with halogen, hydroxyl, $C_{1-5}$ alkoxy, amino, mono- or di-$C_{1-5}$ alkylamino, $C_{1-5}$ alkoxycarbonyl, $C_{1-5}$ acylamino;

$R_5$ is hydrogen, CN, methyl, —S(O)$_2$—CH$_3$.

The compound as described in the embodiment immediately above and wherein

Ar$_1$ is phenyl, naphthyl, thienyl, furanyl, pyranyl, oxazolyl, isoxazolyl, thiazolyl, thiadiazolyl, pyridinyl, pyrimidinyl, pyridazinyl or pyrazinyl each optionally substituted by one to three $R_a$;

X$_1$ is a —(CH$_2)_n$—;

X$_2$ is Ar$_2$;

Ar$_2$ is phenyl, naphthyl, benzimidazolyl, benzimidazolonyl, morpholinyl, pyridinyl, pyridinonyl, each optionally substituted by one to two $R_b$;

$R_1$ is hydrogen or $C_{1-3}$ alkyl;

$R_2$, $R_3$ are each independently hydrogen or $C_{1-3}$ alkyl;

$R_a$ is $C_{1-5}$ alkyl, $C_{3-6}$ cycloalkyl, $C_{1-5}$ alkoxy, $C_{1-5}$ alkoxycarbonyl, halogen, cyano, hydroxyl, $C_{1-5}$ alkyl-S(O)$_m$—NH—, $C_{1-5}$ alkyl-NH—S(O)$_m$— or carboxyl;

$R_b$ is carboxyl, halogen, cyano, —CH$_2$—CN, $C_{1-4}$ alkyl, CF$_3$, $C_{1-4}$ alkoxy, $C_{1-4}$ alkoxycarbonyl, ethynyl, phenyl, imidazolyl, piperidinyl, piperazinyl, or $R_b$ is NH$_2$—S(O)$_2$—,
NH$_2$—C(O)—CH$_2$—,
—N(C$_{1-3}$ alkyl)$_2$,
—N(C$_{1-3}$ alkyl)$_2$C(O)—C$_{1-3}$ alkyl,
—C(O)NH—C$_{1-3}$ alkyl,
—C(O)N(C$_{1-3}$ alkyl)$_2$,
—C(O)NH—(CH$_2$)$_{1-2}$—O—C$_{1-3}$alkyl,
—C(O)NH$_2$,
—S(O)$_2$—C$_{1-3}$ alkyl,
—S(O)$_2$—(CH$_2$)$_{1-2}$—C(O)—O—C$_{1-3}$alkyl,
—S(O)$_2$—NH—C$_{1-3}$ alkyl,
—S(O)$_2$—N(C$_{1-3}$ alkyl)$_2$,
—CH$_2$—S(O)$_2$—N(C$_{1-3}$ alkyl)$_2$,
—S(O)$_2$NH—(CH$_2$)$_{1-2}$—O—C$_{1-3}$alkyl,
—S(O)$_2$NH—(CH$_2$)$_{1-2}$—N(C$_{1-3}$alkyl)$_2$,
—S(O)$_2$NH—(CH$_2$)$_{1-2}$—OH,
—S(O)$_2$NH—(CH$_2$)$_{1-2}$—NHC(O)C$_{1-3}$alkyl),
—S(O)$_2$NH-(tetrahydropyran-4-yl),
—S(O)$_2$NR$_e$(1-C$_{1-3}$alkylpiperidin-4-yl),
—S(O)$_2$NH-(4-C$_{1-3}$alkylpiperazin-1-yl),
—S(O)$_2$NH-(4-diC$_{1-3}$alkylaminopiperidin-4-yl),
—S(O)$_2$-morpholinyl,
—C(O)—O—C$_{1-3}$alkyl,
—CH$_2$—C(O)—O—C$_{1-3}$alkyl,
—SCF$_3$ or
—SCH$_3$.

The compound as described in the embodiment immediately above and wherein

Ar$_1$ is

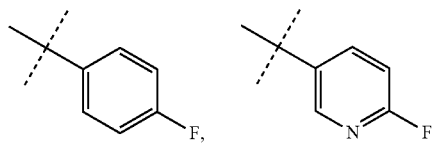

and the combination of

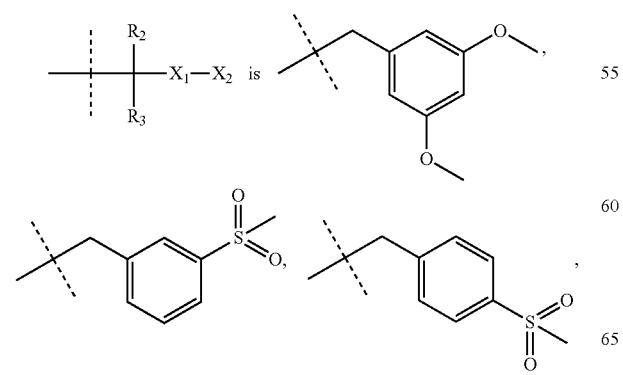

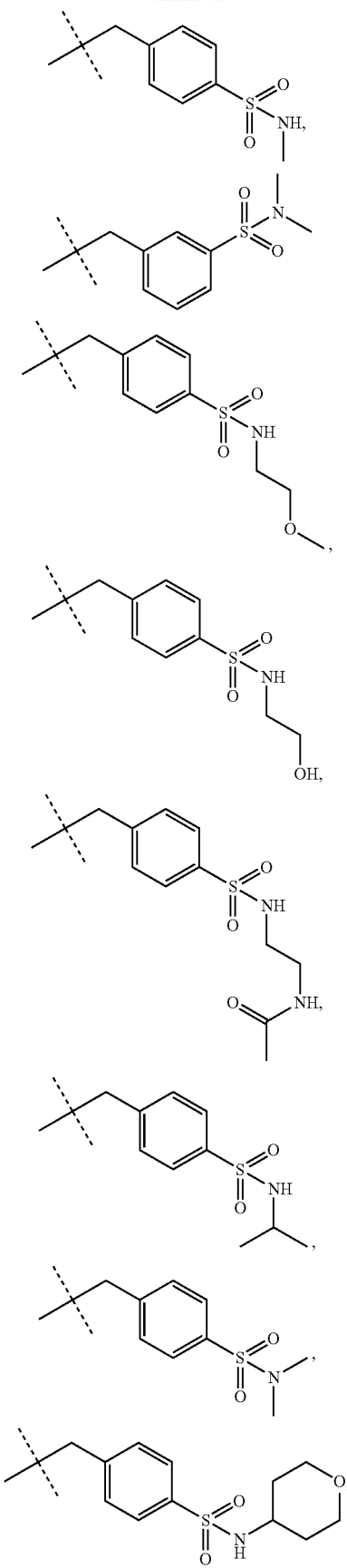

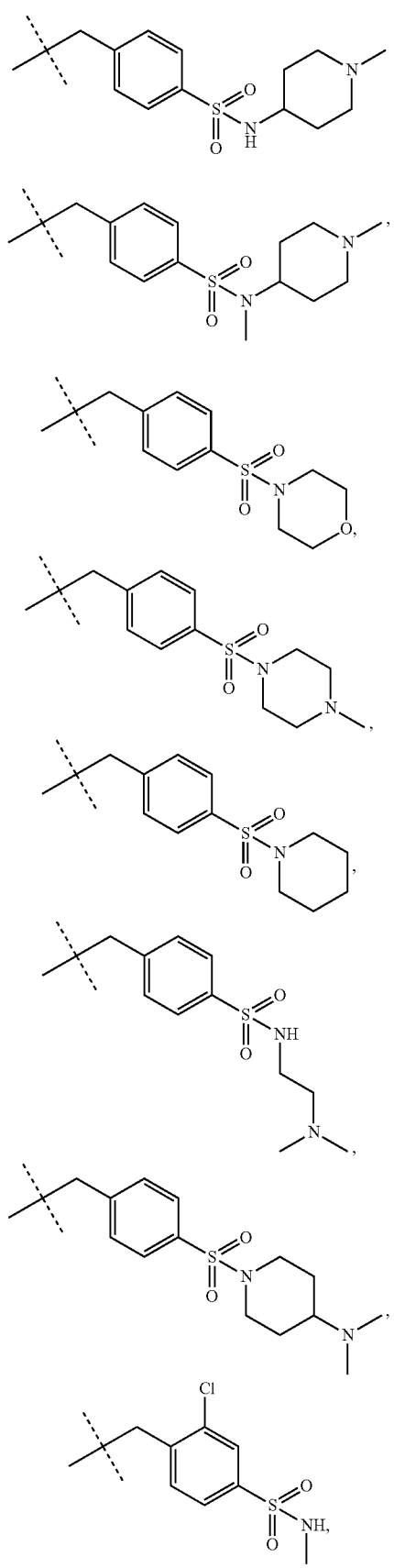
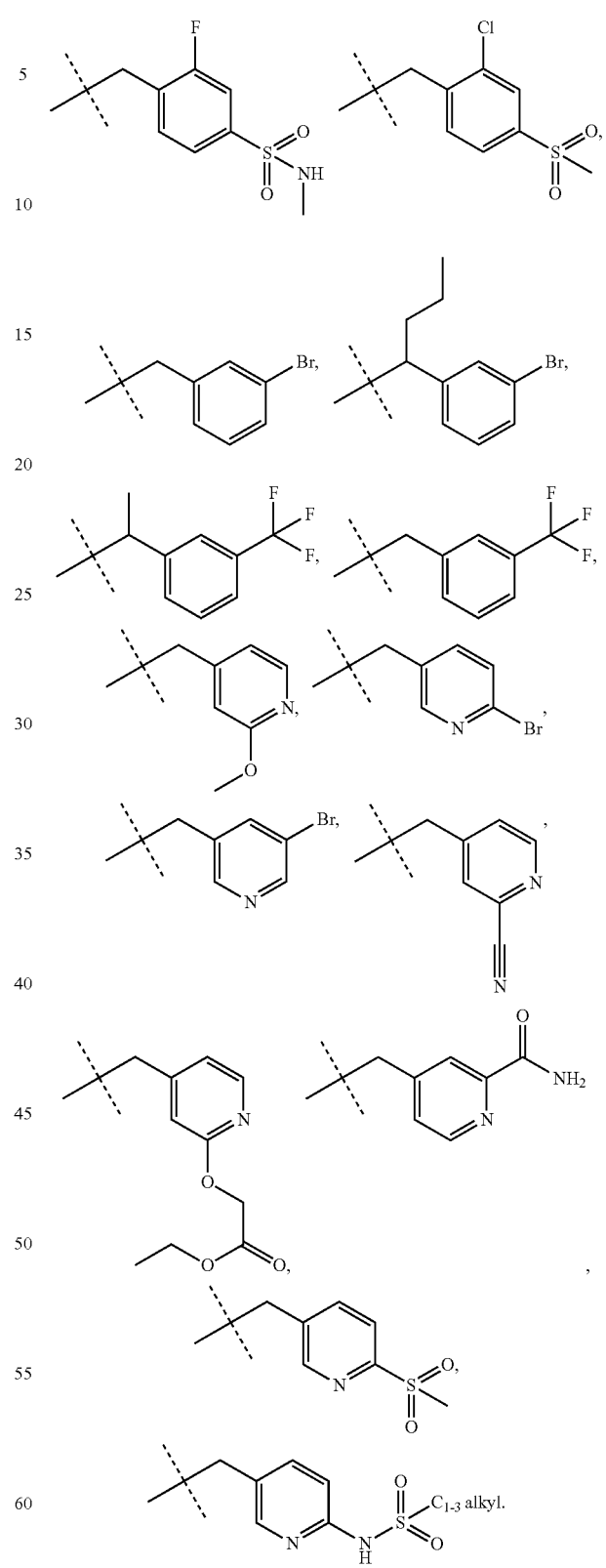
The following are representative compounds of the invention which can be made by the general synthetic schemes, the examples, and known methods in the art.

TABLE I

| STRUCTURE | Name | Observed [M + H]+ |
|---|---|---|
| 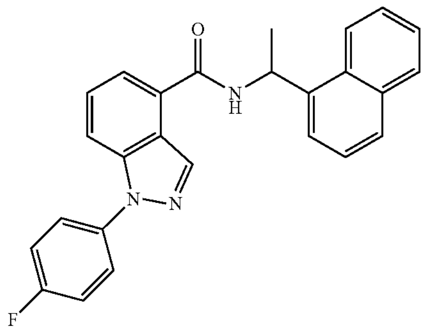 | 1-(4-Fluoro-phenyl)-1H-indazole-4-carboxylic acid (1-naphthalen-1-yl-ethyl)-amide | 410.2 |
| 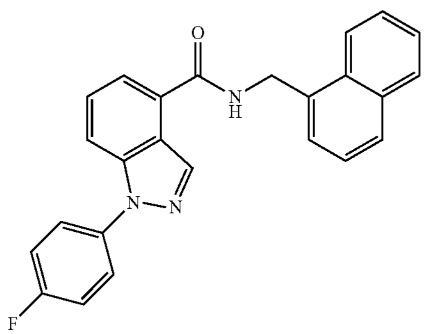 | 1-(4-Fluoro-phenyl)-1H-indazole 4-carboxylic acid (naphthalen-1-ylmethyl)-amide | 396.1 |
| 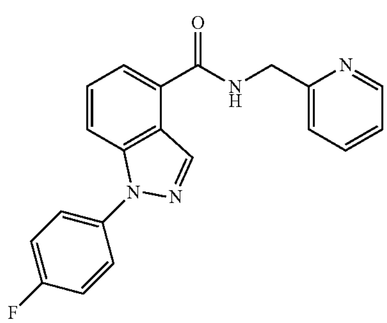 | 1-(4-Fluoro-phenyl)-1H-indazole-4-carboxylic acid (pyridin-2-ylmethyl)-amide | 347.1 |
| 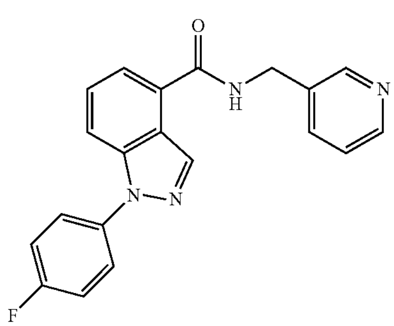 | 1-(4-Fluoro-phenyl)-1H-indazole-4-carboxylic acid (pyridin-3-ylmethyl)-amide | 347.1 |

TABLE I-continued

| STRUCTURE | Name | Observed [M + H]+ |
|---|---|---|
| 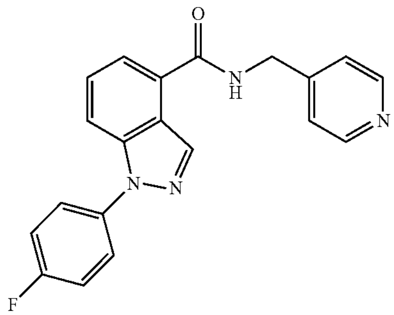 | 1-(4-Fluoro-phenyl)-1H-indazole-4-carboxylic acid (pyridin-4-ylmethyl)-amide | 347.1 |
| 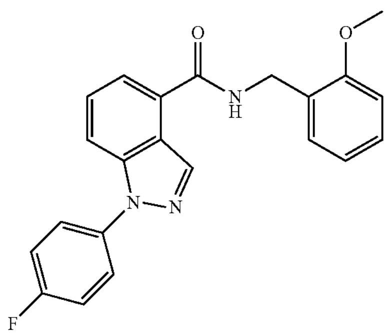 | 1-(4-Fluoro-phenyl)-1H-indazole-4-carboxylic acid 2-methoxy-benzylamide | 376.1 |
| 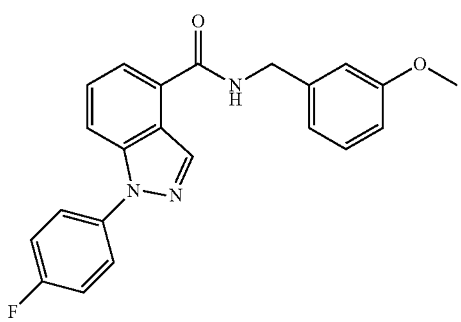 | 1-(4-Fluoro-phenyl)-1H-indazole-4-carboxylic acid 3-methoxy-benzylamide | 376.1 |
| 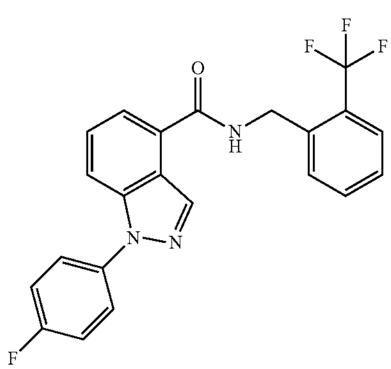 | 1-(4-Fluoro-phenyl)-1H-indazole-4-carboxylic acid 2-trifluoromethyl-benzylamide | 414.1 |

TABLE I-continued

| STRUCTURE | Name | Observed [M + H]+ |
|---|---|---|
| 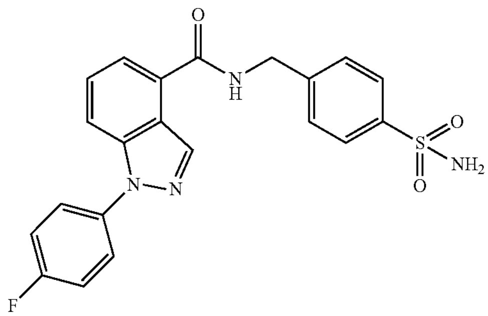 | 1-(4-Fluoro-phenyl)-1H-indazole-4-carboxylic acid 4-sulfamoyl-benzylamide | 425.2 |
| 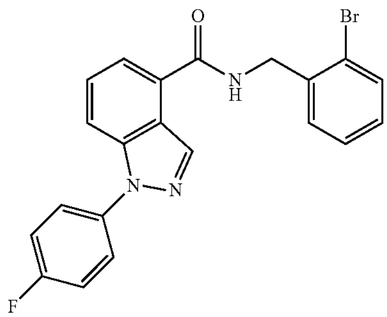 | 1-(4-Fluoro-phenyl)-1H-indazole-4-carboxylic acid 2-bromo-benzylamide | 425.0 |
| 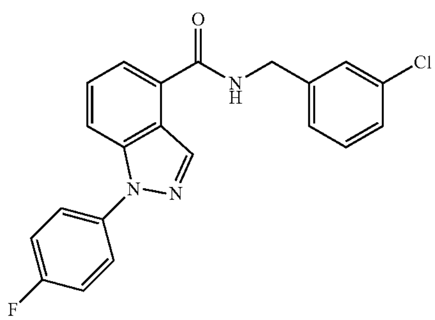 | 1-(4-Fluoro-phenyl)-1H-indazole-4-carboxylic acid 3-chloro-benzylamide | 380.5 |
| 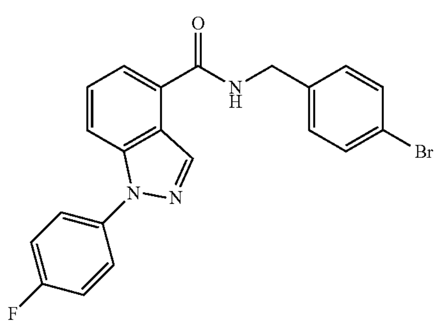 | 1-(4-Fluoro-phenyl)-1H-indazole-4-carboxylic acid 4-bromo-benzylamide | 425.0 |
| 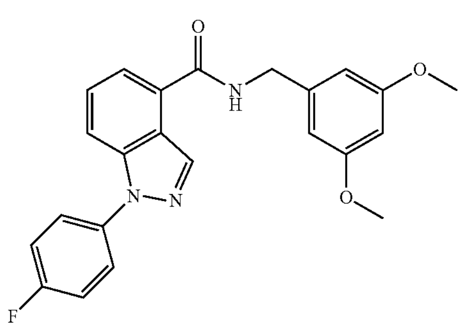 | 1-(4-Fluoro-phenyl)-1H-indazole-4-carboxylic acid 3,5-dimethoxy-benzylamide | 406.1 |

TABLE I-continued

| STRUCTURE | Name | Observed [M + H]+ |
|---|---|---|
| 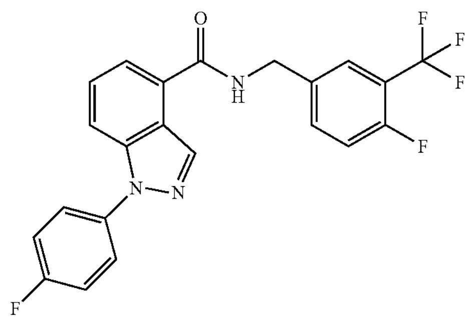 | 1-(4-Fluoro-phenyl)-1H-indazole-4-carboxylic acid 4-fluoro-3-trifluoromethyl-benzylamide | 432.1 |
| 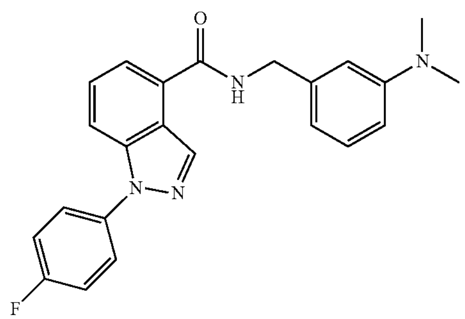 | 1-(4-Fluoro-phenyl)-1H-indazole-4-carboxylic acid 3-dimethylamino-benzylamide | 389.1 |
| 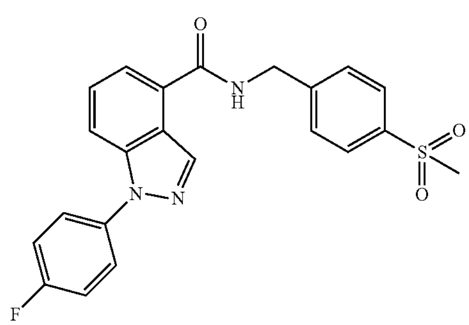 | 1-(4-Fluoro-phenyl)-1H-indazole-4-carboxylic acid 4-methanesulfonyl-benzylamide | 424.2 |
| 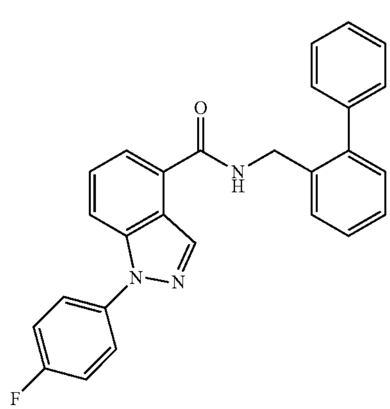 | 1-(4-Fluoro-phenyl)-1H-indazole-4-carboxylic acid (biphenyl-2-ylmethyl)-amide | 422.2 |

TABLE I-continued

| STRUCTURE | Name | Observed [M + H]+ |
|---|---|---|
| 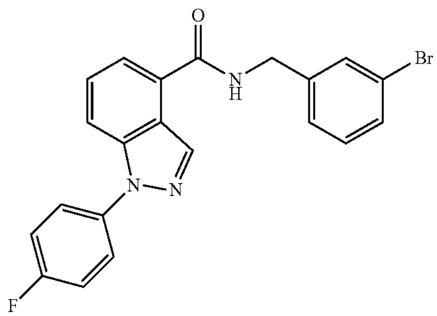 | 1-(4-Fluoro-phenyl)-1H-indazole-4-carboxylic acid 3-bromo-benzylamide | 425.0 |
| 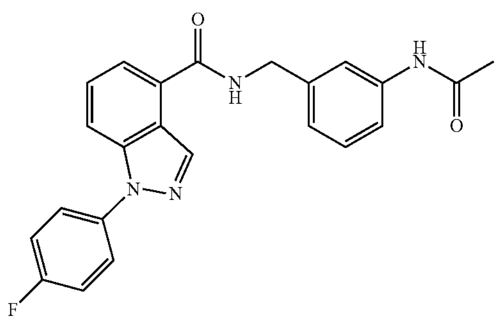 | 1-(4-Fluoro-phenyl)-1H-indazole-4-carboxylic acid 3-acetylamino-benzylamide | 403.1 |
| 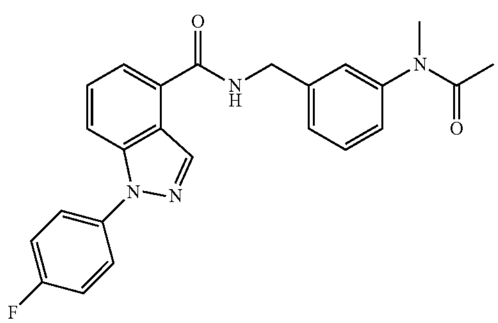 | 1-(4-Fluoro-phenyl)-1H-indazole-4-carboxylic acid 3-(acetyl-methyl-amino)-benzylamide | 417.2 |
| 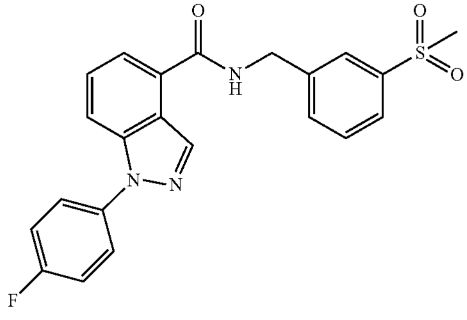 | 1-(4-Fluoro-phenyl)-1H-indazole-4-carboxylic acid 3-methanesulfonyl-benzylamide | 424.2 |

TABLE I-continued
| STRUCTURE | Name | Observed [M + H]+ |
|---|---|---|
| 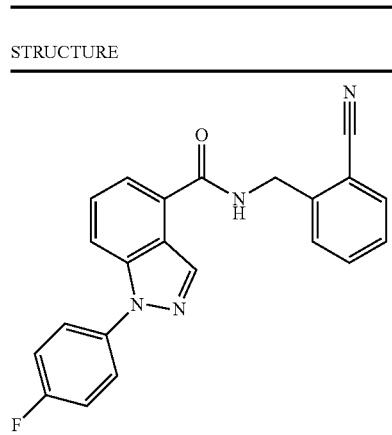 | 1-(4-Fluoro-phenyl)-1H-indazole-4-carboxylic acid 2-cyano-benzylamide | 371.1 |
| 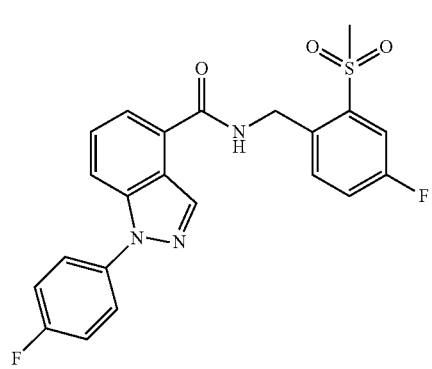 | 1-(4-Fluoro-phenyl)-1H-indazole-4-carboxylic acid 4-fluoro-2-methanesulfonyl-benzylamide | 442.2 |
| 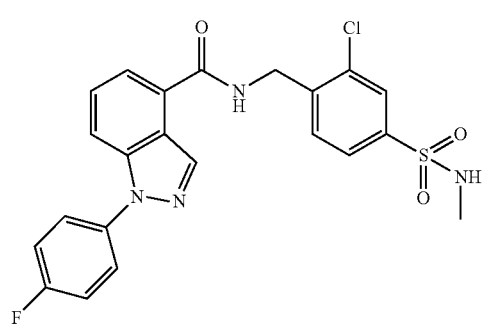 | 1-(4-Fluoro-phenyl)-1H-indazole-4-carboxylic acid 2-chloro-4-methylsulfamoyl-benzylamide | 473.6 |
| 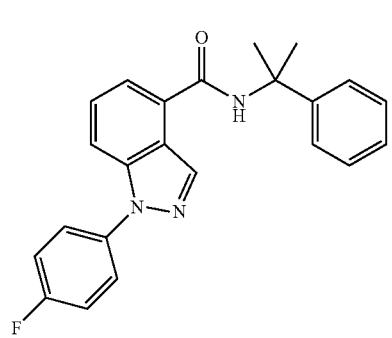 | 1-(4-Fluoro-phenyl)-1H-indazole-4-carboxylic acid (1-methyl-1-phenyl-ethyl)-amide | 374.1 |

TABLE I-continued

| STRUCTURE | Name | Observed [M + H]+ |
|---|---|---|
| 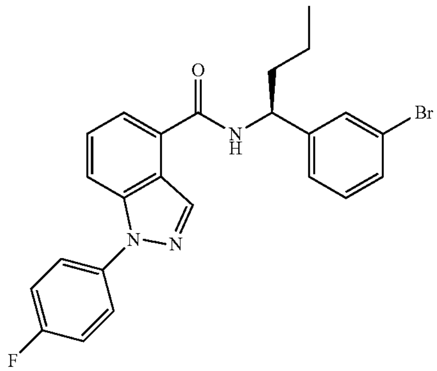 | 1-(4-Fluoro-phenyl)-1H-indazole-4-carboxylic acid [(S)-1-(3-bromo-phenyl)-butyl]-amide | 467.1 |
| 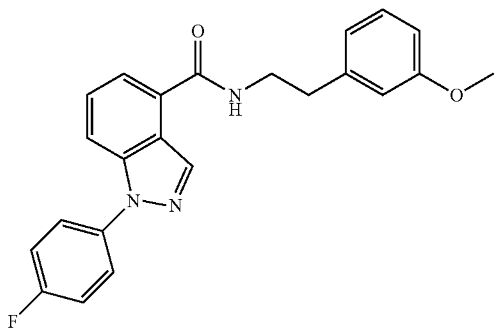 | 1-(4-Fluoro-phenyl)-1H-indazole-4-carboxylic acid [2-(3-methoxy-phenyl)-ethyl]-amide | 390.1 |
| 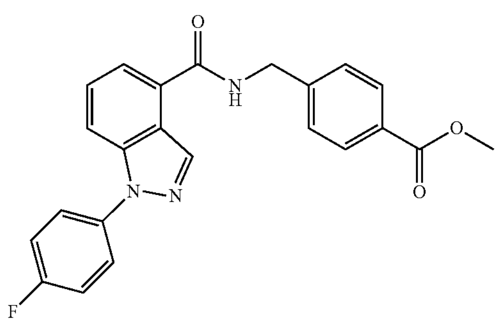 | 4-({[1-(4-Fluoro-phenyl)-1H-indazole-4-carbonyl]-amino}-methyl)-benzoic acid methyl ester | 404.1 |
| 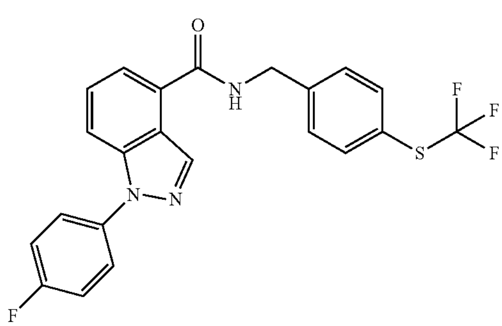 | 1-(4-Fluoro-phenyl)-1H-indazole-4-carboxylic acid 4-trifluoromethylsulfanyl-benzylamide | 446.1 |

TABLE I-continued
| STRUCTURE | Name | Observed [M + H]+ |
|---|---|---|
| 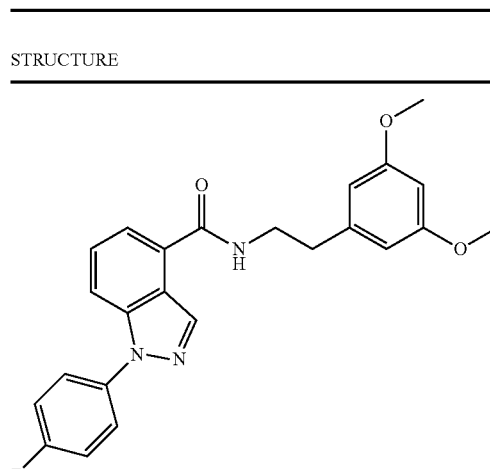 | 1-(4-Fluoro-phenyl)-1H-indazole-4-carboxylic acid [2-(3,5-dimethoxy-phenyl)-ethyl]-amide | 420.2 |
| 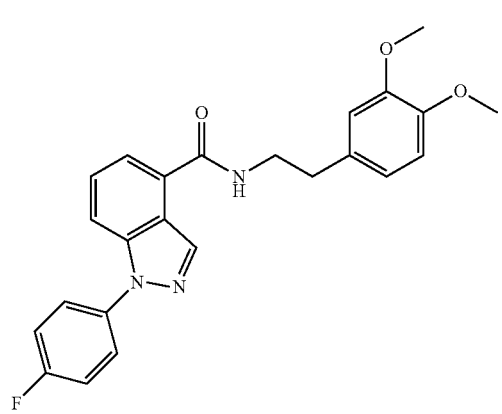 | 1-(4-Fluoro-phenyl)-1H-indazole-4-carboxylic acid [2-(3,4-dimethoxy-phenyl)-ethyl]-amide | 420.2 |
| 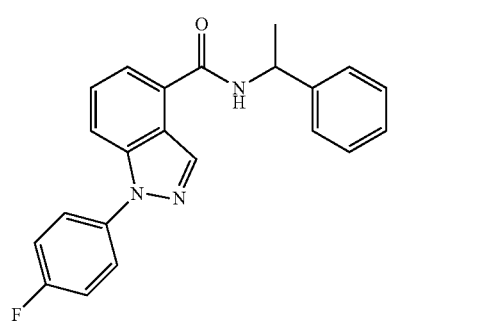 | 1-(4-Fluoro-phenyl)-1H-indazole-4-carboxylic acid (1-phenyl-ethyl)-amide | 360.1 |
| 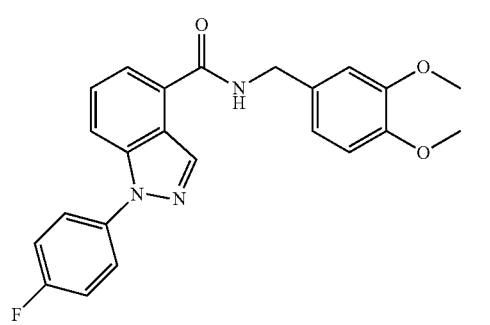 | 1-(4-Fluoro-phenyl)-1H-indazole-4-carboxylic acid 3,4-dimethoxy-benzylamide | 406.1 |

TABLE I-continued

| STRUCTURE | Name | Observed [M + H]+ |
|---|---|---|
| 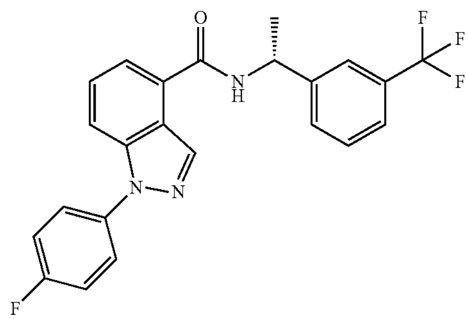 | 1-(4-Fluoro-phenyl)-1H-indazole-4-carboxylic acid [(R)-1-(3-trifluoromethyl-phenyl)-ethyl]-amide | 428.1 |
| 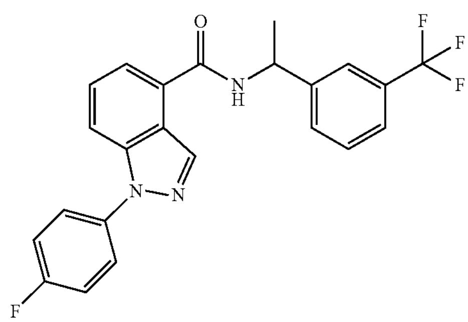 | 1-(4-Fluoro-phenyl)-1H-indazole-4-carboxylic acid [1-(3-trifluoromethyl-phenyl)-ethyl]-amide | 428.1 |
| 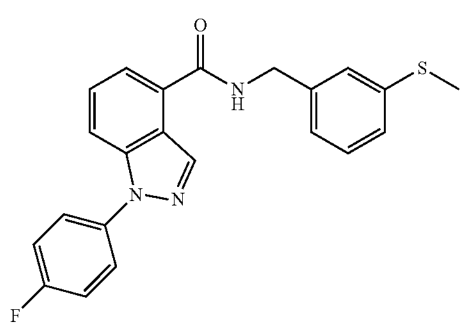 | 1-(4-Fluoro-phenyl)-1H-indazole-4-carboxylic acid 3-methylsulfanyl-benzylamide | 392.2 |
| 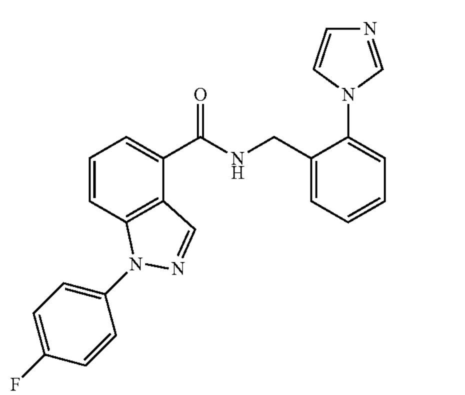 | 1-(4-Fluoro-phenyl)-1H-indazole-4-carboxylic acid 2-imidazol-1-yl-benzylamide | 412.1 |

TABLE I-continued

| STRUCTURE | Name | Observed [M + H]+ |
|---|---|---|
| 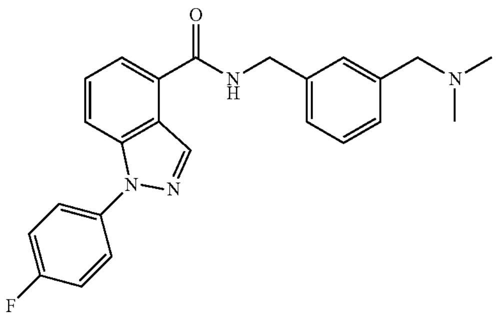 | 1-(4-Fluoro-phenyl)-1H-indazole-4-carboxylic acid 3-dimethylaminomethyl-benzylamide | 403.2 |
| 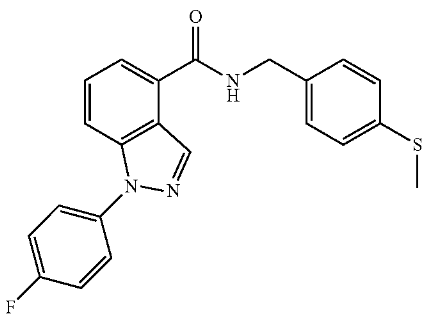 | 1-(4-Fluoro-phenyl)-1H-indazole-4-carboxylic acid 4-methylsulfanyl-benzylamide | 392.2 |
| 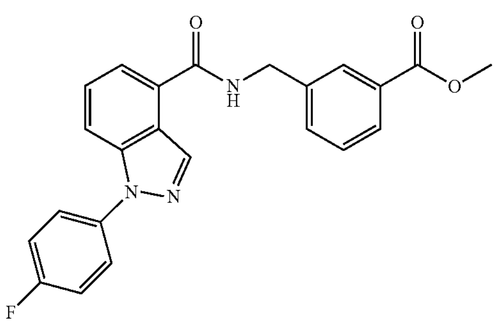 | 3-({[1-(4-Fluoro-phenyl)-1H-indazole-4-carbonyl]-amino}-methyl)-benzoic acid methyl ester | 404.1 |
| 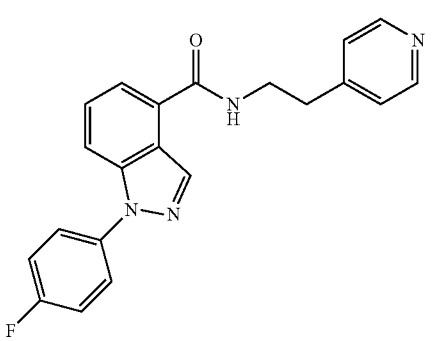 | 1-(4-Fluoro-phenyl)-1H-indazole-4-carboxylic acid (2-pyridin-4-yl-ethyl)-amide | 361.1 |

TABLE I-continued

| STRUCTURE | Name | Observed [M + H]+ |
|---|---|---|
| 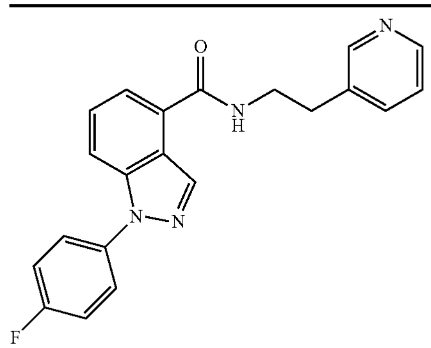 | 1-(4-Fluoro-phenyl)-1H-indazole-4-carboxylic acid (2-pyridin-3-yl-ethyl)-amide | 361.1 |
| 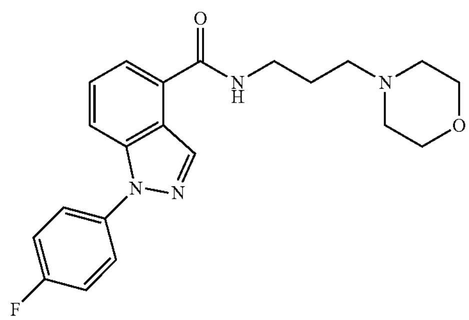 | 1-(4-Fluoro-phenyl)-1H-indazole-4-carboxylic acid (3-morpholin-4-yl-propyl)-amide | 383.1 |
| 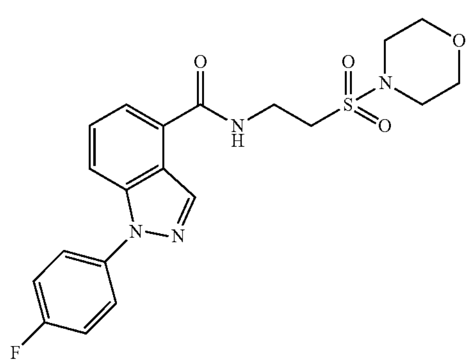 | 1-(4-Fluoro-phenyl)-1H-indazole-4-carboxylic acid [2-(morpholine-4-sulfonyl)-ethyl]-amide | 433.2 |
| 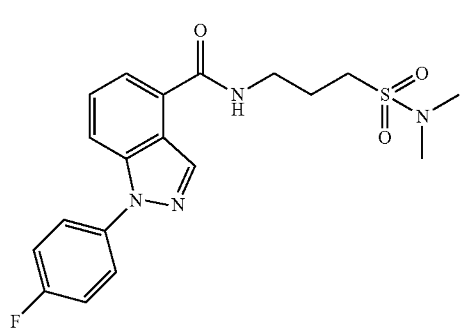 | 1-(4-Fluoro-phenyl)-1H-indazole-4-carboxylic acid (3-dimethylsulfamoyl-propyl)-amide | 405.2 |

TABLE I-continued

| STRUCTURE | Name | Observed [M + H]+ |
|---|---|---|
| 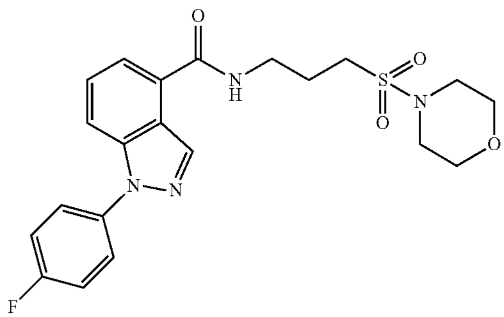 | 1-(4-Fluoro-phenyl)-1H-indazole-4-carboxylic acid [3-(morpholine-4-sulfonyl)-propyl]-amide | 447.2 |
| 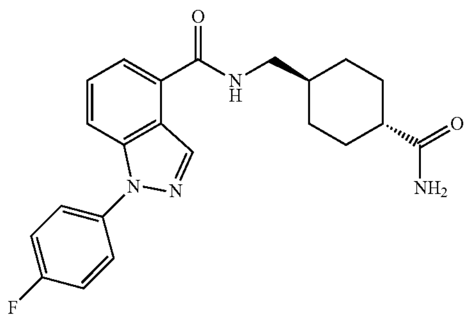 | 1-(4-Fluoro-phenyl)-1H-indazole-4-carboxylic acid (4-carbamoyl-cyclohexylmethyl)-amide | 395.1 |
| 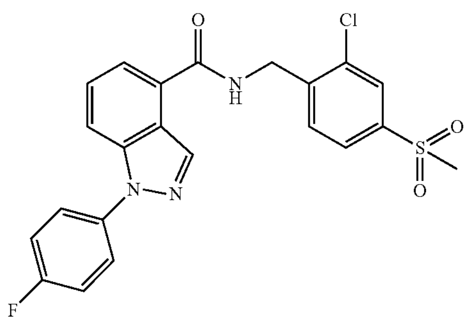 | 1-(4-Fluoro-phenyl)-1H-indazole-4-carboxylic acid 2-chloro-4-methanesulfonyl-benzylamide | 458.6 |
| 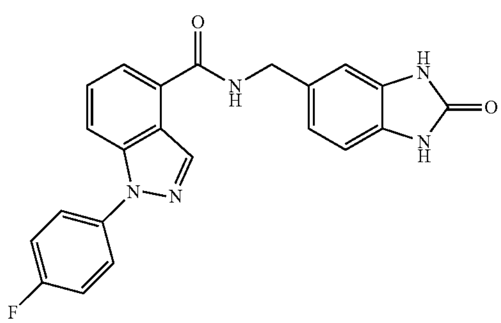 | 1-(4-Fluoro-phenyl)-1H-indazole-4-carboxylic acid (2-oxo-2,3-dihydro-1H-benzoimidazol-5-ylmethyl)-amide | 402.1 |
| 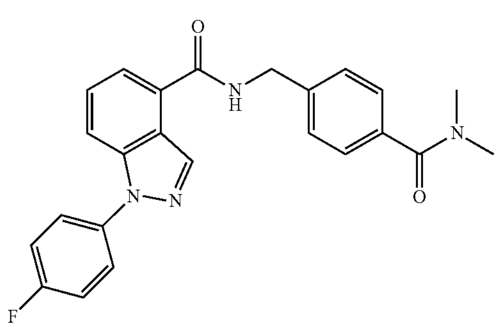 | 1-(4-Fluoro-phenyl)-1H-indazole-4-carboxylic acid 4-dimethylcarbamoyl-benzylamide | 417.2 |

TABLE I-continued

| STRUCTURE | Name | Observed [M + H]+ |
|---|---|---|
| 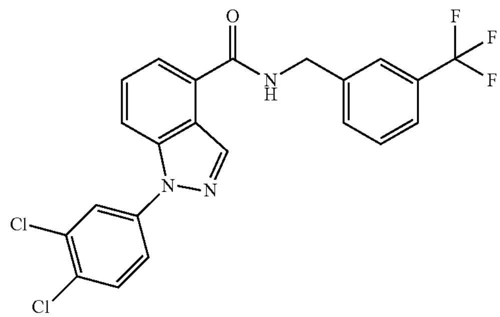 | 1-(3,4-Dichloro-phenyl)-1H-indazole-4-carboxylic acid 3-trifluoromethyl benzylamide | 464.4 |
| 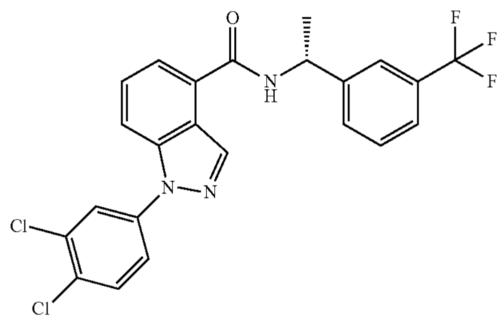 | 1-(3,4-Dichloro-phenyl)-1H-indazole-4-carboxylic acid [(R)-1-(3-trifluoromethyl-phenyl)-ethyl]-amide | 478.4 |
| 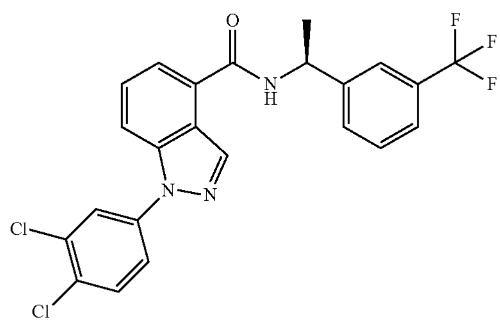 | 1-(3,4-Dichloro-phenyl)-1H-indazole-4-carboxylic acid [(S)-1-(3-trifluoromethyl-phenyl)-ethyl]-amide | 478.4 |
| 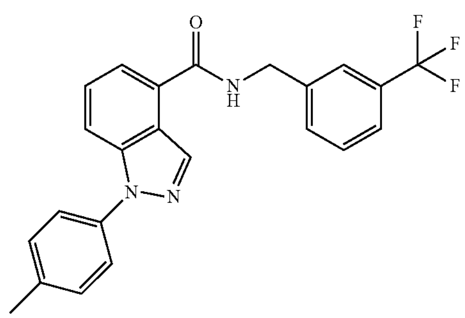 | 1-p-Tolyl-1H-indazole-4-carboxylic acid 3-trifluoromethyl-benzylamide | 410.5 |
| 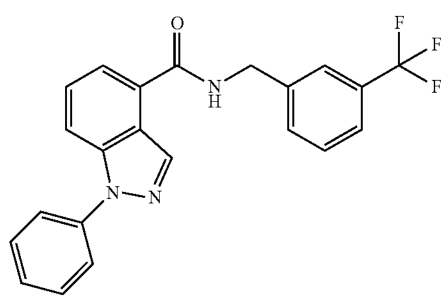 | 1-Phenyl-1H-indazole-4-carboxylic acid 3-trifluoromethyl-benzylamide | 396.5 |

TABLE I-continued

| STRUCTURE | Name | Observed [M + H]+ |
|---|---|---|
| 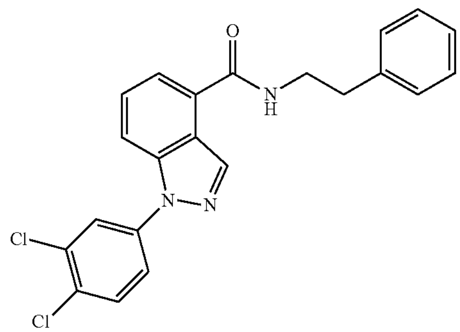 | 1-(3,4-Dichloro-phenyl)-1H-indazole-4-carboxylic acid phenethyl-amide | 410.4 |
| 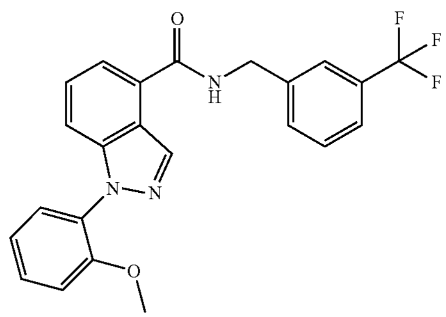 | 1-(2-Methoxy-phenyl)-1H-indazole-4-carboxylic acid 3-trifluoromethyl-benzylamide | 426.4 |
| 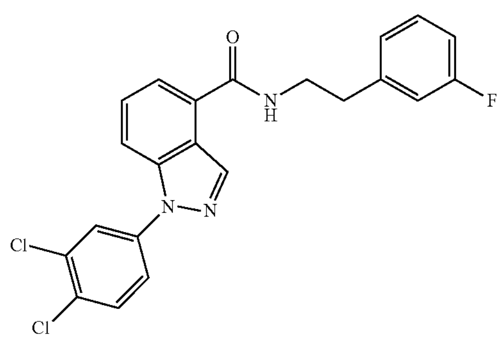 | 1-(3,4-Dichloro-phenyl)-1H-indazole-4-carboxylic acid [2-(3-fluoro-phenyl)-ethyl]-amide | 428.3 |
| 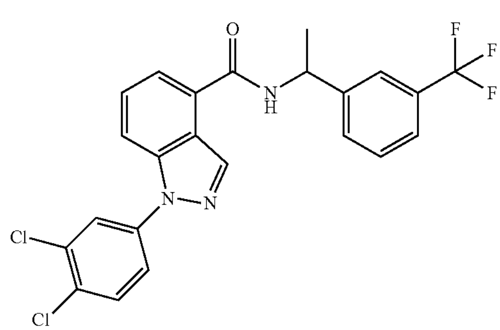 | 1-(3,4-Dichloro-phenyl)-1H-indazole-4-carboxylic acid [1-(3-trifluoromethyl-phenyl)-ethyl]-amide | 478.3 |

TABLE I-continued

| STRUCTURE | Name | Observed [M + H]+ |
|---|---|---|
| 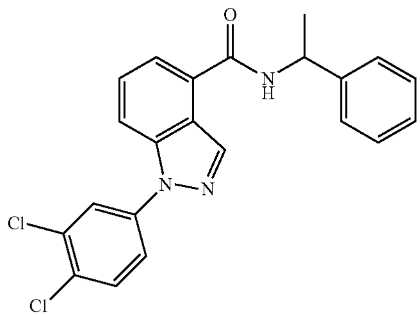 | 1-(3,4-Dichloro-phenyl)-1H-indazole-4-carboxylic acid (1-phenyl-ethyl)-amide | 410.4 |
| 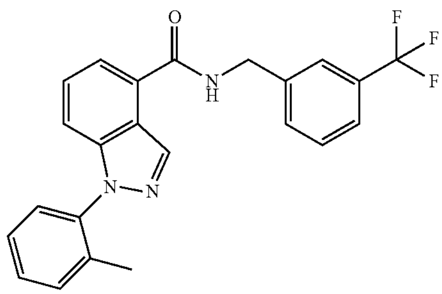 | 1-o-Tolyl-1H-indazole-4-carboxylic acid 3-trifluoromethyl-benzylamide | 410.5 |
| 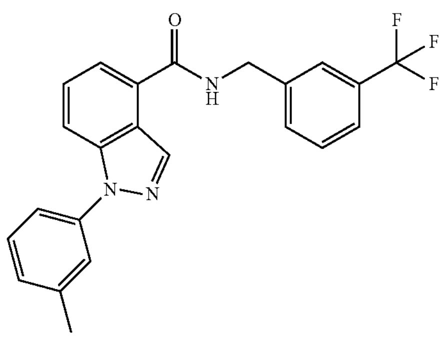 | 1-m-Tolyl-1H-indazole-4-carboxylic acid 3-trifluoromethyl-benzylamide | 410.5 |
| 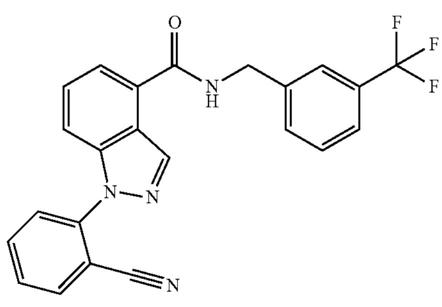 | 1-(2-Cyano-phenyl)-1H-indazole-4-carboxylic acid 3-trifluoromethyl-benzylamide | 421.5 |
| 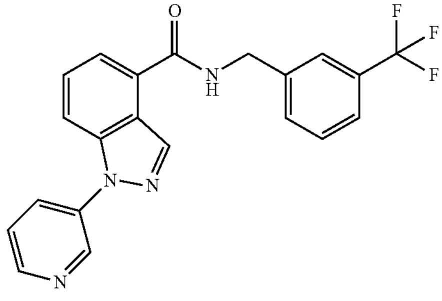 | 1-Pyridin-3-yl-1H-indazole-4-carboxylic acid 3-trifluoromethyl-benzylamide | 397.5 |

TABLE I-continued

| STRUCTURE | Name | Observed [M + H]+ |
|---|---|---|
| 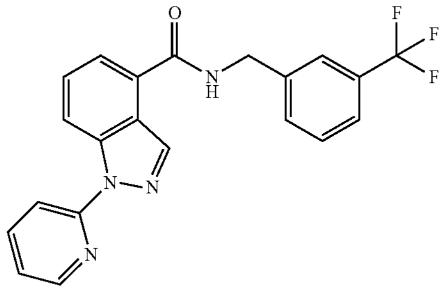 | 1-Pyridin-2-yl-1H-indazole-4-carboxylic acid 3-trifluoromethyl-benzylamide | 397.5 |
| | 1-(2-Fluoro-phenyl)-1H-indazole-4-carboxylic acid 3-trifluoromethyl-benzylamide | 414.4 |
| | 1-(2-Fluoro-phenyl)-1H-indazole-4-carboxylic acid 3-trifluoromethyl-benzylamide | 413.9 |
| 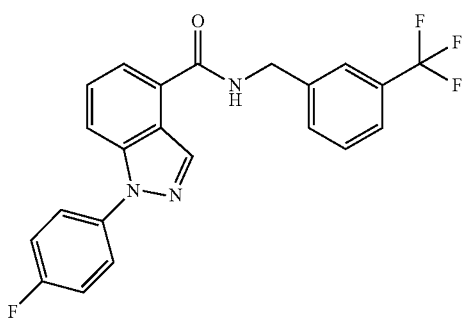 | 1-(4-Fluoro-phenyl)-1H-indazole-4-carboxylic acid 3-trifluoromethyl-benzylamide | 414.9 |
| 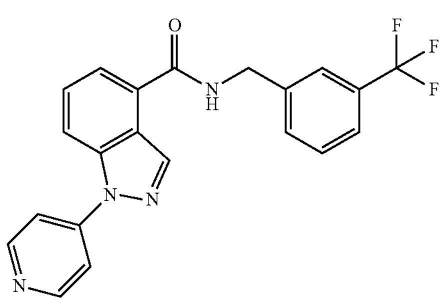 | 1-Pyridin-4-yl-1H-indazole-4-carboxylic acid 3-trifluoromethyl-benzylamide | 397.5 |

TABLE I-continued

| STRUCTURE | Name | Observed [M + H]+ |
|---|---|---|
| 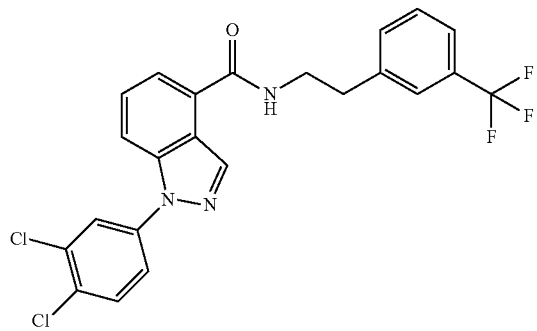 | 1-(3,4-Dichloro-phenyl)-1H-indazole-4-carboxylic acid [2-(3-trifluoromethyl-phenyl)-ethyl]-amide | 478.4 |
| 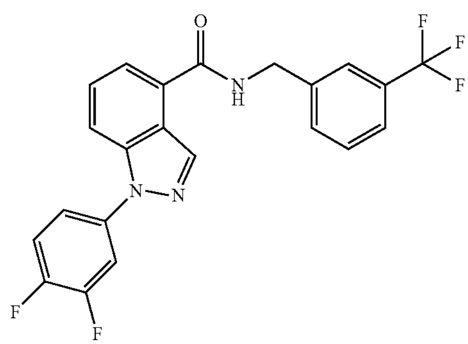 | 1-(3,4-Difluoro-benzyl)-1H-indazole-4-carboxylic acid 3-trifluoromethyl-benzylamide | 432.4 |
| 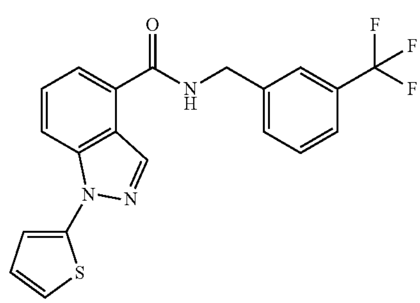 | 1-Thiophen-2-yl-1H-indazole-4-carboxylic acid 3-trifluoromethyl-benzylamide | 402.5 |
| 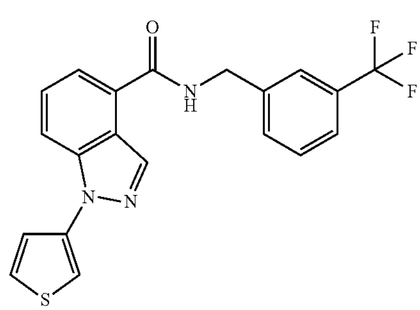 | 1-Thiophen-3-yl-1H-indazole-4-carboxylic acid 3-trifluoromethyl-benzylamide | 402.5 |

TABLE I-continued

| STRUCTURE | Name | Observed [M + H]+ |
|---|---|---|
| 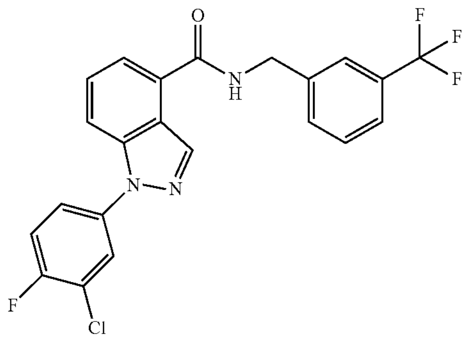 | 1-(3-Chloro-4-fluoro-benzyl)-1H-indazole-4-carboxylic acid 3-trifluoromethyl-benzylamide | 448.4 |
| 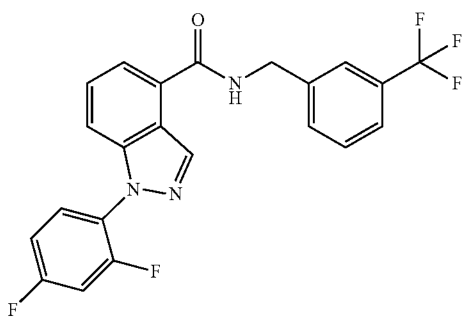 | 1-(2,4-Difluoro-benzyl)-1H-indazole-4-carboxylic acid 3-trifluoromethyl-benzylamide | 431.6 |
| 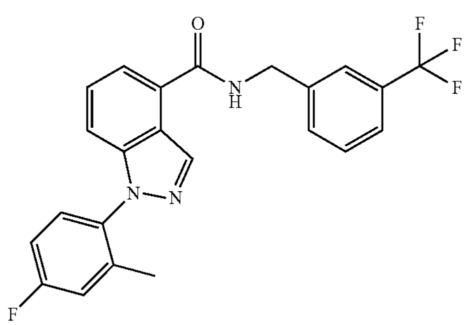 | 1-(4-Fluoro-2-methyl-benzyl)-1H-indazole-4-carboxylic acid 3-trifluoromethyl-benzylamide | 428.2 |
| 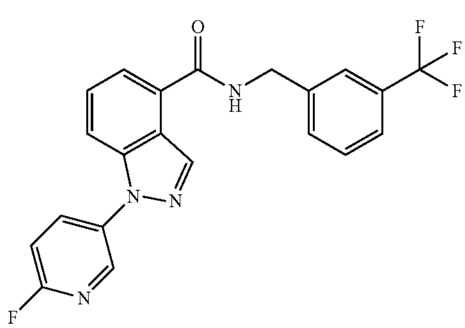 | 1-(6-Fluoro-pyridin-3-yl)-1H-indazole-4-carboxylic acid 3-trifluoromethyl-benzylamide | 415.4 |

TABLE I-continued

| STRUCTURE | Name | Observed [M + H]+ |
|---|---|---|
| 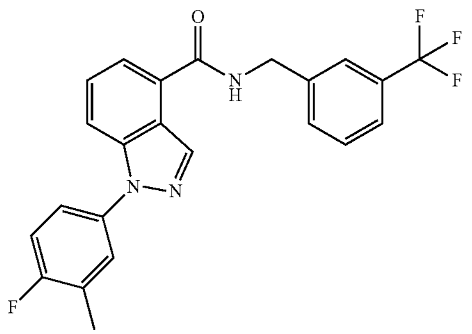 | 1-(4-Fluoro-3-methyl-benzyl)-1H-indazole-4-carboxylic acid 3-trifluoromethyl-benzylamide | 428.2 |
| 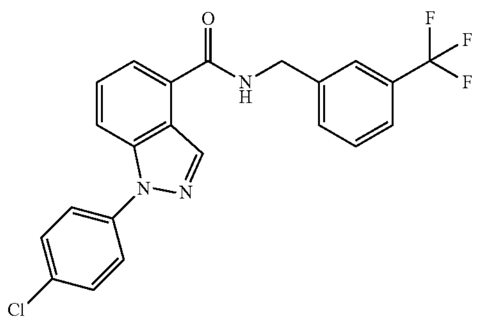 | 1-(4-Chloro-benzyl)-1H-indazole-4-carboxylic acid 3-trifluoromethyl-benzylamide | 430.5 |
| 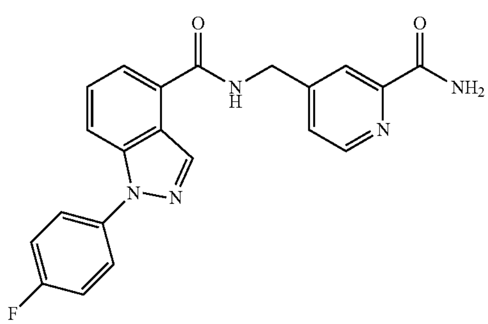 | 1-(4-Fluoro-phenyl)-1H-indazole-4-carboxylic acid (2-carbamoyl-pyridin-4-ylmethyl)-amide | 390.9 |
| 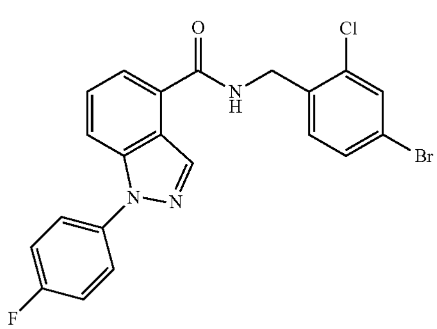 | 1-(4-Fluoro-phenyl)-1H-indazole-4-carboxylic acid 4-bromo-2-chloro-benzylamide | 460.5 |

TABLE I-continued

| STRUCTURE | Name | Observed [M + H]+ |
|---|---|---|
| 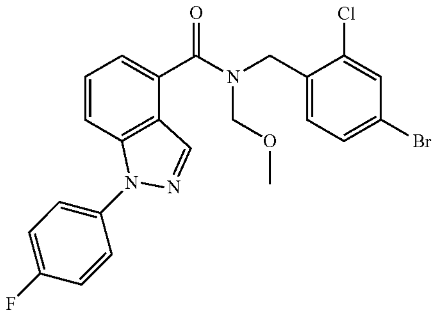 | 1-(4-Fluoro-phenyl)-1H-indazole-4-carboxylic acid (4-bromo-2-chloro-benzyl)-methoxymethyl-amide | 504.5 |
| 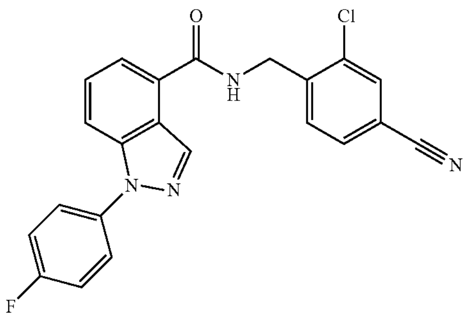 | 1-(4-Fluoro-phenyl)-1H-indazole-4-carboxylic acid 2-chloro-4-cyano-benzylamide | 405.6 |
| 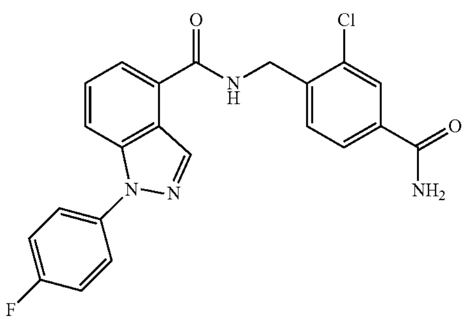 | 1-(4-Fluoro-phenyl)-1H-indazole-4-carboxylic acid 4-carbamoyl-2-chloro-benzylamide | 423.7 |
| 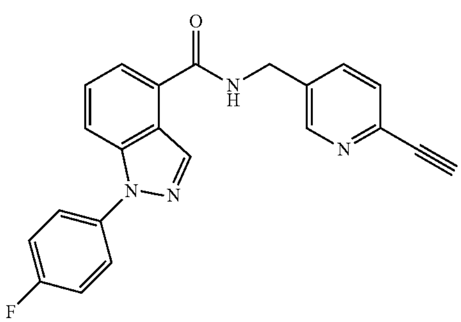 | 1-(4-Fluoro-phenyl)-1H-indazole-4-carboxylic acid (6-ethynyl-pyridin-3-ylmethyl)-amide | 371.9 |
| 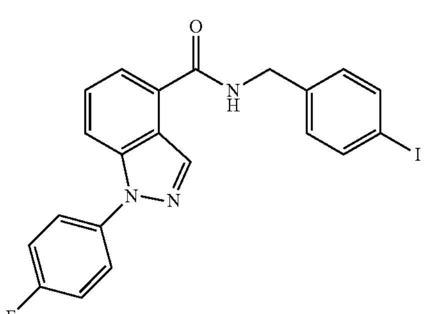 | 1-(4-Fluoro-phenyl)-1H-indazole-4-carboxylic acid 4-iodo-benzylamide | 472.3 |

TABLE I-continued

| STRUCTURE | Name | Observed [M + H]+ |
|---|---|---|
| 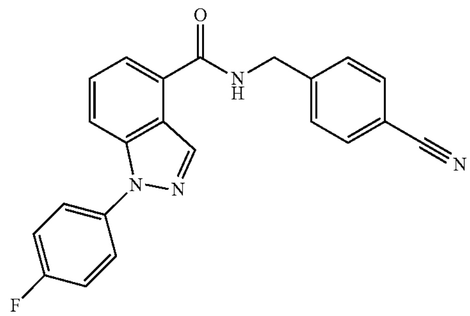 | 1-(4-Fluoro-phenyl)-1H-indazole-4-carboxylic acid 4-cyano-benzylamide | 371.3 |
| 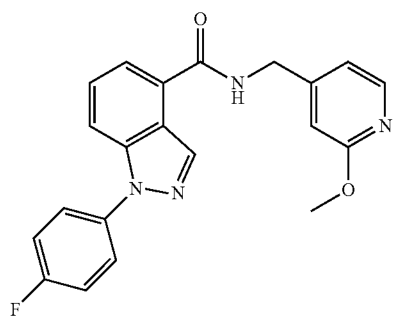 | 1-(4-Fluoro-phenyl)-1H-indazole-4-carboxylic acid (2-methoxy-pyridin-4-ylmethyl)-amide | 377.9 |
| 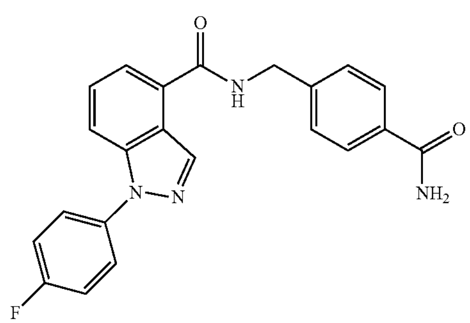 | 1-(4-Fluoro-phenyl)-1H-indazole-4-carboxylic acid 4-carbamoyl-benzylamide | 389.7 |
| 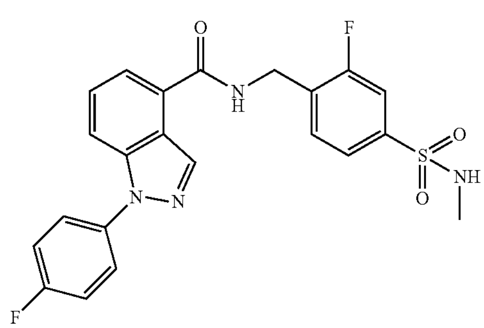 | 1-(4-Fluoro-phenyl)-1H-indazole-4-carboxylic acid 2-fluoro-4-methylsulfamoyl-benzylamide | 456.1 |

TABLE I-continued

| STRUCTURE | Name | Observed [M + H]+ |
|---|---|---|
| 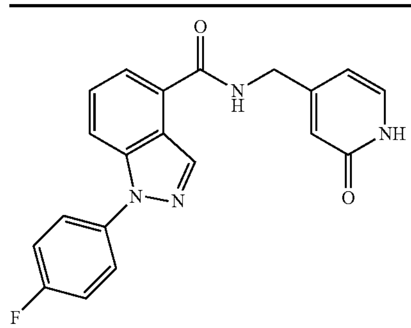 | 1-(4-Fluoro-phenyl)-1H-indazole-4-carboxylic acid (2-oxo-1,2-dihydro-pyridin-4-ylmethyl)-amide | 363.9 |
| 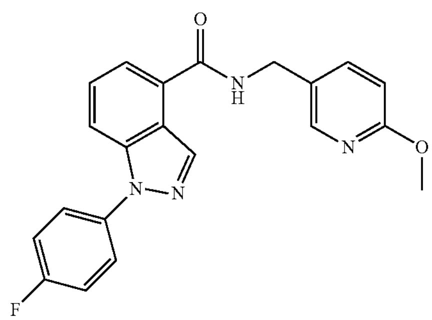 | 1-(4-Fluoro-phenyl)-1H-indazole-4-carboxylic acid (6-methoxy-pyridin-3-ylmethyl)-amide | 377.9 |
| 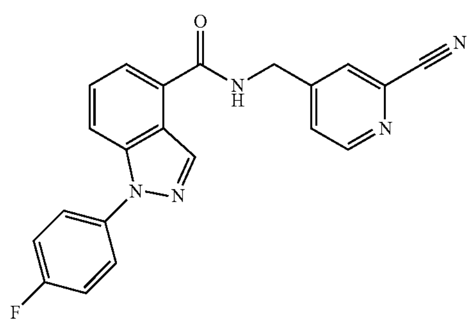 | 1-(4-Fluoro-phenyl)-1H-indazole-4-carboxylic acid (2-cyano-pyridin-4-ylmethyl)-amide | 372.4 |
| 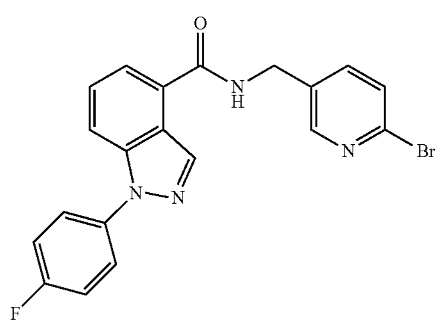 | 1-(4-Fluoro-phenyl)-1H-indazole-4-carboxylic acid (6-bromo-pyridin-3-ylmethyl)-amide | 425.4/427.4 |
| 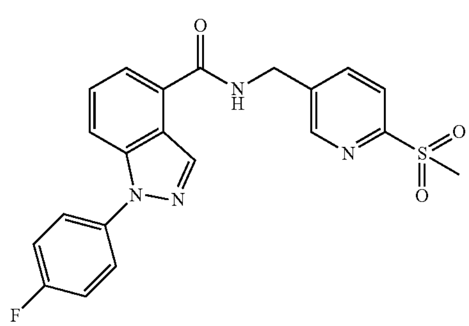 | 1-(4-Fluoro-phenyl)-1H-indazole-4-carboxylic acid (6-methanesulfonyl-pyridin-3-ylmethyl)-amide | 426.0 |

TABLE I-continued

| STRUCTURE | Name | Observed [M + H]+ |
|---|---|---|
| 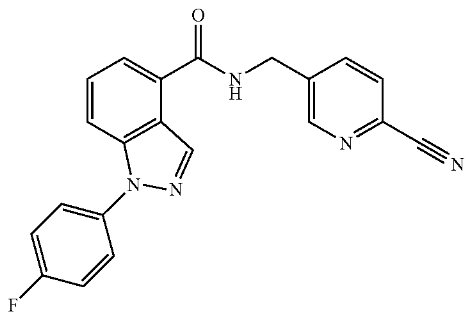 | 1-(4-Fluoro-phenyl)-1H-indazole-4-carboxylic acid (6-cyano-pyridin-3-ylmethyl)-amide | 373.0 |
| 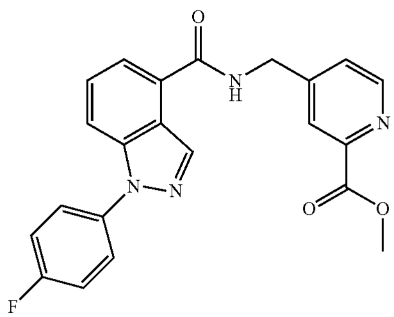 | 4-({[1-(4-Fluoro-phenyl)-1H-indazole-4-carbonyl]-amino}-methyl)-pyridine-2-carboxylic acid methyl ester | 405.9 |
| 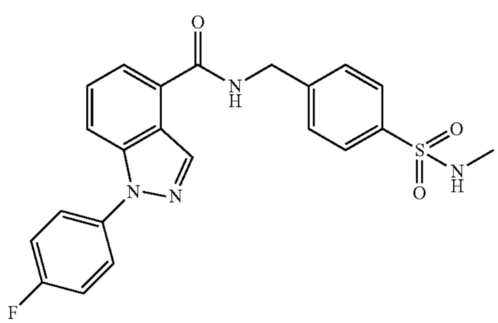 | 1-(4-Fluoro-phenyl)-1H-indazole-4-carboxylic acid 4-methylsulfamoyl-benzylamide | 439.7 |
| 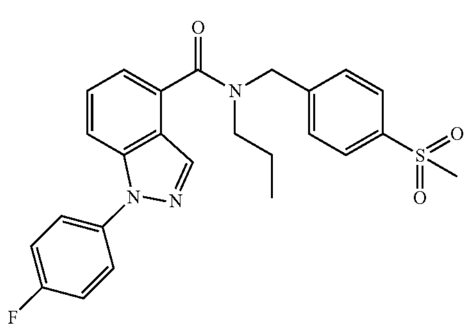 | 1-(4-Fluoro-phenyl)-1H-indazole-4-carboxylic acid (4-methanesulfonyl-benzyl)-propyl-amide | 466.4 |

TABLE I-continued

| STRUCTURE | Name | Observed [M + H]+ |
|---|---|---|
| 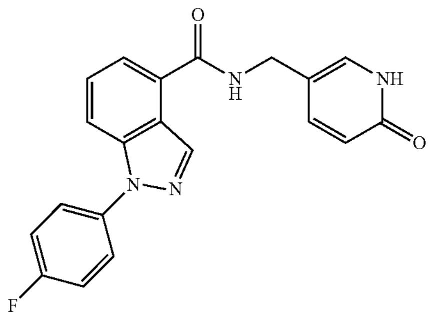 | 1-(4-Fluoro-phenyl)-1H-indazole-4-carboxylic acid (6-oxo-1,6-dihydro-pyridin-3-ylmethyl)-amide | 363.9 |
| 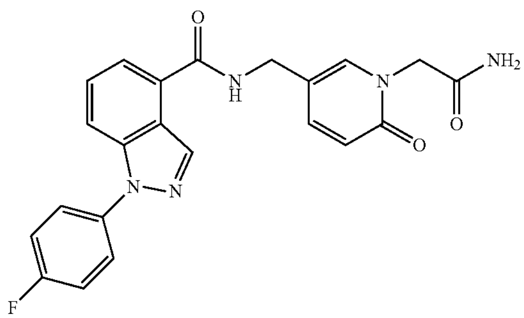 | 1-(4-Fluoro-phenyl)-1H-indazole-4-carboxylic acid (1-carbamoylmethyl-6-oxo-1,6-dihydro-pyridin-3-ylmethyl)-amide | 420.9 |
| 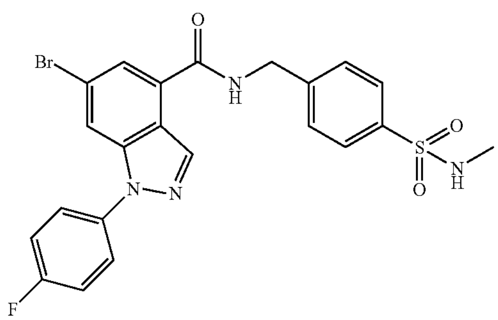 | 6-Bromo-1-(4-fluoro-phenyl)-1H-indazole-4-carboxylic acid 4-methylsulfamoyl-benzylamide | 517.4 |
| 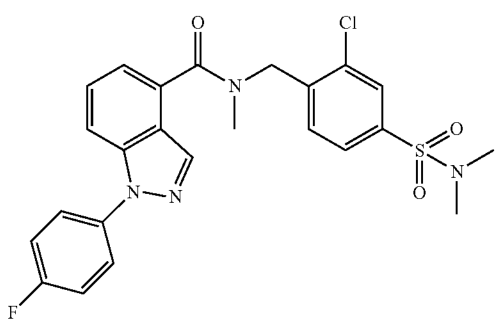 | 1-(4-Fluoro-phenyl)-1H-indazole-4-carboxylic acid (2-chloro-4-dimethylsulfamoyl-benzyl)-methyl-amide | 520.5 |
| 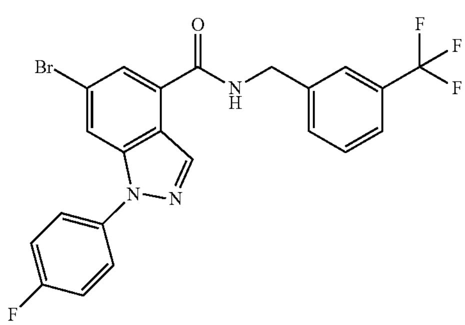 | 6-Bromo-1-(4-fluoro-phenyl)-1H-indazole-4-carboxylic acid 3-trifluoromethyl-benzylamide | 492.4 |

TABLE I-continued

| STRUCTURE | Name | Observed [M + H]+ |
|---|---|---|
| 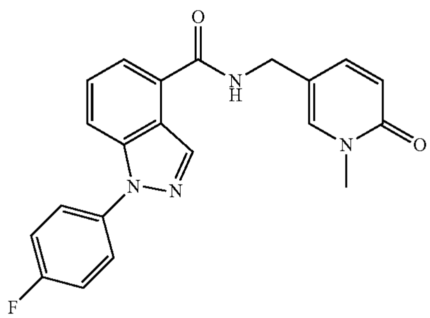 | 1-(4-Fluoro-phenyl)-1H-indazole-4-carboxylic acid (1-methyl-6-oxo-1,6-dihydro-pyridin-3-ylmethyl)-amide | 377.9 |
| 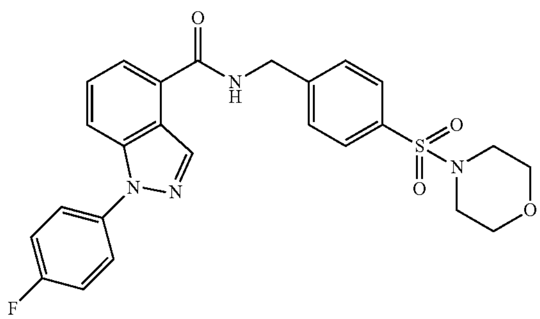 | 1-(4-Fluoro-phenyl)-1H-indazole-4-carboxylic acid 4-(morpholine-4-sulfonyl)-benzylamide | 496.0 |
| 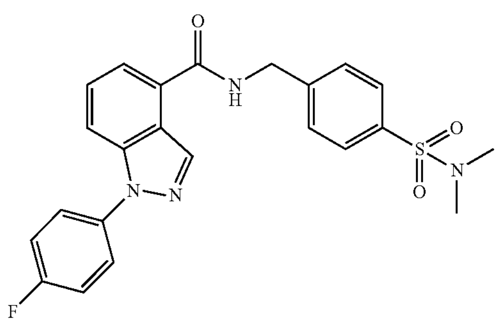 | 1-(4-Fluoro-phenyl)-1H-indazole-4-carboxylic acid 4-dimethylsulfamoyl-benzylamide | 452.5 |
| 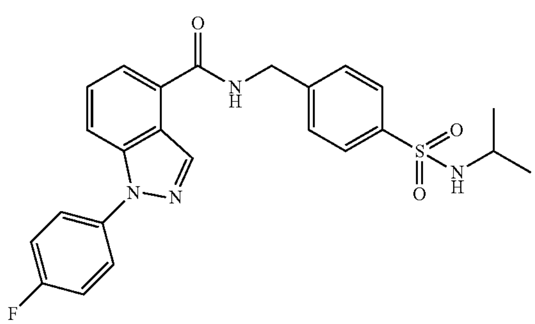 | 1-(4-Fluoro-phenyl)-1H-indazole-4-carboxylic acid 4-isopropylsulfamoyl-benzylamide | 467.4 |

TABLE I-continued

| STRUCTURE | Name | Observed [M + H]+ |
|---|---|---|
| 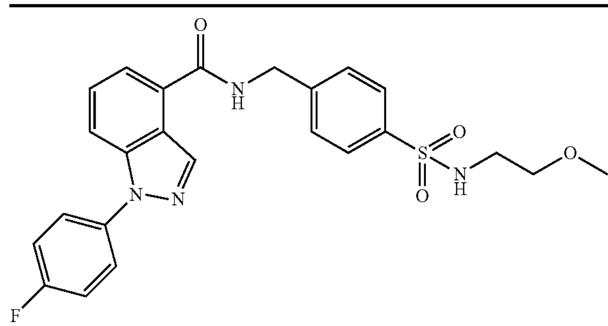 | 1-(4-Fluoro-phenyl)-1H-indazole-4-carboxylic acid 4-(2-methoxy-ethylsulfamoyl)-benzylamide | 483.4 |
| 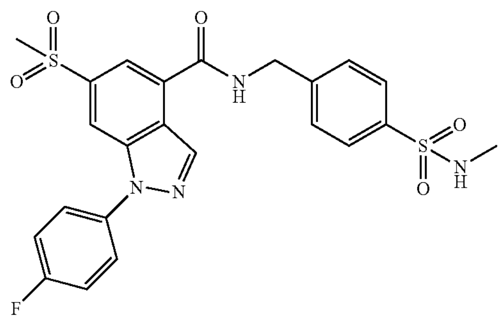 | 1-(4-Fluoro-phenyl)-6-methanesulfonyl-1H-indazole-4-carboxylic acid 4-methylsulfamoyl-benzylamide | 516.1 |
| 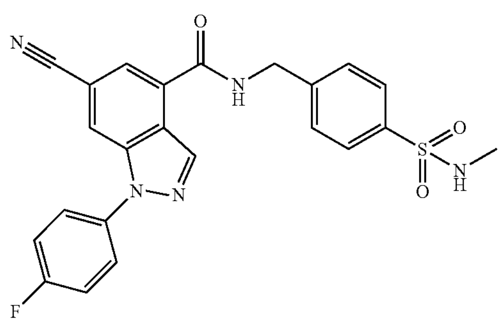 | 6-Cyano-1-(4-fluoro-phenyl)-1H-indazole-4-carboxylic acid 4-methylsulfamoyl-benzylamide | 465.0 |
| 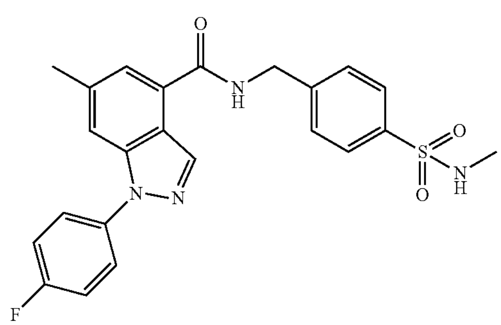 | 1-(4-Fluoro-phenyl)-6-methyl-1H-indazole-4-carboxylic acid 4-methylsulfamoyl-benzylamide | 544.0 |
| 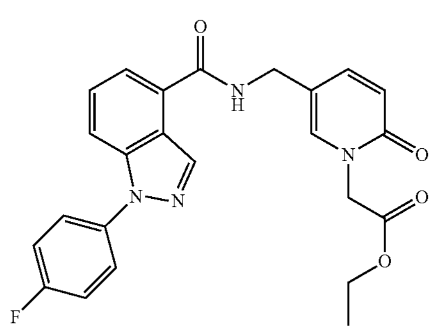 | [5-({[1-(4-Fluoro-phenyl)-1H-indazole-4-carbonyl]-amino}-methyl)-2-oxo-2H-pyridin-1-yl]-acetic acid ethyl ester | 450.0 |

TABLE I-continued

| STRUCTURE | Name | Observed [M + H]+ |
|---|---|---|
| 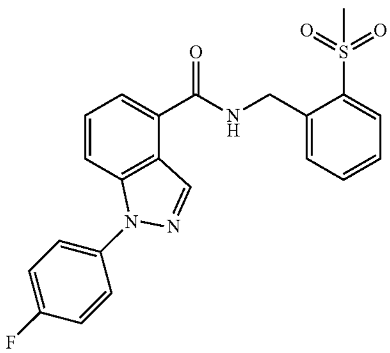 | 1-(4-Fluoro-phenyl)-1H-indazole-4-carboxylic acid 2-methanesulfonyl-benzylamide | 424.7 |
| 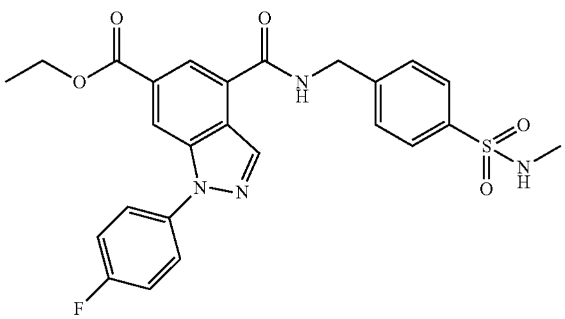 | 1-(4-Fluoro-phenyl)-4-(4-methylsulfamoyl-benzylcarbamoyl)-1H-indazole-6-carboxylic acid ethyl ester | 511.1 |
| 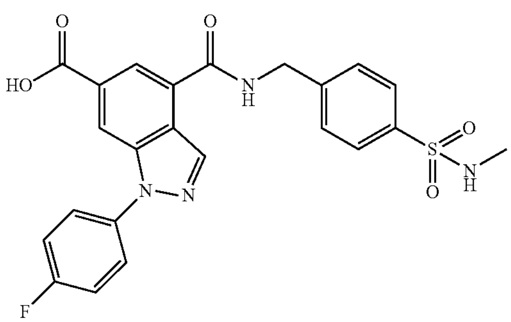 | 1-(4-Fluoro-phenyl)-4-(4-methylsulfamoyl-benzylcarbamoyl)-1H-indazole-6-carboxylic acid | 484.0 |
| 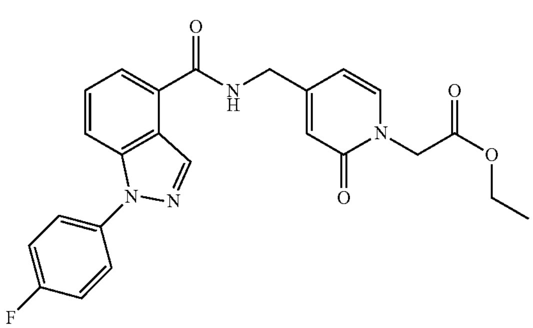 | [4-({[1-(4-Fluoro-phenyl)-1H-indazole-4-carbonyl]-amino}-methyl)-2-oxo-2H-pyridin-1-yl]-acetic acid ethyl ester | 450.0 |

TABLE I-continued

| STRUCTURE | Name | Observed [M + H]+ |
|---|---|---|
| 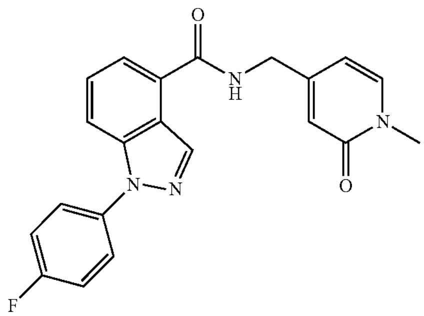 | 1-(4-Fluoro-phenyl)-1H-indazole-4-carboxylic acid (1-methyl-2-oxo-1,2-dihydro-pyridin-4-ylmethyl)-amide | 378.0 |
| 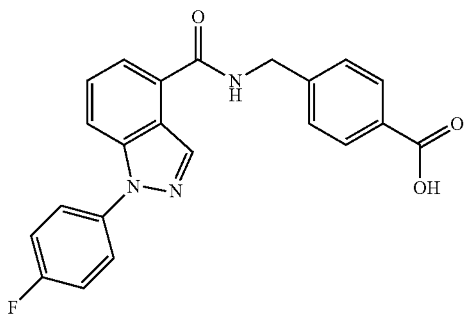 | 4-({[1-(4-Fluoro-phenyl)-1H-indazole-4-carbonyl]-amino}-methyl)-benzoic acid | 390.1 |
| 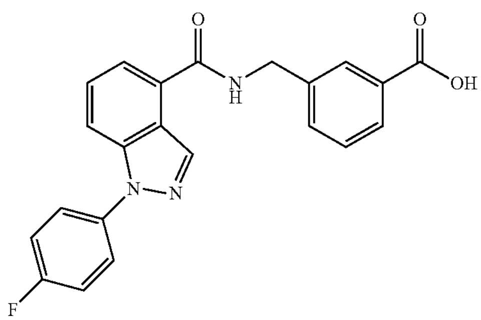 | 3-({[1-(4-Fluoro-phenyl)-1H-indazole-4-carbonyl]-amino}-methyl)-benzoic acid | 390.1 |
| 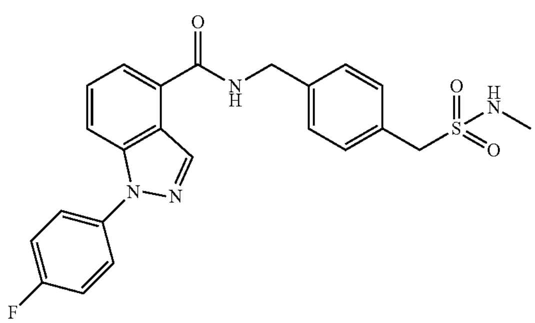 | 1-(4-Fluoro-phenyl)-1H-indazole-4-carboxylic acid 4-methylsulfamoylmethyl-benzylamide | 452.2 |
| 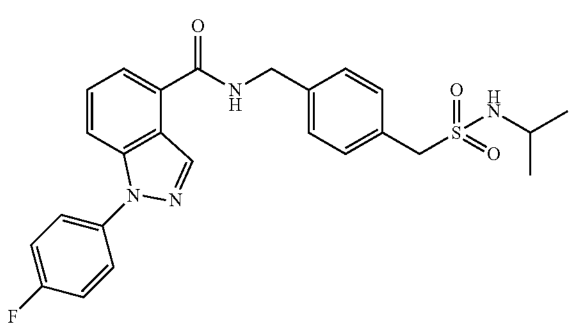 | 1-(4-Fluoro-phenyl)-1H-indazole-4-carboxylic acid 4-(isopropylsulfamoyl-methyl)-benzylamide | 482.0 |

TABLE I-continued

| STRUCTURE | Name | Observed [M + H]+ |
|---|---|---|
| 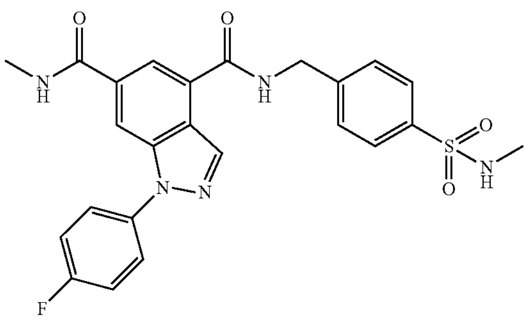 | 1-(4-Fluoro-phenyl)-1H-indazole-4,6-dicarboxylic acid 6-methylamide 4-(4-methylsulfamoyl-benzylamide) | 495.2 |
| 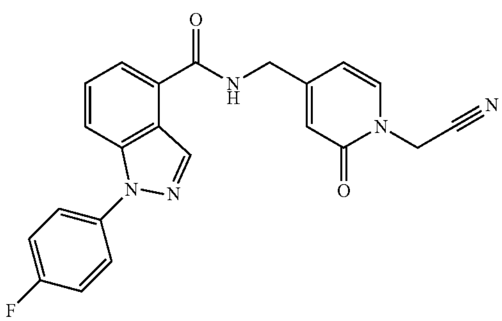 | 1-(4-Fluoro-phenyl)-1H-indazole-4-carboxylic acid (1-cyanomethyl-2-oxo-1,2-dihydro-pyridin-4-ylmethyl)-amide | 402.3 |
| 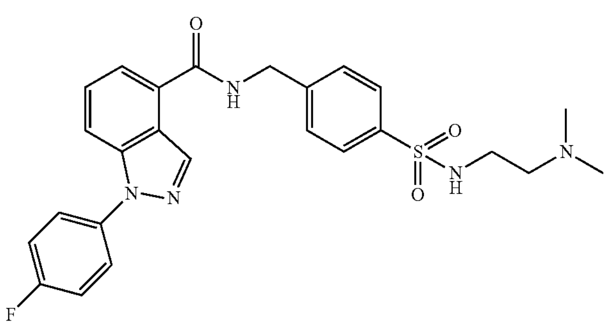 | 1-(4-Fluoro-phenyl)-1H-indazole-4-carboxylic acid 4-(2-dimethylamino-ethylsulfamoyl)-benzylamide | 495.7 |
| 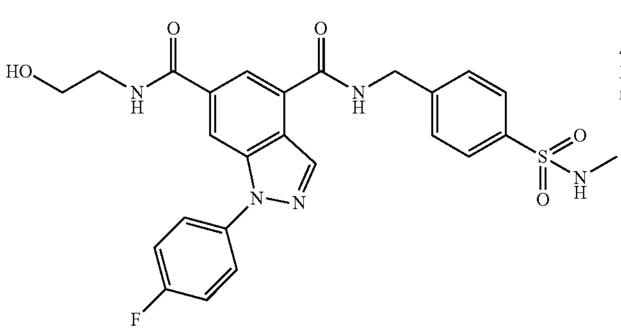 | 1-(4-Fluoro-phenyl)-1H-indazole-4,6-dicarboxylic acid 6-[(2-hydroxy-ethyl)-amide] 4-(4-methylsulfamoyl-benzylamide) | 525.3 |

TABLE I-continued

| STRUCTURE | Name | Observed [M + H]+ |
|---|---|---|
| 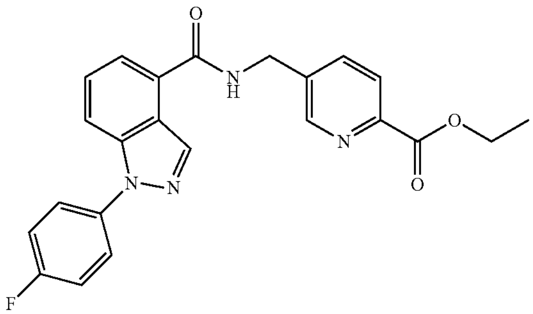 | 5-({[1-(4-Fluoro-phenyl)-1H-indazole-4-carbonyl]-amino}-methyl)-pyridine-2-carboxylic acid ethyl ester | 419.9 |
| 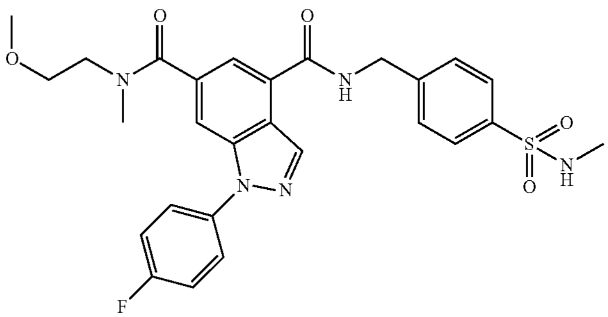 | 1-(4-Fluoro-phenyl)-6-[(2-methoxy-ethyl)-methyl-amino]-1H-indazole-4-carboxylic acid 4-methylsulfamoyl-benzylamide | 524.1 |
| 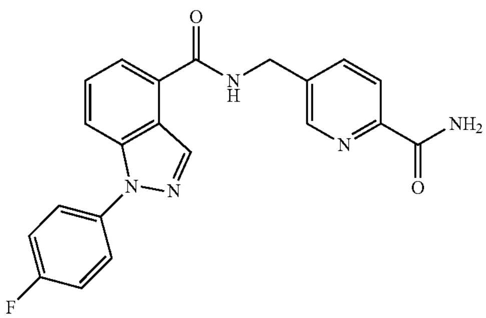 | 1-(4-Fluoro-phenyl)-1H-indazole-4-carboxylic acid (6-carbamoyl-pyridin-3-ylmethyl)-amide | 391.0 |
| 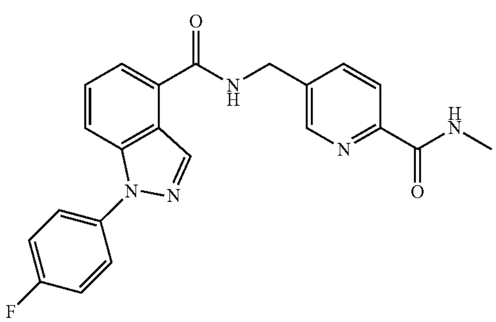 | 1-(4-Fluoro-phenyl)-1H-indazole-4-carboxylic acid (6-methylcarbamoyl-pyridin-3-ylmethyl)-amide | 405.0 |
| 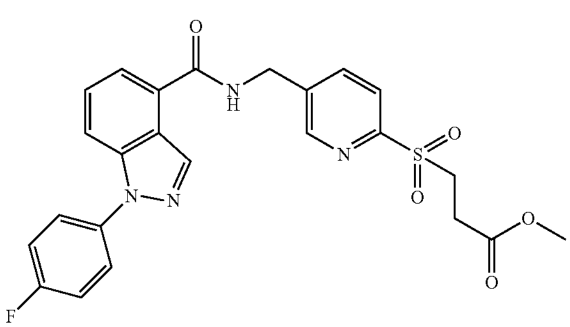 | 3-[5-({[1-(4-Fluoro-phenyl)-1H-indazole-4-carbonyl]-amino}-methyl)-pyridine-2-sulfonyl]-propionic acid methyl ester | 498.0 |

TABLE I-continued

| STRUCTURE | Name | Observed [M + H]+ |
|---|---|---|
| 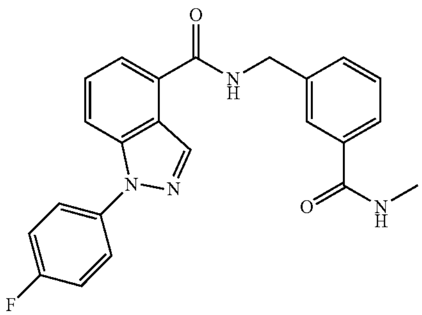 | 1-(4-Fluoro-phenyl)-1H-indazole-4-carboxylic acid 3-methylcarbamoyl-benzylamide | 403.8 |
| 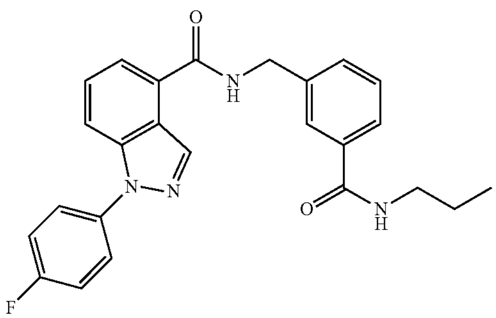 | 1-(4-Fluoro-phenyl)-1H-indazole-4-carboxylic acid 3-propylcarbamoyl-benzylamide | 431.6 |
| 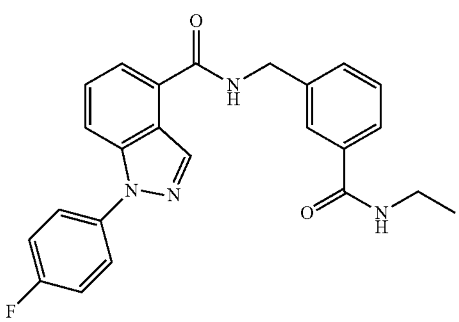 | 1-(4-Fluoro-phenyl)-1H-indazole-4-carboxylic acid 3-ethylcarbamoyl-benzylamide | 417.6 |
| 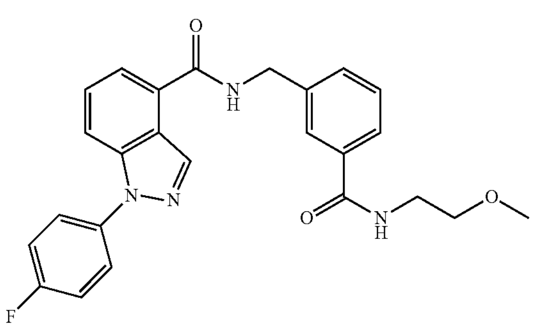 | 1-(4-Fluoro-phenyl)-1H-indazole-4-carboxylic acid 3-(2-methoxy-ethylcarbamoyl)-benzylamide | 447.8 |

TABLE I-continued

| STRUCTURE | Name | Observed [M + H]+ |
|---|---|---|
| 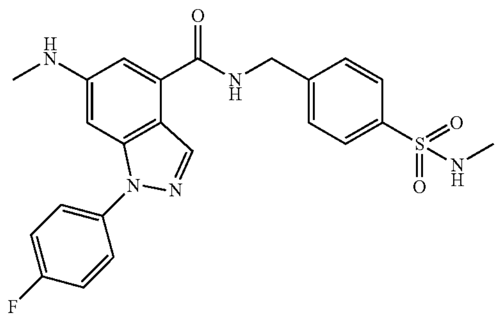 | 1-(4-Fluoro-phenyl)-6-methylamino-1H-indazole-4-carboxylic acid 4-methylsulfamoyl-benzylamide | 468.7 |
| 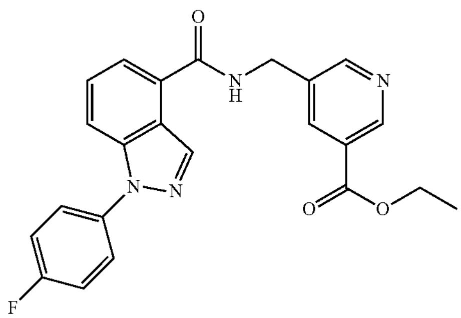 | 5-({[1-(4-Fluoro-phenyl)-1H-indazole-4-carbonyl]-amino}-methyl)-nicotinic acid ethyl ester | 419.7 |
| 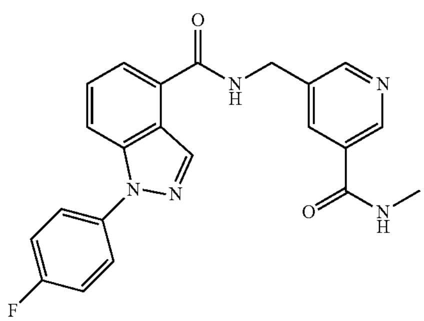 | 1-(4-Fluoro-phenyl)-1H-indazole-4-carboxylic acid (5-methylcarbamoyl-pyridin-3-ylmethyl)-amide | 404.7 |
| 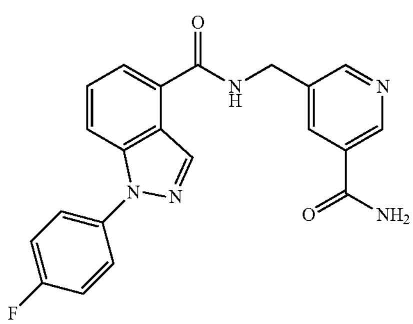 | 1-(4-Fluoro-phenyl)-1H-indazole-4-carboxylic acid (5-carbamoyl-pyridin-3-ylmethyl)-amide | 390.7 |
| 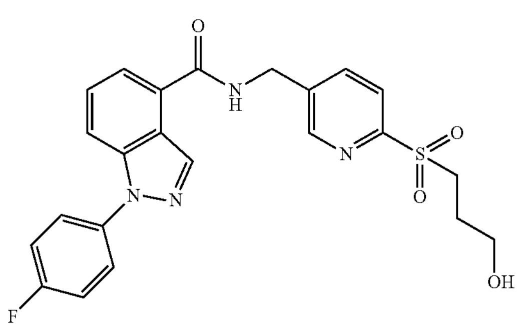 | 1-(4-Fluoro-phenyl)-1H-indazole-4-carboxylic acid [6-(3-hydroxy-propane-1-sulfonyl)-pyridin-3-ylmethyl]-amide | 469.7 |

TABLE I-continued

| STRUCTURE | Name | Observed [M + H]+ |
|---|---|---|
| 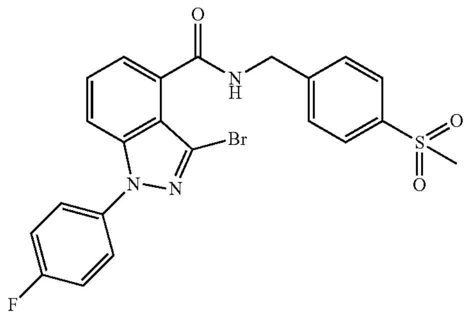 | 3-Bromo-1-(4-fluoro-phenyl)-1H-indazole-4-carboxylic acid 4-methanesulfonyl-benzylamide | 504.6 |
| 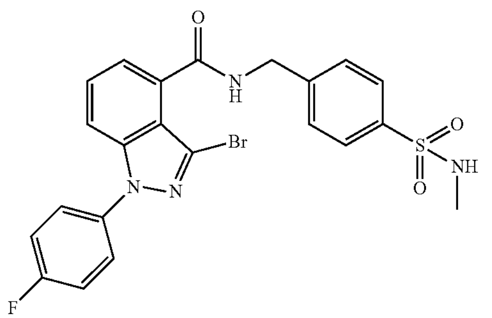 | 3-Bromo-1-(4-fluoro-phenyl)-1H-indazole-4-carboxylic acid 4-methylsulfamoyl-benzylamide | 519.6 |
| 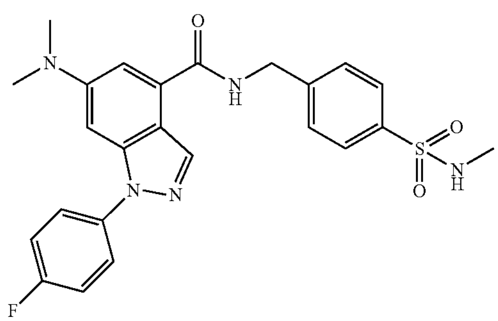 | 6-Dimethylamino-1-(4-fluoro-phenyl)-1H-indazole-4-carboxylic acid 4-methylsulfamoyl-benzylamide | 482.0 |
| 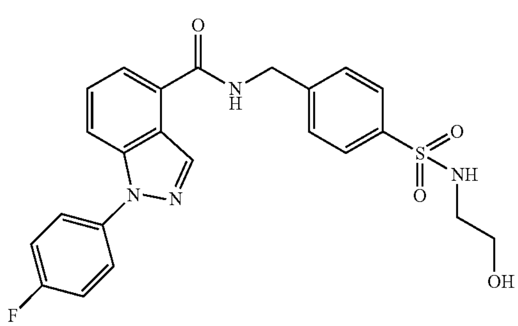 | 1-(4-Fluoro-phenyl)-1H-indazole-4-carboxylic acid 4-(2-hydroxy-ethylsulfamoyl)-benzylamide | 469.7 |

TABLE I-continued

| STRUCTURE | Name | Observed [M + H]+ |
|---|---|---|
| 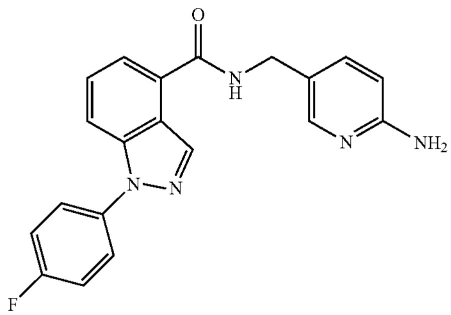 | 1-(4-Fluoro-phenyl)-1H-indazole-4-carboxylic acid (6-amino-pyridin-3-ylmethyl)-amide | 362.7 |
| 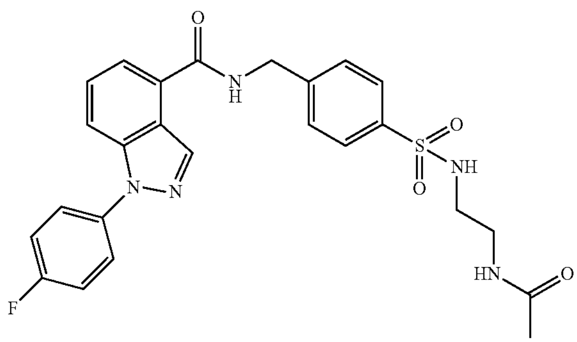 | 1-(4-Fluoro-phenyl)-1H-indazole-4-carboxylic acid 4-(2-acetylamino-ethylsulfamoyl)-benzylamide | 510.8 |
| 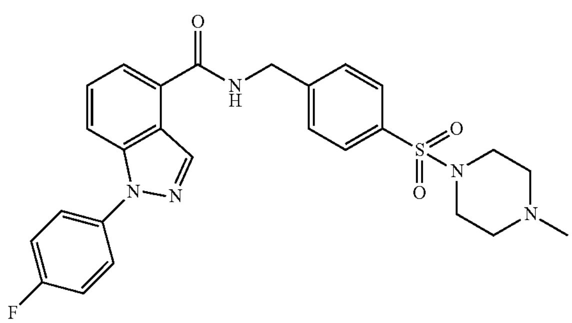 | 1-(4-Fluoro-phenyl)-1H-indazole-4-carboxylic acid 4-(4-methyl-piperazine-1-sulfonyl)-benzylamide | 508.8 |
| 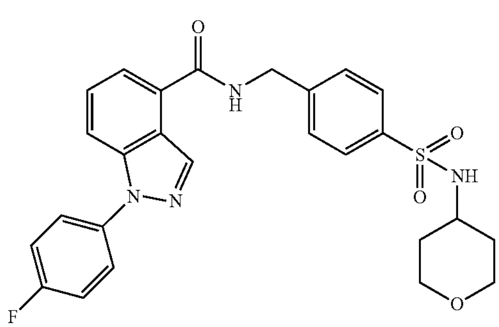 | 1-(4-Fluoro-phenyl)-1H-indazole-4-carboxylic acid 4-(tetrahydro-pyran-4-ylsulfamoyl)-benzylamide | 509.8 |

TABLE I-continued

| STRUCTURE | Name | Observed [M + H]+ |
|---|---|---|
| 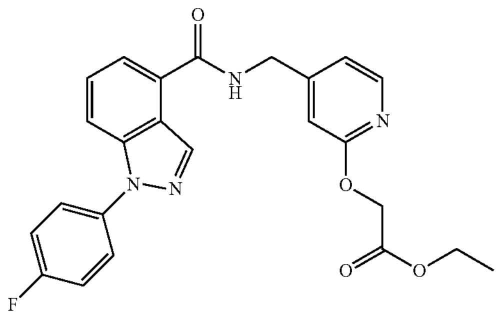 | [4-({[1-(4-Fluoro-phenyl)-1H-indazole-4-carbonyl]-amino}-methyl)-pyridin-2-yloxy]-acetic acid ethyl ester | 449.5 |
| 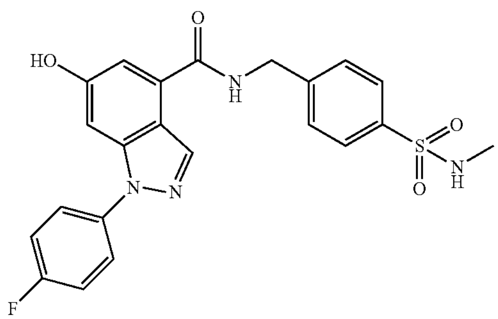 | 1-(4-Fluoro-phenyl)-6-hydroxy-1H-indazole-4-carboxylic acid 4-methylsulfamoyl-benzylamide | 454.7 |
| 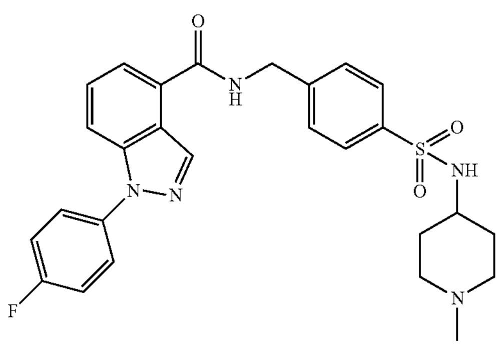 | 1-(4-Fluoro-phenyl)-1H-indazole-4-carboxylic acid 4-(1-methyl-piperidin-4-ylsulfamoyl)-benzylamide | 522.8 |
| 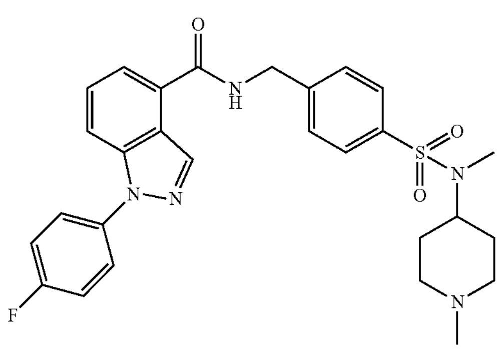 | 1-(4-Fluoro-phenyl)-1H-indazole-4-carboxylic acid 4-[methyl-(1-methyl-piperidin-4-yl)-sulfamoyl]-benzylamide | 536.6 |

TABLE I-continued

| STRUCTURE | Name | Observed [M + H]+ |
|---|---|---|
| 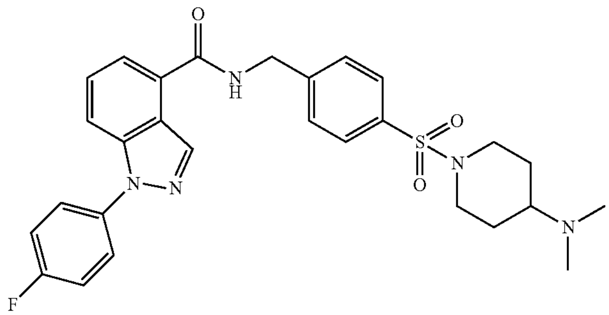 | 1-(4-Fluoro-phenyl)-1H-indazole-4-carboxylic acid 4-(4-dimethylamino-piperidine-1-sulfonyl)-benzylamide | 536.6 |
| 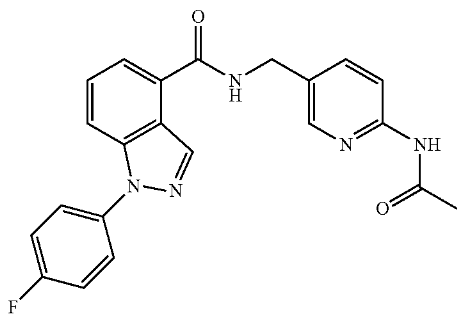 | 1-(4-Fluoro-phenyl)-1H-indazole-4-carboxylic acid (6-acetylamino-pyridin-3-ylmethyl)-amide | 404.7 |
| 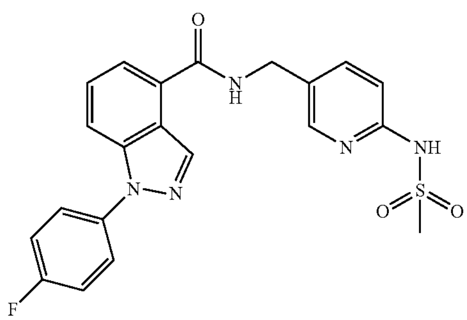 | 1-(4-Fluoro-phenyl)-1H-indazole-4-carboxylic acid (6-methanesulfonylamino-pyridin-3-ylmethyl)-amide | 440.7 |
| 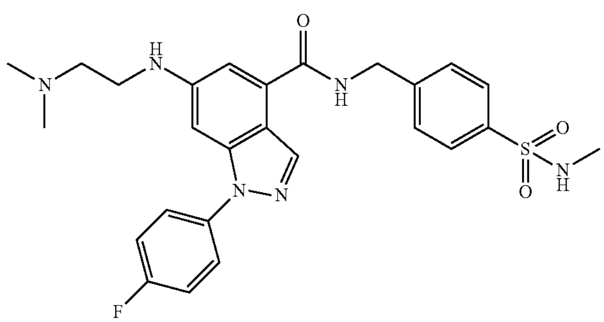 | 6-(2-Dimethylamino-ethylamino)-1-(4-fluoro-phenyl)-1H-indazole-4-carboxylic acid 4-methylsulfamoyl-benzylamide | 524.8 |
| 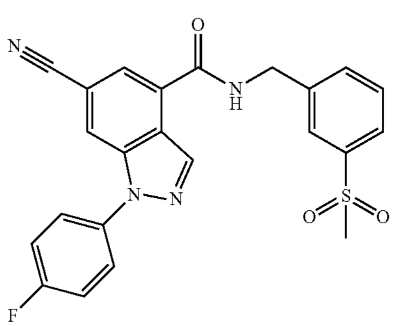 | 6-Cyano-1-(4-fluoro-phenyl)-1H-indazole-4-carboxylic acid 3-methanesulfonyl-benzylamide | 449.7 |

TABLE I-continued

| STRUCTURE | Name | Observed [M + H]+ |
|---|---|---|
| 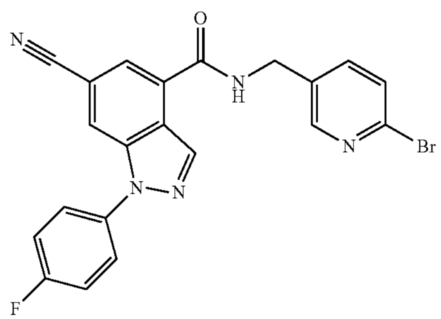 | 6-Cyano-1-(4-fluoro-phenyl)-1H-indazole-4-carboxylic acid (6-bromo-pyridin-3-ylmethyl)-amide | 449.7 |
| 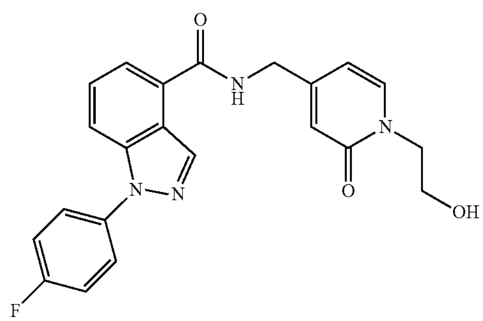 | 1-(4-Fluoro-phenyl)-1H-indazole-4-carboxylic acid [1-(2-hydroxy-ethyl)-2-oxo-1,2-dihydro-pyridin-4-ylmethyl]-amide | 407.7 |
| 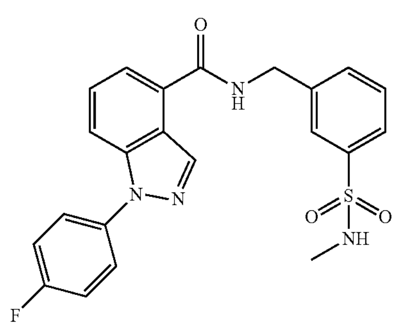 | 1-(4-Fluoro-phenyl)-1H-indazole-4-carboxylic acid 3-methylsulfamoyl-benzylamide | 439.5 |
| 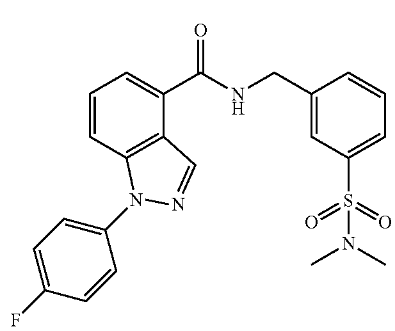 | 1-(4-Fluoro-phenyl)-1H-indazole-4-carboxylic acid 3-dimethylsulfamoyl-benzylamide | 453.5 |

TABLE I-continued

| STRUCTURE | Name | Observed [M + H]+ |
|---|---|---|
| 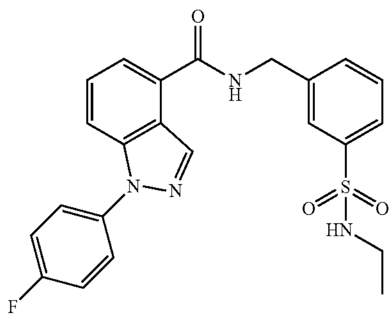 | 1-(4-Fluoro-phenyl)-1H-indazole-4-carboxylic acid 3-ethylsulfamoyl-benzylamide | 453.7 |
| 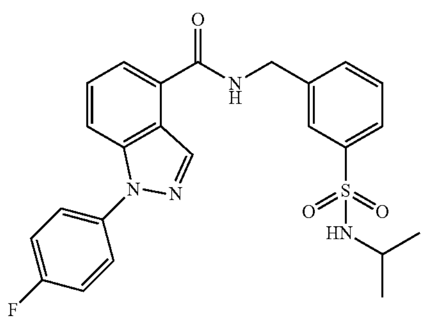 | 1-(4-Fluoro-phenyl)-1H-indazole-4-carboxylic acid 3-isopropylsulfamoyl-benzylamide | 467.7 |
| 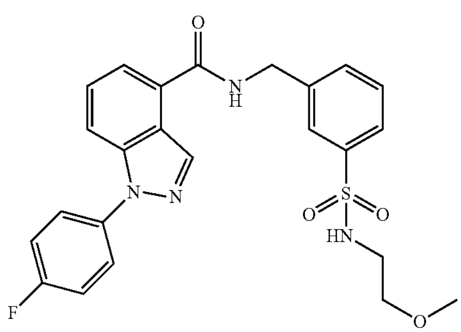 | 1-(4-Fluoro-phenyl)-1H-indazole-4-carboxylic acid 3-(2-methoxy-ethylsulfamoyl)-benzylamide | 483.7 |
| 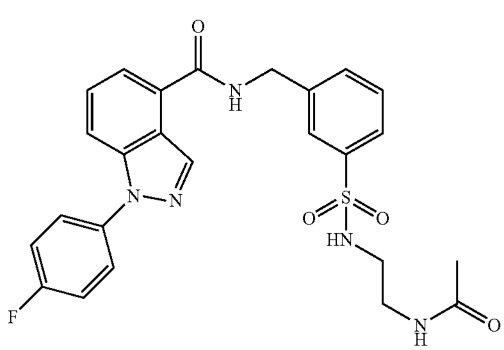 | 1-(4-Fluoro-phenyl)-1H-indazole-4-carboxylic acid 3-(2-acetylamino-ethylsulfamoyl)-benzylamide | 510.7 |

TABLE I-continued

| STRUCTURE | Name | Observed [M + H]+ |
|---|---|---|
| 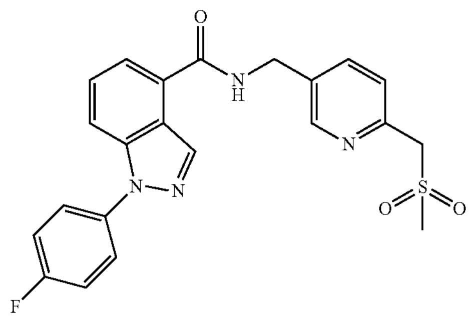 | 1-(4-Fluoro-phenyl)-1H-indazole-4-carboxylic acid (6-methanesulfonylmethyl-pyridin-3-ylmethyl)-amide | 439.7 |
| 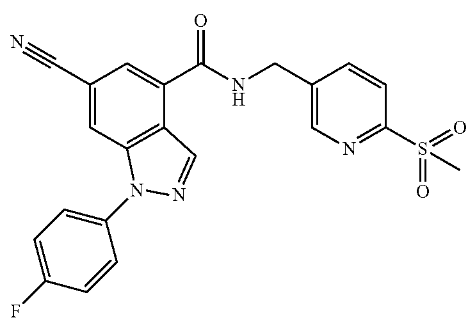 | 6-Cyano-1-(4-fluoro-phenyl)-1H-indazole-4-carboxylic acid (6-methanesulfonyl-pyridin-3-ylmethyl)-amide | 449.7 |
| 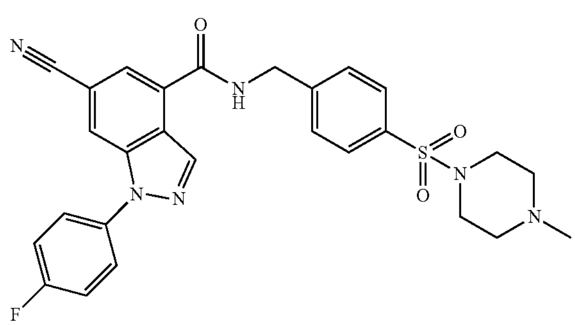 | 6-Cyano-1-(4-fluoro-phenyl)-1H-indazole-4-carboxylic acid 4-(4-methyl-piperazine-1-sulfonyl)-benzylamide | 532.8 |
| 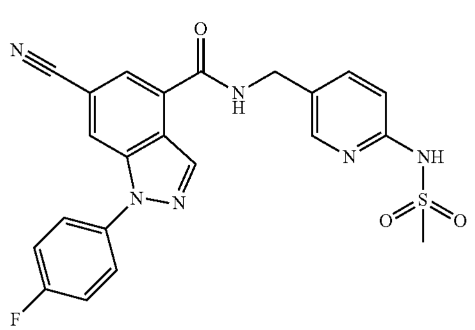 | 6-Cyano-1-(4-fluoro-phenyl)-1H-indazole-4-carboxylic acid (6-methanesulfonylamino-pyridin-3-ylmethyl)-amide | 465.1 |

TABLE I-continued

| STRUCTURE | Name | Observed [M + H]+ |
|---|---|---|
| 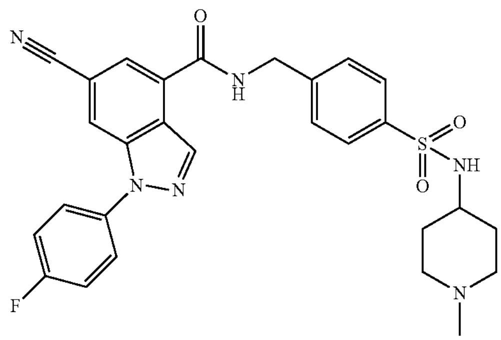 | 6-Cyano-1-(4-fluoro-phenyl)-1H-indazole-4-carboxylic acid 4-(1-methyl-piperidin-4-ylsulfamoyl)-benzylamide | 547.8 |
| 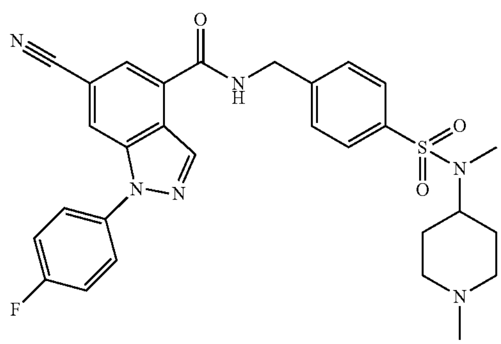 | 6-Cyano-1-(4-fluoro-phenyl)-1H-indazole-4-carboxylic acid 4-[methyl-(1-methyl-piperidin-4-yl)-sulfamoyl]-benzylamide | 560.9 |
| 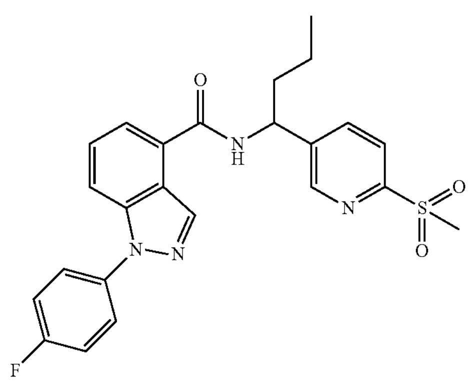 | 1-(4-Fluoro-phenyl)-1H-indazole-4-carboxylic acid [1-(6-methanesulfonyl-pyridin-3-yl)-butyl]-amide | 467.6 |
| 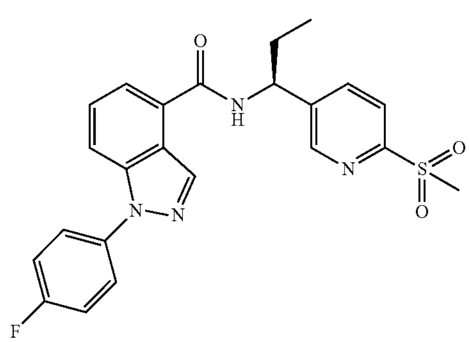 | 1-(4-Fluoro-phenyl)-1H-indazole-4-carboxylic acid [(S)-1-(6-methanesulfonyl-pyridin-3-yl)-propyl]-amide | 453.6 |

TABLE I-continued

| STRUCTURE | Name | Observed [M + H]+ |
|---|---|---|
| 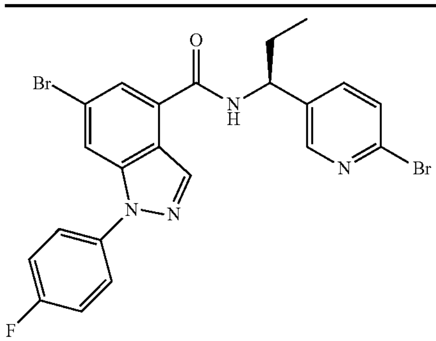 | 6-Bromo-1-(4-fluoro-phenyl)-1H-indazole-4-carboxylic acid [(S)-1-(6-bromo-pyridin-3-yl)-propyl]-amide | M = 532.6 |
| 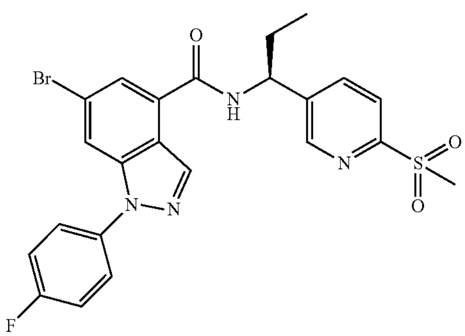 | 6-Bromo-1-(4-fluoro-phenyl)-1H-indazole-4-carboxylic acid [(S)-1-(6-methanesulfonyl-pyridin-3-yl)-propyl]-amide | 530.9/532.7 |
| | 1-(4-Fluoro-phenyl)-6-methanesulfonyl-1H-indazole-4-carboxylic acid [(S)-1-(6-methanesulfonyl-pyridin-3-yl)-propyl]-amide | [M] = 530.7 | or the pharmaceutically acceptable salts thereof.

For all compounds disclosed hereinabove in this application, in the event the nomenclature is in conflict with the structure, it shall be understood that the compound is defined by the structure.

The invention also relates to pharmaceutical preparations, containing as an active substance one or more compounds of the invention, or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}O$, $^{17}O$, $^{31}P$, $^{32}F$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of the invention can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocycles include hydrocarbon rings containing from three to twelve carbon atoms. These carbocycles may be either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 4-8 membered (but preferably, 5 or 6 membered) monocyclic or nonaromatic 8-11 membered bicyclic or spirocyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure.

The term "heteroaryl" shall be understood to mean an aromatic 5-8 membered monocyclic or 8-11 membered bicyclic ring containing 1-4 heteroatoms such as N, O and S.

Unless otherwise stated, heterocycles and heteroaryl include but are not limited to, for example furanyl, pyranyl, benzoxazolyl, benzothiazolyl, benzimidazolyl, tetrahydropyranyl, dioxanyl, tetrahydrofuranyl, oxazolyl, isoxazolyl, thiazolyl, pyrazolyl, pyrrolyl, imidazolyl, thienyl, thiadiazolyl, thiomorpholinyl, 1,1-dioxo-1$\lambda^6$-thiomorpholinyl, morpholinyl, pyridinyl, pyrimidinyl, pyridazinyl, pyrazinyl, triazinyl, pyrrolidinyl, piperidinyl, piperazinyl, purinyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl and benzodioxolyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein shall be understood to mean aromatic carbocycle or heteroaryl as defined herein. Each aryl or heteroaryl unless otherwise specified includes it's partially or fully hydrogenated derivative. For example, quinolinyl may include decahydroquinolinyl and tetrahydroquinolinyl, naphthyl may include its hydrogenated derivatives such as tetrahydranaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "alkyl" refers to a saturated aliphatic radical containing from one to ten carbon atoms or a mono- or polyunsaturated aliphatic hydrocarbon radical containing from two to twelve carbon atoms. The mono- or polyunsaturated aliphatic hydrocarbon radical containing at least one double or triple bond, respectively. "Alkyl" refers to both branched and unbranched alkyl groups. It should be understood that any combination term using an "alk" or "alkyl" prefix refers to analogs according to the above definition of "alkyl". For example, terms such as "alkoxy", "alkythio" refer to alkyl groups linked to a second group via an oxygen or sulfur atom. "Alkanoyl" refers to an alkyl group linked to a carbonyl group (C=O).

The term "halogen" as used in the present specification shall be understood to mean bromine, chlorine, fluorine or iodine, preferably fluorine. The definitions "halogenated", "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

Each alkyl, carbocycle, heterocycle or heteroaryl, or the analogs thereof, described herein shall be understood to be optionally partially or fully halogenated.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the invention.

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—($C_1$-$C_4$ alkyl)$_4^+$ salts.

In addition, within the scope of the invention is use of prodrugs of compounds of the invention. Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described below, which also constitute part of the invention.

General Synthetic Methods

The invention additionally provides for methods for making compounds of formula I. The compounds of the invention may be prepared by the general methods and examples presented below, and methods known to those of ordinary skill in the art and reported in the chemical literature. Unless otherwise specified, solvents, temperatures, pressures, and other reaction conditions may be readily selected by one of ordinary skill in the art. Specific procedures are provided in the Synthetic Examples section. Intermediate benzyl amines are commercially available, or may be synthesized via catalytic reduction of the corresponding aryl nitriles with Pd/C (Van Rompaey, K. et al, Tetrahedron, 2003, 59 (24), 4421) or Raney Ni (Gould, F. et al, J. Org. Chem., 1960, 25, 1658) or through displacement of a benzyl bromide with sodium azide and reduction (see example 2 below). Intermediate chiral and racemic aminomethylpyridines may also be commercially available or prepared by methods known to those skilled in the art. For example, methods of preparing 1-substituted-1-pyridylmethylamines from aldehydes or ketones are known (see, Kuduk, S. D. et al, Tetrahedron Lett., 2004, 45, 6641 and Chelucci, G. Tetrahedron: Asymmetry 2006, 17, 3163). Amide bond formations may be carried out by standard coupling conditions well-known in the art (see, for example, M. Bodanszky, *The Practice of Peptide Synthesis* (Springer-Verlag: 1984), which is hereby incorporated by reference in its entirety), for example, by reacting a carboxylic acid and an amine in the presence of 1-(3-dimethylaminopropyl)-3-ethylcarbodiimide (EDC) and 1-hydroxybenzotriazole. Reaction progress may be monitored by conventional methods such as thin layer chromatography (TLC). Intermediates and products may be purified by methods known in the art, including column chromatography, HPLC or recrystallization.

The methods described below and in the Synthetic Examples section may be used to prepare the compounds of formula I. In the schemes below, $Ar_1$, $R_1$-$R_5$, $X_1$ and $X_2$ shall have the meanings defined in the detailed description of formula I.

Compounds of formula I may be prepared as shown in Scheme I.

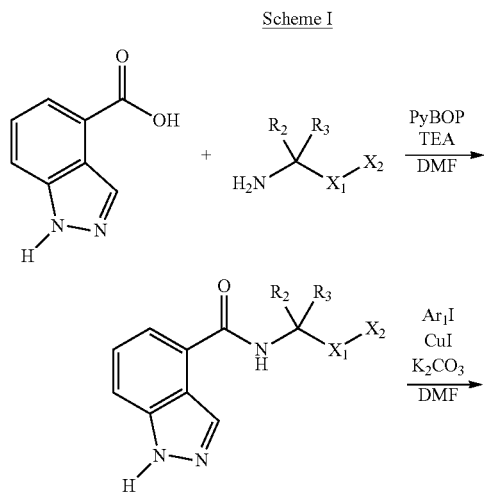

Scheme I

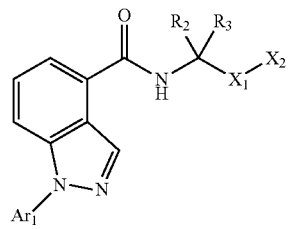

An indazole-4-carboxylic acid is coupled to the desired amine using standard coupling amide conditions, for example by treatment with (benzotriazole-1-yloxy)tripyrrolidinophosphonium hexafluorophosphate (PyBOP) and triethylamine in a suitable solvent such as DMF. The resultant indazole-4-carboxamide is then treated with the desired $Ar_1I$ ($Ar_1$=optionally substituted aryl or heteroaryl) in the presence of CuI, $K_2CO_3$, and an amine ligand (such as racemic trans-N,N'-dimethylcyclohexane-1,2-diamine) in a suitable solvent such as DMF to form the compound of formula I.

Another approach that may be used to obtain compounds of formula I is illustrated in Scheme II.

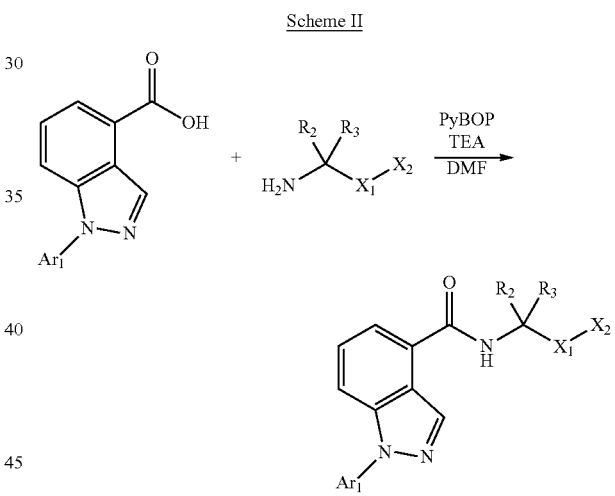

Scheme II

In this method, a 1-substituted-1H-indazole-4-carboxylic acid is treated with the desired amine under standard amide coupling conditions, such as treatment with PyBOP, TEA or treatment with HATU to afford the desired compound of formula I. Alternatively, the 1-substituted-1H-indazole-4-carboxylic may be converted in situ to the corresponding acid chloride, for example, by treatment with oxalyl chloride in dichloromethane or with neat thionyl chloride. The crude acid chloride was concentrated in vacuo and treated with the desired amine in the presence of an amine base such as triethylamine (TEA) or N,N-diisopropylethylamine (DIEA) in a suitable solvent such as dichloromethane (DCM) to form the compound of formula I.

Compounds of formula I prepared by the above methods may be further converted to additional compounds of formula I by methods known in the art and exemplified in the Synthetic Examples section below.

SYNTHETIC EXAMPLES

Example 1

Synthesis of 1-(4-Fluorophenyl)-1H-indazole-4-carboxylic acid 3-trifluoromethyl-benzylamide (1)

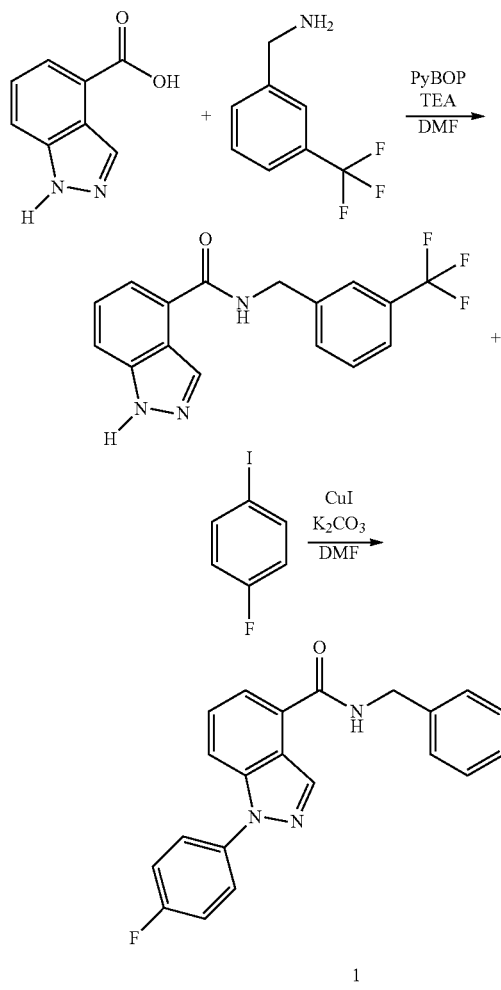

To a stirred room temperature solution of indazole-4-carboxylic acid (1.0 g, 6.1 mmol) in DMF (15 mL) was added PyBOP (3.5 g, 6.5 mmol) and triethylamine (0.90 g, 7.5 mmol). After 15 minutes, 3-trifluoromethyl-benzylamine (1.2 g, 7.0 mmol) was added. After 4 hours, the mixture was quenched with water (30 mL) and diluted with ethyl acetate (20 mL). The organic layer was separated, washed with brine (30 mL), dried over sodium sulfate and concentrated in vacuo. The residue was purified by silica gel chromatography eluting with a gradient of 20-60% ethyl acetate in hexanes to afford 1H-indazole-4-carboxylic acid 3-trifluoromethyl-benzylamide.

A mixture of 1H-indazole-4-carboxylic acid 3-trifluoromethyl-benzylamide (1.1 g, 3.4 mmol), copper(I) iodide (0.005 g, 0.02 mmol), potassium carbonate (0.04 g, 0.3 mmol) and 4-fluoroiodobenzene (0.04 g, 0.2 mmol) were charged in a sealed tube at room temperature. The tube was evacuated and back-filled with argon. The solids were dissolved in DMF (6 mL) and the resultant solution was treated with rac-trans-N, N'-dimethylcyclohexane-1,2-diamine (0.005 g, 0.04 mmol). The solution was stirred at 120° C. for 3 hours and cooled to room temperature. The solution was diluted with water (15 mL) and ethyl acetate (30 mL). The organic layer was separated, washed with brine and dried over sodium sulfate. The solvent was removed in vacuo. The crude residue was purified by silica gel chromatography eluting with a gradient of 10-40% ethyl acetate in hexanes to afford the title compound.

The following compounds were also prepared by methods described in Example 1:

1-(3,4-Dichloro-phenyl)-1H-indazole-4-carboxylic acid 3-trifluoromethyl benzylamide,
1-(3,4-Dichloro-phenyl)-1H-indazole-4-carboxylic acid [(S)-1-(3-trifluoromethyl-phenyl)-ethyl]-amide,
1-(3,4-Dichloro-phenyl)-1H-indazole-4-carboxylic acid [(R)-1-(3-trifluoromethyl-phenyl)-ethyl]-amide,
1-p-Tolyl-1H-indazole-4-carboxylic acid 3-trifluoromethyl-benzylamide,
1-Phenyl-1H-indazole-4-carboxylic acid 3-trifluoromethyl-benzylamide,
1-(3,4-Dichloro-phenyl)-1H-indazole-4-carboxylic acid phenethyl-amide,
1-(2-Methoxy-phenyl)-1H-indazole-4-carboxylic acid 3-trifluoromethyl-benzylamide,
1-(3,4-Dichloro-phenyl)-1H-indazole-4-carboxylic acid [2-(3-fluoro-phenyl)-ethyl]-amide,
1-(3,4-Dichloro-phenyl)-1H-indazole-4-carboxylic acid [1-(3-trifluoromethyl-phenyl)-ethyl]-amide,
1-(3,4-Dichloro-phenyl)-1H-indazole-4-carboxylic acid (1-phenyl-ethyl)-amide,
1-o-Tolyl-1H-indazole-4-carboxylic acid 3-trifluoromethyl-benzylamide,
1-m-Tolyl-1H-indazole-4-carboxylic acid 3-trifluoromethyl-benzylamide,
1-(2-Cyano-phenyl)-1H-indazole-4-carboxylic acid 3-trifluoromethyl-benzylamide,
1-Pyridin-3-yl-1H-indazole-4-carboxylic acid 3-trifluoromethyl-benzylamide,
1-Pyridin-2-yl-1H-indazole-4-carboxylic acid 3-trifluoromethyl-benzylamide,
1-(2-Fluoro-phenyl)-1H-indazole-4-carboxylic acid 3-trifluoromethyl-benzylamide,
1-(3-Fluoro-phenyl)-1H-indazole-4-carboxylic acid 3-trifluoromethyl-benzylamide,
1-(4-Fluoro-phenyl)-1H-indazole-4-carboxylic acid 3-trifluoromethyl-benzylamide,
1-Pyridin-4-yl-1H-indazole-4-carboxylic acid 3-trifluoromethyl-benzylamide,
1-(3,4-Dichloro-phenyl)-1H-indazole-4-carboxylic acid [2-(3-trifluoromethyl-phenyl)-ethyl]-amide,
1-(3,4-Difluoro-benzyl)-1H-indazole-4-carboxylic acid 3-trifluoromethyl-benzylamide,
1-Thiophen-2-yl-1H-indazole-4-carboxylic acid 3-trifluoromethyl-benzylamide,
1-Thiophen-3-yl-1H-indazole-4-carboxylic acid 3-trifluoromethyl-benzylamide,
1-(3-Chloro-4-fluoro-benzyl)-1H-indazole-4-carboxylic acid 3-trifluoromethyl-benzylamide,
1-(2,4-Difluoro-benzyl)-1H-indazole-4-carboxylic acid 3-trifluoromethyl-benzylamide,
1-(4-Fluoro-2-methyl-benzyl)-1H-indazole-4-carboxylic acid 3-trifluoromethyl-benzylamide,
1-(6-Fluoro-pyridin-3-yl)-1H-indazole-4-carboxylic acid 3-trifluoromethyl-benzylamide,
1-(4-Fluoro-3-methyl-benzyl)-1H-indazole-4-carboxylic acid 3-trifluoromethyl-benzylamide, and 1-(4-Chloro-benzyl)-1H-indazole-4-carboxylic acid 3-trifluoromethyl-benzylamide.

Example 2

Synthesis of 1-(4-Fluoro-phenyl)-1H-indazole-4-carboxylic acid 4-methylsulfamoyl-benzylamide (2)

a) 1-(4-Fluoro-phenyl)-1H-indazole-4-carboxylic acid

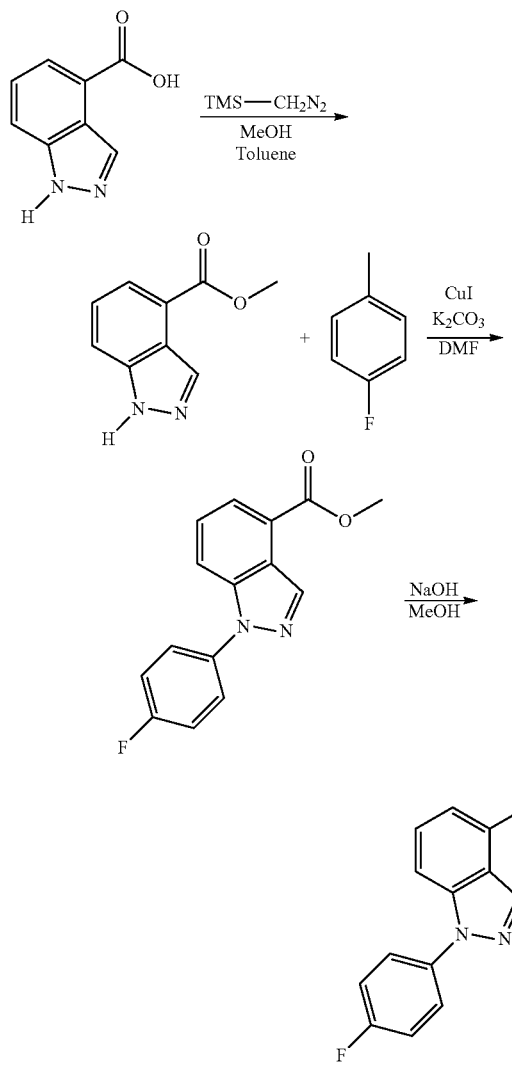

Indazole-4-carboxylic acid (2.00 g, 12.3 mmol) was suspended in methanol (20 mL) and toluene (30 mL) at room temperature. A solution of 2 M trimethylsilyl diazomethane (12 mL, 24 mmol) in toluene was added slowly and the mixture was stirred at room temperature until the solution turned yellow. The reaction was quenched with concentrated acetic acid (5 mL) and the solvent was removed in vacuo. The residue was purified by silica gel chromatography eluting with a gradient of 0-30% ethyl acetate in hexanes to afford 1H-indazole-4-carboxylic acid methyl ester.

A mixture of 1H-indazole-4-carboxylic acid methyl ester (5.0 g, 28 mmol), copper(I) iodide (5.7 g, 3.0 mmol), potassium carbonate (4.15 g, 30.0 mmol) and 4-fluoroiodobenzene (3.47 g, 30.0 mmol) was charged in a sealed tube at room temperature. The tube was evacuated, back-filled with argon and dimethylformamide (20 mL) was added followed by rac-trans-N,N'-dimethylcyclohexane-1,2-diamine (0.93 g, 6.5 mmol). The solution was stirred at 120° C. for 3 hours. The solution was cooled to room temperature and diluted with water (50 mL) and ethyl acetate (80 mL). The organic layer was separated, washed with brine (30 mL), and dried over sodium sulfate. The crude product was filtered, concentrated and purified by silica gel chromatography eluting with a gradient of 0-30% ethyl acetate in hexanes to afford 1-(4-fluoro-phenyl)-1H-indazole-4-carboxylic acid methyl ester.

To a stirred solution of 1-(4-fluoro-phenyl)-1H-indazole-4-carboxylic acid methyl ester (2.0 g, 7.4 mmol) in water (20 mL) and methanol (20 mL) was added a solution of 2 N sodium hydroxide (10 mL). The solution was warmed at reflux for 1 hour. The solution was cooled to room temperature and acidified with 1 N aqueous HCl (pH=3-4). The white solid was obtained by filtration, washed with MeOH (30 mL) and dried to afford 1-(4-fluoro-phenyl)-1H-indazole-4-carboxylic acid.

b) 4-Aminomethyl-N-methyl-benzenesulfonamide

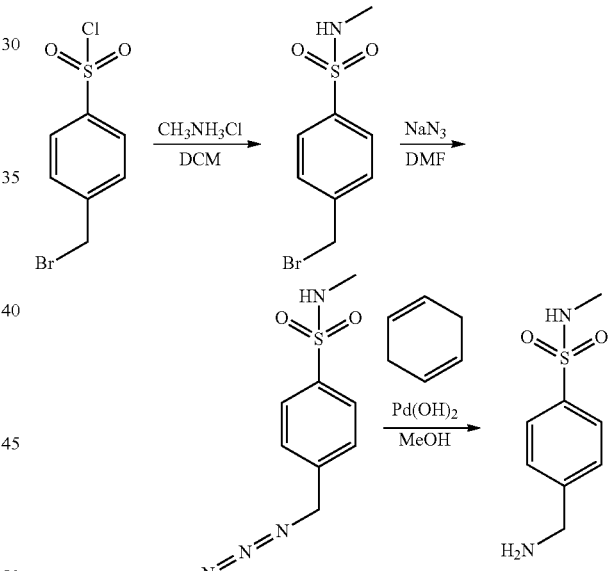

To a chilled (0° C.) stirred solution of 4-(bromomethyl)-benzenesulfonylchloride (3.0 g, 11 mmol) in DCM (100 mL) was added methylamine hydrochloride (1.2 g, 12 mmol). After 30 minutes, water (100 mL) was added. The organic layer was separated, washed with brine (30 mL), and dried over sodium sulfate and concentrated in vacuo to afford 4-bromomethyl-N-methyl-benzenesulfonamide.

To a stirred room temperature solution of 4-bromomethyl-N-methyl-benzenesulfonamide (2.70 g, 10.0 mmol) in DMF (15 mL) was added sodium azide (0.90 g, 13 mmol). The mixture was stirred at 40° C. for 16 hours. The solution was poured into water (60 mL) and diluted with ethyl acetate (100 mL). The organic layer was separated and washed with brine (30 mL), dried over sodium sulfate and concentrated in vacuo to afford 4-azidomethyl-N-methyl-benzenesulfonamide A mixture of 4-azidomethyl-N-methyl-benzenesulfonamide (2.20 g, 10.0 mmol), cyclohexadiene (8.90 mL, 90.0 mmol) and palladium hydroxide (20% on carbon, 1.4 g, 2.0 mmol) in MeOH (20 mL) was warmed at 65° C. for 2 hours. The solution was cooled to room temperature and filtered through diatomaceous earth. The solvent was removed in vacuo to afford 4-aminomethyl-N-methyl-benzenesulfonamide c) 1-(4-Fluoro-phenyl)-1H-indazole-4-carboxylic acid 4-methylsulfamoyl-benzylamide

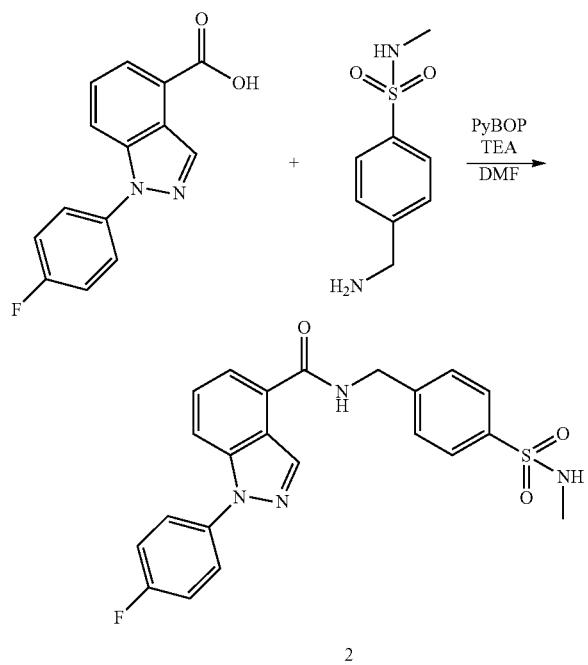

To a stirred solution of 1-(4-fluoro-phenyl)-1H-indazole-4-carboxylic acid (0.05 g, 0.2 mmol) in DMF (10 mL) was added PyBOP (0.14 g, 0.30 mmol) and triethylamine (0.07 g, 0.6 mmol) at room temperature. After 15 minutes, 4-aminomethyl-N-methyl-benzenesulfonamide (0.04 g, 0.2 mmol) was added. After 5 hours, the mixture was quenched with water (30 mL) and diluted with ethyl acetate (30 mL). The organic layer was separated, washed with brine (30 mL), dried over sodium sulfate, filtered and concentrated. The residue was purified by silica gel chromatography eluting with a gradient of 0-30% ethyl acetate in hexanes to afford the title compound.

The following compounds were also prepared by methods described in Example 2:
1-(4-Fluoro-phenyl)-1H-indazole-4-carboxylic acid 4-bromo-2-chloro-benzylamide,
1-(4-Fluoro-phenyl)-1H-indazole-4-carboxylic acid 4-iodo-benzylamide,
1-(4-Fluoro-phenyl)-1H-indazole-4-carboxylic acid 2-fluoro-4-methylsulfamoyl-benzylamide,
1-(4-Fluoro-phenyl)-1H-indazole-4-carboxylic acid (2-cyano-pyridin-4-ylmethyl)-amide,
1-(4-Fluoro-phenyl)-1H-indazole-4-carboxylic acid (6-bromo-pyridin-3-ylmethyl)-amide,
1-(4-Fluoro-phenyl)-1H-indazole-4-carboxylic acid (6-cyano-pyridin-3-ylmethyl)-amide,
4-({[1-(4-Fluoro-phenyl)-1H-indazole-4-carbonyl]-amino}-methyl)-pyridine-2-carboxylic acid methyl ester,
1-(4-Fluoro-phenyl)-1H-indazole-4-carboxylic acid 4-methylsulfamoyl-benzylamide,
1-(4-Fluoro-phenyl)-1H-indazole-4-carboxylic acid 4-(morpholine-4-sulfonyl)-benzylamide,
1-(4-Fluoro-phenyl)-1H-indazole-4-carboxylic acid 4-dimethylsulfamoyl-benzylamide,
1-(4-Fluoro-phenyl)-1H-indazole-4-carboxylic acid 4-isopropylsulfamoyl-benzylamide,
1-(4-Fluoro-phenyl)-1H-indazole-4-carboxylic acid 4-(2-methoxy-ethylsulfamoyl)-benzylamide,
1-(4-Fluoro-phenyl)-1H-indazole-4-carboxylic acid 2-methanesulfonyl-benzylamide,
1-(4-Fluoro-phenyl)-1H-indazole-4-carboxylic acid 4-methylsulfamoylmethyl-benzylamide,
1-(4-Fluoro-phenyl)-1H-indazole-4-carboxylic acid 4-(isopropylsulfamoyl-methyl)-benzylamide,
1-(4-Fluoro-phenyl)-1H-indazole-4-carboxylic acid 4-(2-dimethylamino-ethylsulfamoyl)-benzylamide,
1-(4-Fluoro-phenyl)-1H-indazole-4-carboxylic acid 4-(2-acetylamino-ethylsulfamoyl)-benzylamide,
1-(4-Fluoro-phenyl)-1H-indazole-4-carboxylic acid 4-(4-methyl-piperazine-1-sulfonyl)-benzylamide,
1-(4-Fluoro-phenyl)-1H-indazole-4-carboxylic acid 4-(tetrahydro-pyran-4-ylsulfamoyl)-benzylamide,
1-(4-Fluoro-phenyl)-1H-indazole-4-carboxylic acid 4-(1-methyl-piperidin-4-ylsulfamoyl)-benzylamide,
1-(4-Fluoro-phenyl)-1H-indazole-4-carboxylic acid 4-[methyl-(1-methyl-piperidin-4-yl)-sulfamoyl]-benzylamide,
1-(4-Fluoro-phenyl)-1H-indazole-4-carboxylic acid 4-(4-dimethylamino-piperidine-1-sulfonyl)-benzylamide,
1-(4-Fluoro-phenyl)-1H-indazole-4-carboxylic acid 3-ethylsulfamoyl-benzylamide,
1-(4-Fluoro-phenyl)-1H-indazole-4-carboxylic acid 3-isopropylsulfamoyl-benzylamide,
1-(4-Fluoro-phenyl)-1H-indazole-4-carboxylic acid 3-(2-methoxy-ethylsulfamoyl)-benzylamide,
1-(4-Fluoro-phenyl)-1H-indazole-4-carboxylic acid 3-(2-acetylamino-ethylsulfamoyl)-benzylamide, and
1-(4-Fluoro-phenyl)-1H-indazole-4-carboxylic acid [1-(6-methanesulfonyl-pyridin-3-yl)-butyl]-amide.

Example 3

Synthesis of 1-(4-Fluoro-phenyl)-1H-indazole-4-carboxylic acid (1-naphthalen-1-yl-ethyl)-amide (3)

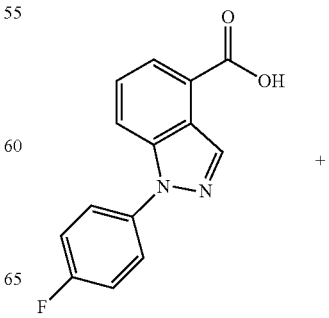

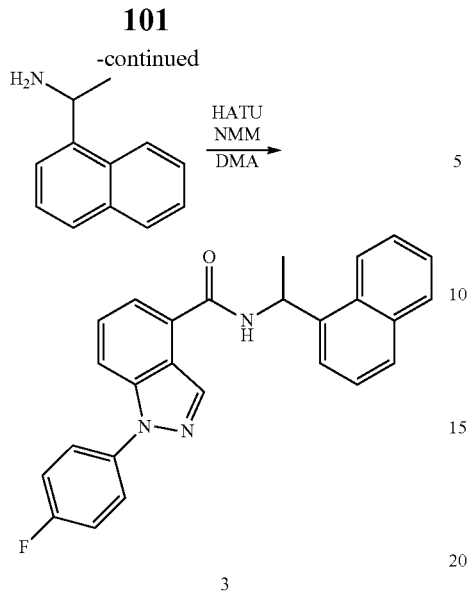

1-(4-Fluoro-phenyl)-1H-indazole-4-carboxylic acid (40.0 mg, 0.156 mmol) and O-(7-azabenzotriazole-1-yl)-N,N,N', N'-tetramethyluronium hexafluorophosphate (HATU) (89 mg, 0.23 mmol) were combined in a 20 mL vial and dimethylacetamide (DMA) (1 mL) was added. The yellow solution was stirred at room temperature for 10 minutes and then a solution of 1-(1-napthyl)ethylamine (40.1 mg, 0.234 mmol) and N-methylmorpholine (NMM) (0.086 mL, 0.78 mmol) in DMA (0.20 mL) was added. The mixture was shaken at room temperature for 16 hours then the solution was evaporated in vacuo. The crude product was purified by preparative reversed-phase HPLC to afford the title compound.

The following compounds were also prepared by methods described in Example 3:

1-(4-Fluoro-phenyl)-1H-indazole-4-carboxylic acid (1-naphthalen-1-yl-ethyl)-amide,
1-(4-Fluoro-phenyl)-1H-indazole-4-carboxylic acid (naphthalen-1-ylmethyl)-amide,
1-(4-Fluoro-phenyl)-1H-indazole-4-carboxylic acid (pyridin-2-ylmethyl)-amide,
1-(4-Fluoro-phenyl)-1H-indazole-4-carboxylic acid (pyridin-3-ylmethyl)-amide,
1-(4-Fluoro-phenyl)-1H-indazole-4-carboxylic acid (pyridin-4-ylmethyl)-amide,
1-(4-Fluoro-phenyl)-1H-indazole-4-carboxylic acid 2-methoxy-benzylamide,
1-(4-Fluoro-phenyl)-1H-indazole-4-carboxylic acid 3-methoxy-benzylamide,
1-(4-Fluoro-phenyl)-1H-indazole-4-carboxylic acid 2-trifluoromethyl-benzylamide,
1-(4-Fluoro-phenyl)-1H-indazole-4-carboxylic acid 4-sulfamoyl-benzylamide,
1-(4-Fluoro-phenyl)-1H-indazole-4-carboxylic acid 2-bromo-benzylamide,
1-(4-Fluoro-phenyl)-1H-indazole-4-carboxylic acid 3-chloro-benzylamide,
1-(4-Fluoro-phenyl)-1H-indazole-4-carboxylic acid 4-bromo-benzylamide,
1-(4-Fluoro-phenyl)-1H-indazole-4-carboxylic acid 3,5-dimethoxy-benzylamide,
1-(4-Fluoro-phenyl)-1H-indazole-4-carboxylic acid 4-fluoro-3-trifluoromethyl-benzylamide,
1-(4-Fluoro-phenyl)-1H-indazole-4-carboxylic acid 3-dimethylamino-benzylamide,
1-(4-Fluoro-phenyl)-1H-indazole-4-carboxylic acid 4-methanesulfonyl-benzylamide,
1-(4-Fluoro-phenyl)-1H-indazole-4-carboxylic acid (biphenyl-2-ylmethyl)-amide,
1-(4-Fluoro-phenyl)-1H-indazole-4-carboxylic acid 3-bromo-benzylamide,
1-(4-Fluoro-phenyl)-1H-indazole-4-carboxylic acid 3-acetylamino-benzylamide,
1-(4-Fluoro-phenyl)-1H-indazole-4-carboxylic acid 3-(acetyl-methyl-amino)-benzylamide,
1-(4-Fluoro-phenyl)-1H-indazole-4-carboxylic acid 3-methanesulfonyl-benzylamide,
1-(4-Fluoro-phenyl)-1H-indazole-4-carboxylic acid 2-cyano-benzylamide,
1-(4-Fluoro-phenyl)-1H-indazole-4-carboxylic acid 4-fluoro-2-methanesulfonyl-benzylamide,
1-(4-Fluoro-phenyl)-1H-indazole-4-carboxylic acid 2-chloro-4-methylsulfamoyl-benzylamide,
1-(4-Fluoro-phenyl)-1H-indazole-4-carboxylic acid (1-methyl-1-phenyl-ethyl)-amide,
1-(4-Fluoro-phenyl)-1H-indazole-4-carboxylic acid [(S)-1-(3-bromo-phenyl)-butyl]-amide,
1-(4-Fluoro-phenyl)-1H-indazole-4-carboxylic acid [2-(3-methoxy-phenyl)-ethyl]-amide,
4-({[[1-(4-Fluoro-phenyl)-1H-indazole-4-carbonyl]-amino}-methyl)-benzoic acid methyl ester,
1-(4-Fluoro-phenyl)-1H-indazole-4-carboxylic acid 4-trifluoromethylsulfanyl-benzylamide,
1-(4-Fluoro-phenyl)-1H-indazole-4-carboxylic acid [2-(3,5-dimethoxy-phenyl)-ethyl]-amide,
1-(4-Fluoro-phenyl)-1H-indazole-4-carboxylic acid [2-(3,4-dimethoxy-phenyl)-ethyl]-amide,
1-(4-Fluoro-phenyl)-1H-indazole-4-carboxylic acid (1-phenyl-ethyl)-amide,
1-(4-Fluoro-phenyl)-1H-indazole-4-carboxylic acid 3,4-dimethoxy-benzylamide,
1-(4-Fluoro-phenyl)-1H-indazole-4-carboxylic acid [(R)-1-(3-trifluoromethyl-phenyl)-ethyl]-amide,
1-(4-Fluoro-phenyl)-1H-indazole-4-carboxylic acid [1-(3-trifluoromethyl-phenyl)-ethyl]-amide,
1-(4-Fluoro-phenyl)-1H-indazole-4-carboxylic acid 3-methylsulfanyl-benzylamide,
1-(4-Fluoro-phenyl)-1H-indazole-4-carboxylic acid 2-imidazol-1-yl-benzylamide,
1-(4-Fluoro-phenyl)-1H-indazole-4-carboxylic acid 3-dimethylaminomethyl-benzylamide,
1-(4-Fluoro-phenyl)-1H-indazole-4-carboxylic acid 4-methylsulfanyl-benzylamide,
3-({[1-(4-Fluoro-phenyl)-1H-indazole-4-carbonyl]-amino}-methyl)-benzoic acid methyl ester,
1-(4-Fluoro-phenyl)-1H-indazole-4-carboxylic acid (2-pyridin-4-yl-ethyl)-amide,
1-(4-Fluoro-phenyl)-1H-indazole-4-carboxylic acid (2-pyridin-3-yl-ethyl)-amide,
1-(4-Fluoro-phenyl)-1H-indazole-4-carboxylic acid (3-morpholin-4-yl-propyl)-amide,
1-(4-Fluoro-phenyl)-1H-indazole-4-carboxylic acid [2-(morpholine-4-sulfonyl)-ethyl]-amide,
1-(4-Fluoro-phenyl)-1H-indazole-4-carboxylic acid (3-dimethylsulfamoyl-propyl)-amide,
1-(4-Fluoro-phenyl)-1H-indazole-4-carboxylic acid [3-(morpholine-4-sulfonyl)-propyl]-amide,
1-(4-Fluoro-phenyl)-1H-indazole-4-carboxylic acid (4-carbamoyl-cyclohexylmethyl)-amide,
1-(4-Fluoro-phenyl)-1H-indazole-4-carboxylic acid 2-chloro-4-methanesulfonyl-benzylamide, 1-(4-Fluoro-phenyl)-1H-indazole-4-carboxylic acid (2-oxo-2,3-dihydro-1H-benzoimidazol-5-ylmethyl)-amide, and
1-(4-Fluoro-phenyl)-1H-indazole-4-carboxylic acid 4-dimethylcarbamoyl-benzylamide.

Example 4

Synthesis of 1-(4-Fluoro-phenyl)-1H-indazole-4-carboxylic acid (6-bromo-pyridin-3-ylmethyl)-amide (4)

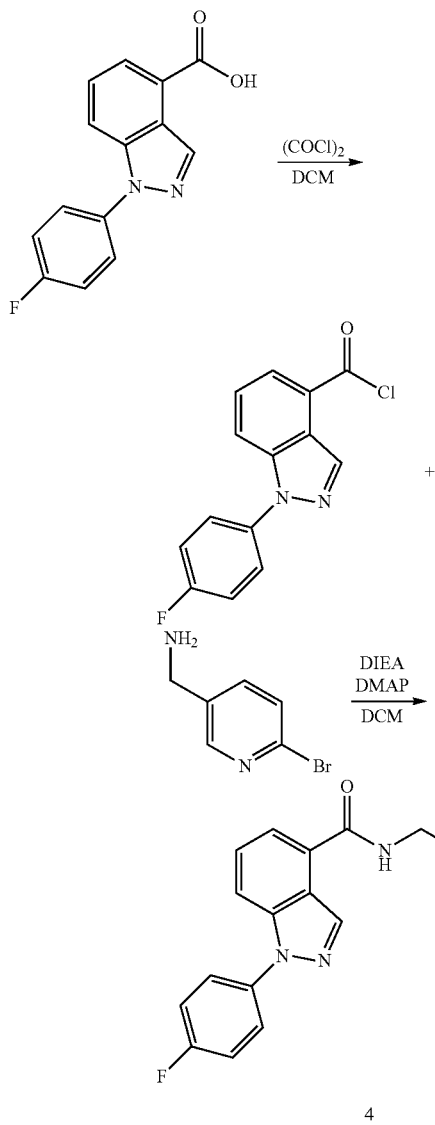

To a solution of 1-(4-fluoro-phenyl)-1H-indazole-4-carboxylic acid (0.400 g, 1.56 mmol) in $CH_2Cl_2$ (5 mL) at room temperature was added oxalyl chloride (0.86 mL, 1.7 mmol) followed by DMF (20 µL). Gas evolution was observed. After 30 minutes, the solution was concentrated in vacuo to afford 1-(4-fluoro-phenyl)-1H-indazole-4-carboxylic acid chloride which was used without further purification.

A mixture of 1-(4-fluoro-phenyl)-1H-indazole-4-carboxylic acid chloride (416 mg, 1.51 mmol), 6-bromo-pyridin-3-yl-methylamine (311 mg, 1.66 mmol) and DMAP (18.5 mg, 0.151 mmol) in DCM (10 mL) was treated with DIEA (1.32 mL, 7.56 mmol). The solution was stirred at room temperature. After 16 hours the mixture was diluted with DCM (30 mL). The organic layer was washed with saturated aqueous $NH_4Cl$ (2×10 mL), saturated aqueous $NaHCO_3$ (2×10 mL), water (10 mL), brine (10 mL) and dried over $MgSO_4$, filtered and concentrated. The residue was purified by silica gel chromatography eluting with a gradient of 0-50% ethyl acetate in hexanes to afford the title compound as a white solid.

The following compounds were also prepared by methods described in Example 4:
1-(4-Fluoro-phenyl)-1H-indazole-4-carboxylic acid (2-methoxy-pyridin-4-ylmethyl)-amide,
1-(4-Fluoro-phenyl)-1H-indazole-4-carboxylic acid (6-methoxy-pyridin-3-ylmethyl)-amide,
5-({[1-(4-Fluoro-phenyl)-1H-indazole-4-carbonyl]-amino}-methyl)-nicotinic acid ethyl ester,
1-(4-Fluoro-phenyl)-1H-indazole-4-carboxylic acid 3-methylsulfamoyl-benzylamide, and
1-(4-Fluoro-phenyl)-1H-indazole-4-carboxylic acid 3-dimethylsulfamoyl-benzylamide.

Example 5

Synthesis of 5-({[1-(4-Fluoro-phenyl)-1H-indazole-4-carbonyl]-amino}-methyl)-pyridine-2-carboxylic acid ethyl ester (5)

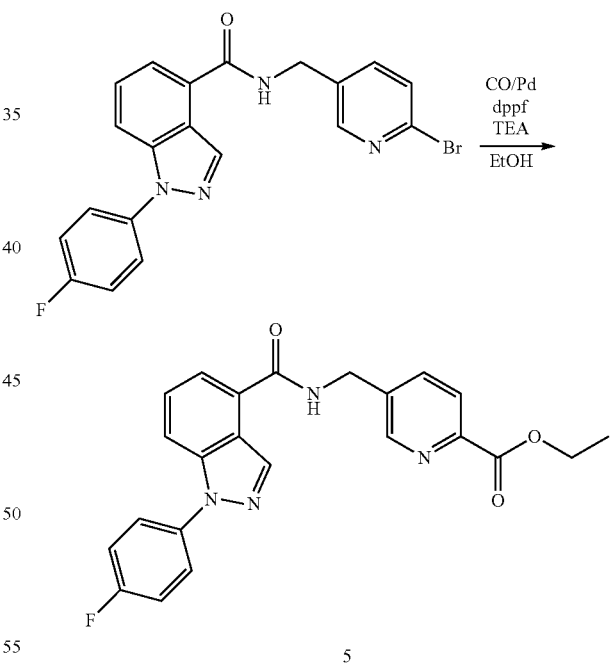

In a pressure reactor with stirring, a mixture of the 1-(4-fluoro-phenyl)-1H-indazole-4-carboxylic acid (6-bromo-pyridin-3-ylmethyl)-amide (260 mg, 0.61 mmol), triethylamine (0.17 mL, 1.2 mmol), dichloro(bisbenzonitrile) palladium (4.7 mg, 0.011 mmol), and 1,1-bis(diphenylphosphino)ferrocene (dppf) (20.3 mg, 0.0365 mmol) in absolute ethanol (10 mL) was charged with 15 bars of carbon monoxide and warmed at 140° C. After 4 hours, the pressure reactor was then cooled to room temperature, chilled on ice and returned to atmospheric pressure. The solution was diluted with satu-

Example 6

Synthesis of 1-(4-Fluoro-phenyl)-1H-indazole-4-carboxylic acid (6-carbamoyl-pyridin-3-ylmethyl)-amide (6)

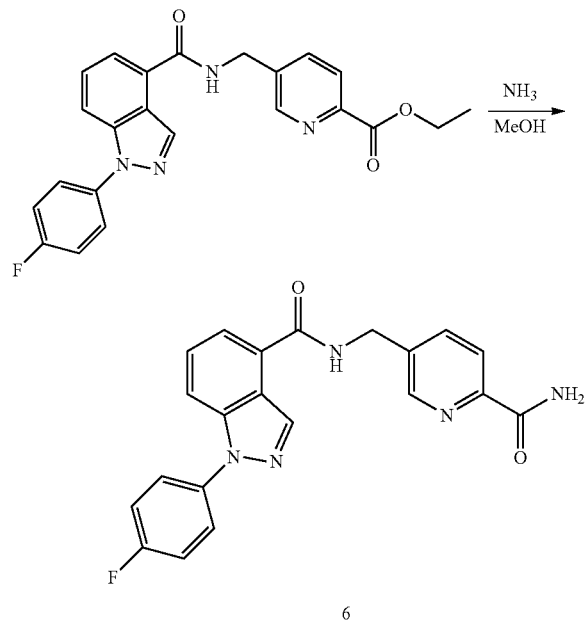

A solution of 5-({[1-(4-fluoro-phenyl)-1H-indazole-4-carbonyl]-amino}-methyl)-pyridine-2-carboxylic acid ethyl ester (Example 5) (60 mg, 0.1 mmol) in a 7 N solution of ammonia in methanol (0.65 mL, 4.6 mmol) was stirred at 100° C. in a sealed tube for 16 hours. The mixture was cooled to room temperature and filtered. The solid was washed with MeOH (3×3 mL) and dried. The solid was then triturated with ethyl acetate (2 mL), sonicated, filtered and air dried to afford the title compound.

The following compounds were also prepared by methods described in Example 6:

1-(4-Fluoro-phenyl)-1H-indazole-4-carboxylic acid (6-methylcarbamoyl-pyridin-3-ylmethyl)-amide,
1-(4-Fluoro-phenyl)-1H-indazole-4-carboxylic acid (5-carbamoyl-pyridin-3-ylmethyl)-amide,
1-(4-Fluoro-phenyl)-1H-indazole-4-carboxylic acid (5-methylcarbamoyl-pyridin-3-ylmethyl)-amide, and
1-(4-Fluoro-phenyl)-1H-indazole-4-carboxylic acid (2-carbamoyl-pyridin-4-ylmethyl)-amide.

Example 7

Synthesis of 1-(4-Fluoro-phenyl)-1H-indazole-4-carboxylic acid (6-methanesulfonyl-pyridin-3-ylmethyl)-amide (7)

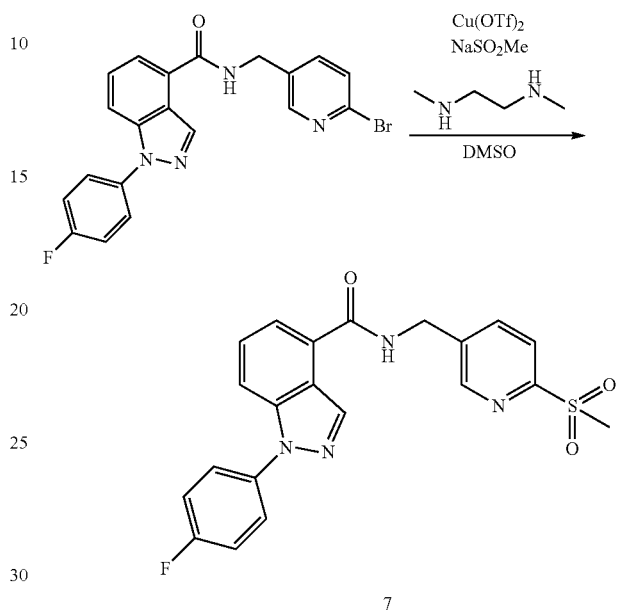

A microwave tube was charged with 1-(4-fluoro-phenyl)-1H-indazole-4-carboxylic acid (6-bromo-pyridin-3-ylmethyl)-amide (650 mg, 1.5 mmol), copper(II) triflate (550 mg, 1.5 mmol) and sodium methanesulfinate (230 mg, 2.3 mmol). The flask was sealed, evacuated and purged (3 times) with nitrogen. The solids were taken up in DMSO (5 mL) and N,N'-dimethylethylene diamine (0.490 mL, 4.59 mmol) was added. The solution was stirred at 100° C. After 16 hours, the mixture was diluted with EtOAc (10 mL) and washed with saturated aqueous NH$_4$Cl (5 mL), saturated aqueous NaHCO$_3$ (5 mL) and brine (5 mL). The organic layer was dried over MgSO$_4$, filtered through diatomaceous earth and concentrated. The residue was purified by silica gel chromatography eluting with a gradient of 0-80% ethyl acetate in hexanes. Fractions containing the product were pooled and further purified by silica gel chromatography eluting with a gradient of 0-60% ethyl acetate in hexanes. Desired fractions were pooled and concentrated, and the solid was triturated with hexanes (10 mL) to afford the title compound as a white solid.

The following compound was prepared by the methods described in Example 7:

1-(4-Fluoro-phenyl)-1H-indazole-4-carboxylic acid [(S)-1-(6-methanesulfonyl-pyridin-3-yl)-propyl]-amide.

The following compound was prepared with modifications to Example 7: 3 equivalents of CuI was used as a catalyst instead of copper triflate, and 3 equivalents of sodium 3-methoxy-3-oxopropane-1-sulfinate was used instead of sodium methane sulfinate. The solvent was DMSO with no amine ligand was added. The mixture was warmed at 110° C. for 30 minutes using microwave heating (as described in Baskin, J. M., et al., Tetrahedron Lett., 2002, 43 (47), 8479):

3-[5-({[1-(4-Fluoro-phenyl)-1H-indazole-4-carbonyl]-amino}-methyl)-pyridine-2-sulfonyl]-propionic acid methyl ester.

Example 8

Synthesis of 1-(4-Fluoro-phenyl)-1H-indazole-4-carboxylic acid [6-(3-hydroxy-propane-1-sulfonyl)-pyridin-3-ylmethyl]-amide (8)

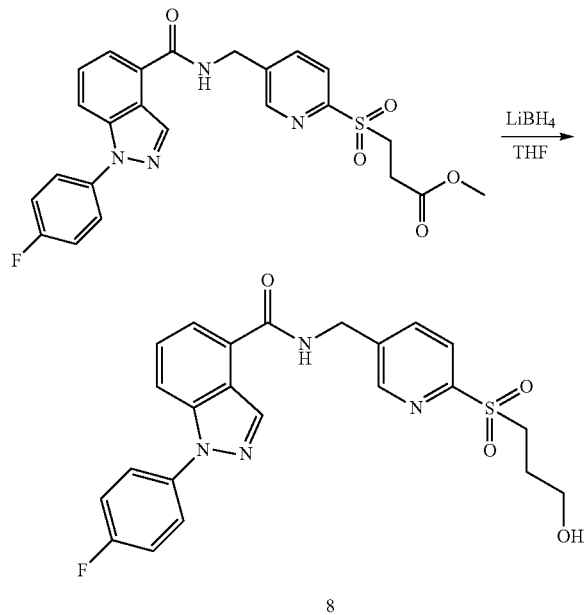

The solution of 3-[5-({[1-(4-fluoro-phenyl)-1H-indazole-4-carbonyl]-amino}-methyl)-pyridine-2-sulfonyl]-propionic acid methyl ester (33 mg, 0.066 mmol) in THF (5 mL) was treated with lithium borohydride (8.7 mg, 0.40 mmol) at room temperature and the mixture was warmed at reflux. After 1 hour, the reaction was cooled to room temperature, quenched with water (50 mL) and diluted with ethyl acetate (50 mL). The organic layer was separated and the aqueous layer was extracted with ethyl acetate (2×25 mL). The combined organic layers were washed with brine (20 mL), dried over MgSO$_4$, filtered and concentrated. The residue was purified by silica gel chromatography eluting with a gradient of 0-10% MeOH in CH$_2$Cl$_2$ to afford the title compound.

The following compound was also prepared by methods described in Example 8:
1-(4-Fluoro-phenyl)-1H-indazole-4-carboxylic acid [1-(2-hydroxy-ethyl)-2-oxo-1,2-dihydro-pyridin-4-ylmethyl]-amide.

Example 9

Synthesis of 1-(4-Fluoro-phenyl)-1H-indazole-4-carboxylic acid (4-bromo-2-chloro-benzyl)-methoxymethyl-amide (9)

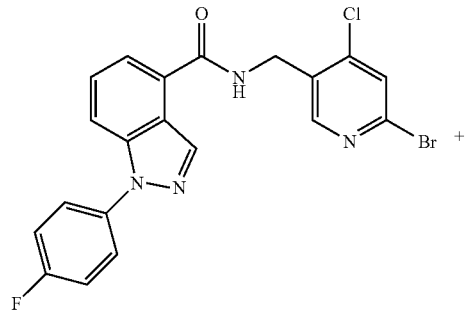

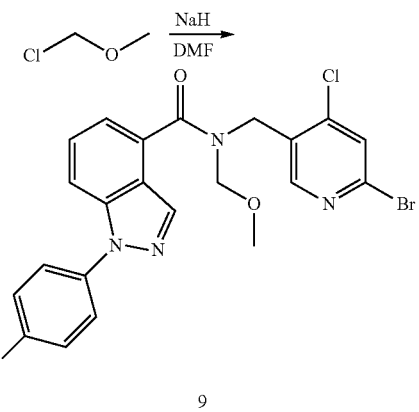

To a room temperature solution of 1-(4-fluoro-phenyl)-1H-indazole-4-carboxylic acid 4-bromo-2-chloro-benzylamide (1.5 g, 3.3 mmol) in DMF (30 mL) was added a 60% dispersion of sodium hydride in mineral oil (145 mg, 3.60 mmol). After stirring for 10 minutes, chloromethyl methyl ether (0.28 mL, 3.6 mmol) was added. After 16 hours, the mixture was then diluted with water (30 mL) and extracted with ethyl acetate (3×20 mL). The extract was washed with saturated aqueous ammonium chloride (30 mL) followed by brine (30 mL) and dried over sodium sulfate. The residue was purified by silica gel chromatography eluting with a gradient of 0-70% ethyl acetate in hexanes. The fractions containing product were condensed in vacuo to provide a colorless oil. The oil was dissolved in diethyl ether (25 mL), causing the starting material to solidify from solution. Filtration gave the title compound as a white solid.

The following compounds were also prepared by methods described in Example 9:
1-(4-Fluoro-phenyl)-1H-indazole-4-carboxylic acid (4-methanesulfonyl-benzyl)-propyl-amide,
1-(4-Fluoro-phenyl)-1H-indazole-4-carboxylic acid 4-dimethylsulfamoyl-benzylamide, and
1-(4-Fluoro-phenyl)-1H-indazole-4-carboxylic acid (2-chloro-4-dimethylsulfamoyl-benzyl)-methyl-amide.

Example 10

Synthesis of 1-(4-Fluoro-phenyl)-1H-indazole-4-carboxylic acid 2-chloro-4-cyano-benzylamide (10)

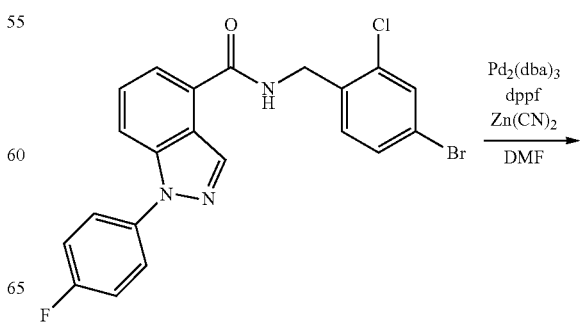

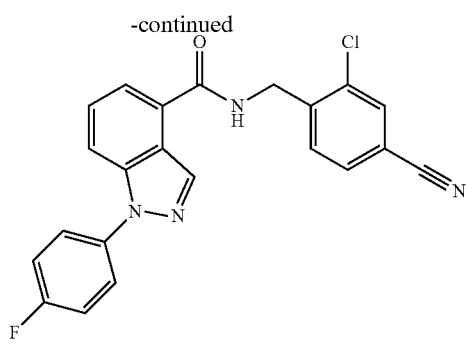

10

In a sealed tube, 1-(4-fluoro-phenyl)-1H-indazole-4-carboxylic acid (4-bromo-2-chloro-benzyl)-methoxymethylamide (0.30 g, 0.65 mmol), Pd$_2$(dba)$_3$ (40.0 mg, 0.440 mmol), dppf (44 mg, 0.079 mmol), Zn(CN)$_2$ (77 mg, 0.66 mmol), and Zn (10.5 mg, 0.160 mmol) were dissolved in anhydrous DMF (3 mL). The mixture was warmed at 120° C. for 3 hours. The mixture cooled to room temperature, and diluted with saturated aqueous ammonium chloride (20 mL), extracted with ethyl acetate (20 mL), washed with brine (30 mL), and dried over sodium sulfate. The crude was purified by silica gel chromatography eluting with a gradient of 0-70% ethyl acetate in hexanes to afford the title compound as a white powder.

The following compound was also prepared by methods described in Example 10:

1-(4-Fluoro-phenyl)-1H-indazole-4-carboxylic acid 4-cyano-benzylamide.

Example 11

Synthesis of 1-(4-Fluoro-phenyl)-1H-indazole-4-carboxylic acid 4-carbamoyl-2-chloro-benzylamide (11)

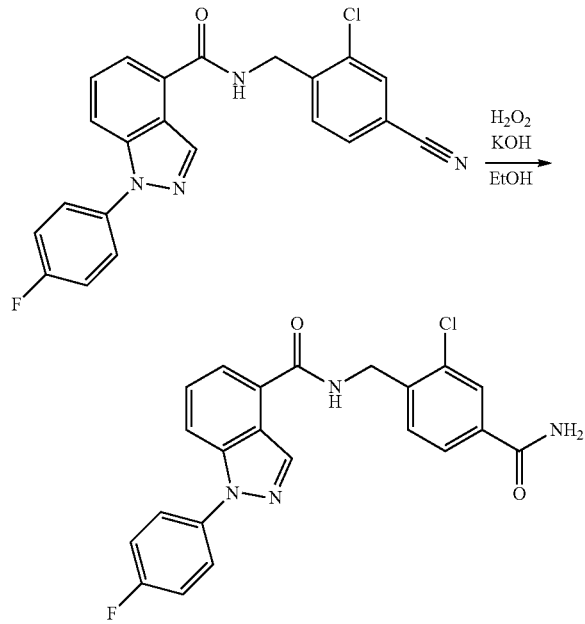

To a suspension of 1-(4-fluoro-phenyl)-1H-indazole-4-carboxylic acid 2-chloro-4-cyano-benzylamide in a 1:1 mixture of EtOH—H$_2$O (2.0 mL) was added KOH (0.018 g, 0.32 mmol) and a 30% solution of H$_2$O$_2$ in H$_2$O (0.13 mL, 1.1 mmol). The suspension was sealed and heated briefly to dissolve the mixture. The resultant solution was stirred at room temperature for 16 hours, during which time a solid precipitated. The mixture was diluted with H$_2$O (10 mL) and the solid was collected by filtration and dried to afford the title compound as a white powder.

The following compound was also prepared by methods described in Example 11:

1-(4-Fluoro-phenyl)-1H-indazole-4-carboxylic acid 4-carbamoyl-benzylamide.

Example 12

Synthesis of 3-({[1-(4-Fluoro-phenyl)-1H-indazole-4-carbonyl]-amino}-methyl)-benzoic acid (12)

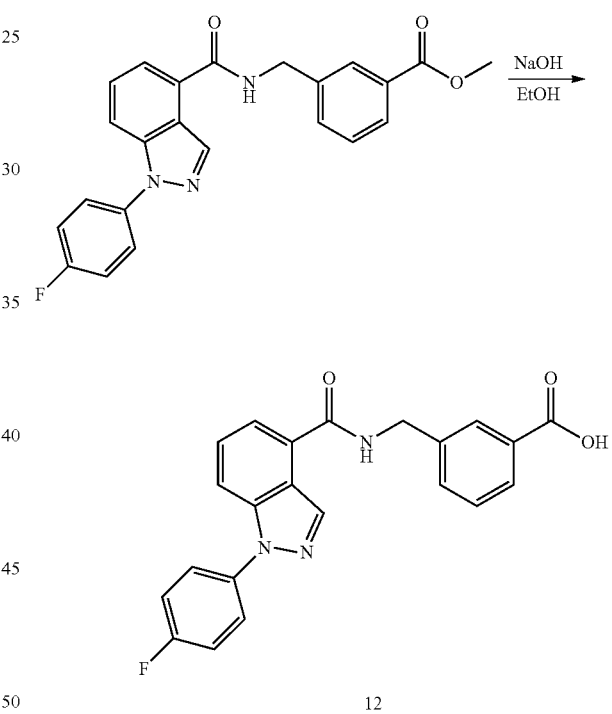

To a solution of 3-({[1-(4-fluoro-phenyl)-1H-indazole-4-carbonyl]-amino}-methyl)-benzoic acid methyl ester (430 mg, 1.0 mmol) in ethanol (15 mL) was added a 2 N solution of aqueous sodium hydroxide (3.0 mL, 6.0 mmol). The mixture was heated at 80° C. for 4 hours. The mixture was cooled and concentrated in vacuo to remove the ethanol and then added to a solution of 1 N aqueous HCl (30 mL). The white precipitate was collected by filtration and dried to afford the title compound as a white solid.

The following compound was also prepared by methods described in Example 12:

4-({[1-(4-Fluoro-phenyl)-1H-indazole-4-carbonyl]-amino}-methyl)-benzoic acid.

Example 13

Synthesis of 1-(4-Fluoro-phenyl)-1H-indazole-4-carboxylic acid 3-methylcarbamoyl-benzylamide (13)

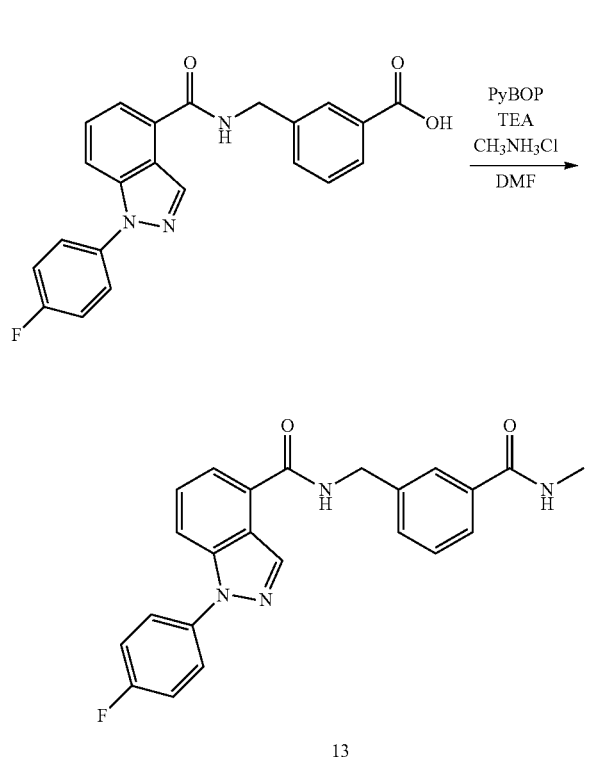

13

To a solution of 3-({[1-(4-fluoro-phenyl)-1H-indazole-4-carbonyl]-amino}-methyl)-benzoic acid (70 mg, 0.2 mmol) in DMF (5 mL) was added Et₃N (0.07 mL, 0.6 mmol) and PyBOP (100 mg, 0.2 mmol). After 15 minutes of stirring at room temperature, methylamine hydrochloride (15 mg, 0.22 mmol) was added. After 16 hours, the mixture was diluted with saturated aqueous ammonium chloride (20 mL) and extracted with ethyl acetate (3×20 mL). The combined organic layers were washed with saturated aqueous sodium bicarbonate (20 mL), brine (20 mL) and dried over sodium sulfate. The crude product was purified by silica gel chromatography eluting with a gradient of 0-100% ethyl acetate in hexanes. The material from the column was then crystallized from EtOAc/ether/hexanes to afford the title compound as a white solid.

The following compounds were also prepared by methods described in Example 13:

1-(4-Fluoro-phenyl)-1H-indazole-4-carboxylic acid 3-propylcarbamoyl-benzylamide, 1-(4-Fluoro-phenyl)-1H-indazole-4-carboxylic acid 3-ethylcarbamoyl-benzylamide, and 1-(4-Fluoro-phenyl)-1H-indazole-4-carboxylic acid 3-(2-methoxy-ethylcarbamoyl)-benzylamide.

Example 14

Synthesis of 1-(4-Fluoro-phenyl)-1H-indazole-4-carboxylic acid 4-(2-hydroxy-ethylsulfamoyl)-benzylamide (14)

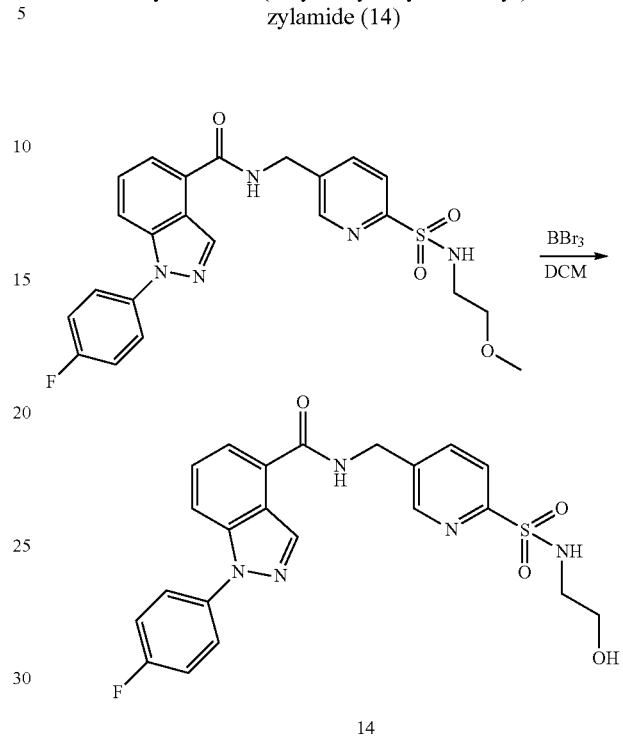

14

To a chilled (−78° C.) solution of 1-(4-fluoro-phenyl)-1H-indazole-4-carboxylic acid 4-(2-methoxy-ethylsulfamoyl)-benzylamide (22 mg, 0.45 mmol) in dichloromethane (5 mL) was added in several portions a 1 M solution of BBr₃ (0.13 mL, 0.13 mmol) in dichloromethane. The mixture was allowed to warm to room temperature. The mixture was quenched with saturated aqueous sodium bicarbonate and then extracted with ethyl acetate (3×10 mL). The combined organic layers were washed with brine (2×5 mL), dried over magnesium sulfate, filtered and concentrated. The material was purified by silica gel chromatography eluting with a gradient of 0-100% ethyl acetate in hexanes to afford the title compound as a white powder.

Example 15

Synthesis of 3-Bromo-1H-indazole-4-carboxylic acid methyl ester (15)

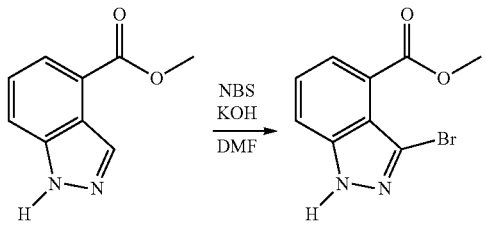

To a solution of 1H-indazole-4-carboxylic acid methyl ester (380 mg, 2.2 mmol) in DMF (5 mL) was added N-bromosuccinimide (NBS) (976 mg, 4.32 mmol) and KOH (485 mg, 8.64 mmol). After 1 hour, the reaction mixture was diluted with saturated aqueous ammonium chloride (20 mL) and extracted with ethyl acetate (3×20 mL). The combined organic layers were washed with saturated aqueous sodium bicarbonate and brine (20 mL), dried over sodium sulfate and concentrated in vacuo to afford the title compound as a solid.

3-Bromo-1H-indazole-4-carboxylic acid methyl ester was then subjected to the reaction conditions described in Example 2, for the synthesis of 1-(4-fluoro-phenyl)-1H-indazole-4-carboxylic acid, to yield 3-bromo-1-(4-fluoro-phenyl)-1H-indazole-4-carboxylic acid. Using the methods described in Example 2, 3-bromo-1-(4-fluoro-phenyl)-1H-indazole-4-carboxylic acid was used to provide the following compounds:
3-Bromo-1-(4-fluoro-phenyl)-1H-indazole-4-carboxylic acid 4-methanesulfonyl-benzylamide, and
3-Bromo-1-(4-fluoro-phenyl)-1H-indazole-4-carboxylic acid 4-methylsulfamoyl-benzylamide.

Example 16

Synthesis of 1-(4-Fluoro-phenyl)-1H-indazole-4-carboxylic acid (2-oxo-1,2-dihydro-pyridin-4-ylmethyl)-amide (16)

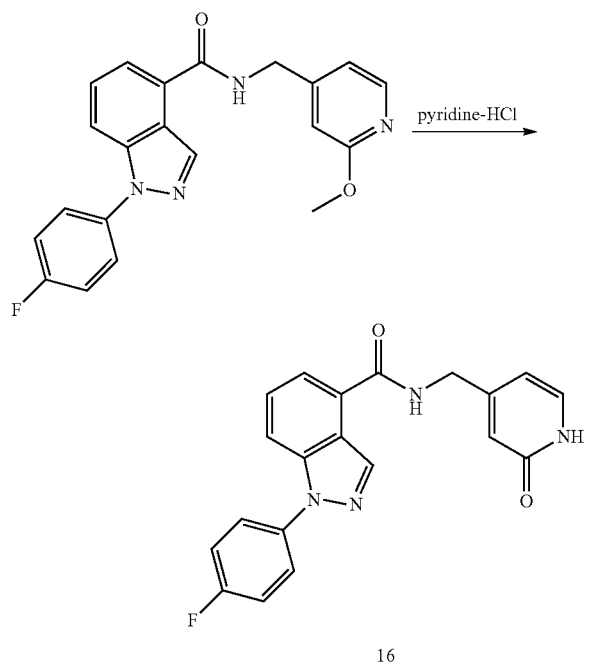

16

1-(4-Fluoro-phenyl)-1H-indazole-4-carboxylic acid (2-methoxy-pyridin-4-ylmethyl)-amide (38 mg, 0.10 mmol) and pyridinium hydrochloride (117 mg, 1.01 mmol) were heated to 125° C. in a sealed tube. After 10 minutes, the mixture was cooled to room temperature and diluted with ethyl acetate (3 mL) and water (3 mL). The organic layer was washed with water (3×3 mL) and concentrated at 45° C. under a stream of nitrogen. The residue was dissolved in CH$_2$Cl$_2$ (3 mL) and concentrated (repeated 3 times). The solid was triturated with ether (3 mL), filtered and air dried to afford the title compound as a white solid.

The following compound was also prepared by methods described in Example 16:
1-(4-Fluoro-phenyl)-1H-indazole-4-carboxylic acid (6-oxo-1,6-dihydro-pyridin-3-ylmethyl)-amide.

Example 17

Synthesis of 1-(4-Fluoro-phenyl)-1H-indazole-4-carboxylic acid (1-methyl-2-oxo-1,2-dihydro-pyridin-4-ylmethyl)-amide (17)

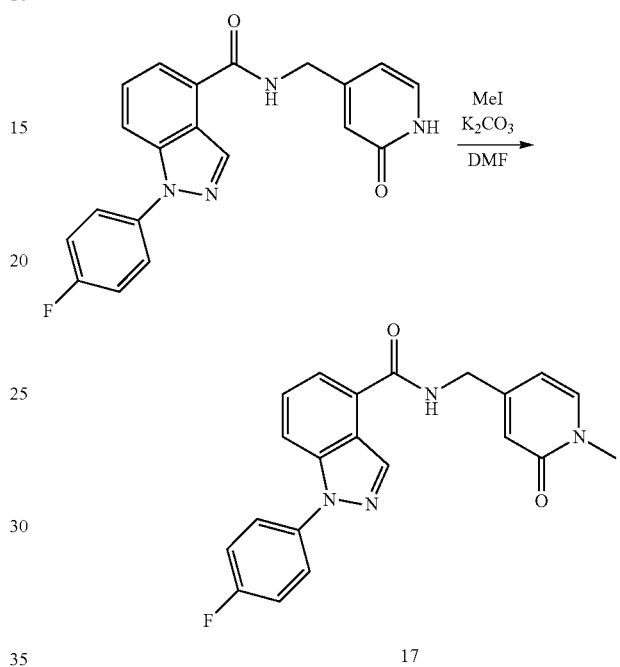

17

To a stirred solution of 1-(4-fluoro-phenyl)-1H-indazole-4-carboxylic acid (2-oxo-1,2-dihydro-pyridin-4-ylmethyl)-amide (50 mg, 0.1 mmol) in DMF (1.0 mL) was added K$_2$CO$_3$ (45.8 mg, 0.331 mmol) followed by iodomethane (0.017 mL, 0.28 mmol). The mixture was warmed at 60° C. for 3 hours. The mixture was diluted with water (10 mL), and a white solid was obtained by filtration. The solid was washed with water (5×10 mL) and air dried. The resulting solid was purified by silica gel chromatography eluting with a gradient of 0-5% MeOH in CH$_2$Cl$_2$ to afford the title compound as a white solid.

The following compounds were also prepared by methods described in Example 17:
1-(4-Fluoro-phenyl)-1H-indazole-4-carboxylic acid (1-methyl-6-oxo-1,6-dihydro-pyridin-3-ylmethyl)-amide,
[4-({[1-(4-Fluoro-phenyl)-1H-indazole-4-carbonyl]-amino}-methyl)-2-oxo-2H-pyridin-1-yl]-acetic acid ethyl ester,
[5-({[1-(4-Fluoro-phenyl)-1H-indazole-4-carbonyl]-amino}-methyl)-2-oxo-2H-pyridin-1-yl]-acetic acid ethyl ester,
1-(4-Fluoro-phenyl)-1H-indazole-4-carboxylic acid (1-carbamoylmethyl-6-oxo-1,6-dihydro-pyridin-3-ylmethyl)-amide,
1-(4-Fluoro-phenyl)-1H-indazole-4-carboxylic acid (1-cyanomethyl-2-oxo-1,2-dihydro-pyridin-4-ylmethyl)-amide, and
[4-({[1-(4-Fluoro-phenyl)-1H-indazole-4-carbonyl]-amino}-methyl)-pyridin-2-yloxy]-acetic acid ethyl ester.

Example 18

Synthesis of 1-(4-Fluoro-phenyl)-1H-indazole-4-carboxylic acid (6-amino-pyridin-3-ylmethyl)-amide (18)

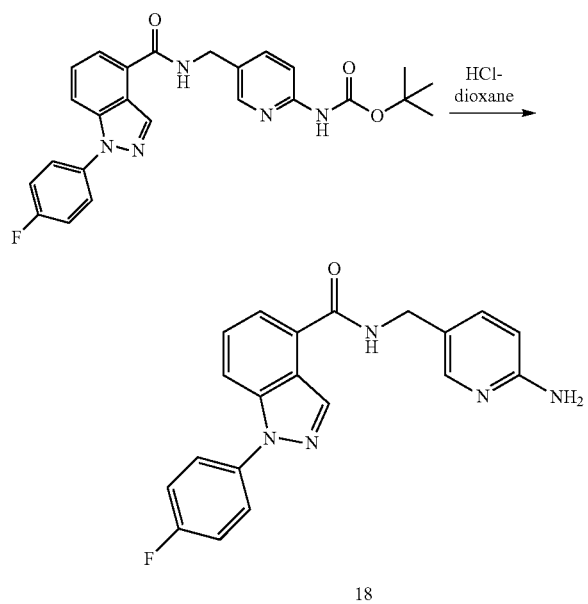

[5-({[1-(4-Fluoro-phenyl)-1H-indazole-4-carbonyl]-amino}-methyl)-pyridin-2-yl]-carbamic acid tert-butyl ester (0.200 g, 0.433 mmol) synthesized as described in Example 4, via the acid chloride and tert-butyl[5-(aminomethyl)pyridine-2-yl]carbamate) was treated with a solution of 4 N HCl in dioxane (5 mL, 20 mmol) and stirred for 6 hours at room temperature. A solid was obtained by filtration, and partitioned between saturated aqueous NaHCO₃ (10 mL) and ethyl acetate (10 mL). The organic layer was separated and the aqueous layer was extracted with ethyl acetate (2×10 mL). The combined organic layers were dried over MgSO₄, filtered and concentrated in vacuo. The resulting solid was triturated with ethyl acetate (1 mL), filtered and air dried to afford the title compound as a white crystalline solid.

Example 19

Synthesis of 1-(4-Fluoro-phenyl)-1H-indazole-4-carboxylic acid (6-acetylamino-pyridin-3-ylmethyl)-amide (19)

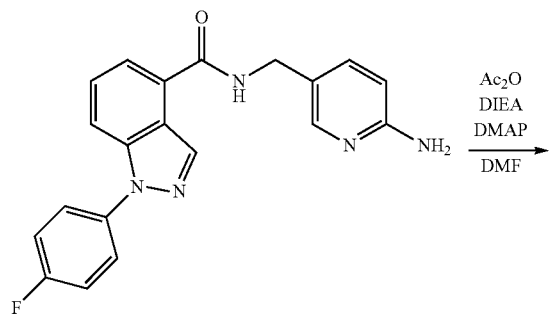

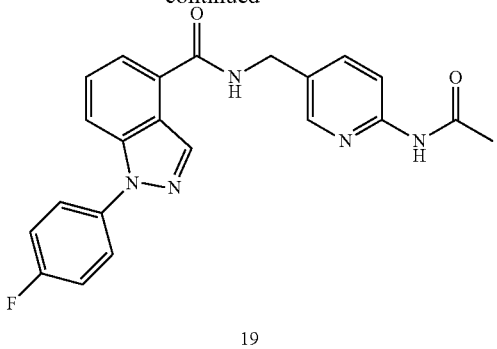

A chilled (0° C.) solution of 1-(4-fluoro-phenyl)-1H-indazole-4-carboxylic acid (6-amino-pyridin-3-ylmethyl)-amide (40.0 mg, 0.111 mmol) in DMF (1 mL) was treated with 4-dimethylaminopyridine (1 mg, 0.01 mmol), DIEA (0.39 mL, 2.2 mmol) and acetic anhydride (0.062 mL, 0.66 mmol). The mixture was allowed to gradually warm to room temperature. The solution was diluted with ethyl acetate (30 mL) and washed with saturated aqueous NH₄Cl (3×10 mL), saturated aqueous NaHCO₃ (20 mL) and brine (20 mL). The organic layer was dried over MgSO₄, filtered and concentrated.

The residue was purified by silica gel chromatography, eluting with a gradient of 70-100% ethyl acetate in hexanes to afford the title compound as a white solid.

Example 20

Synthesis of 1-(4-Fluoro-phenyl)-1H-indazole-4-carboxylic acid (6-methanesulfonylamino-pyridin-3-ylmethyl)-amide (20)

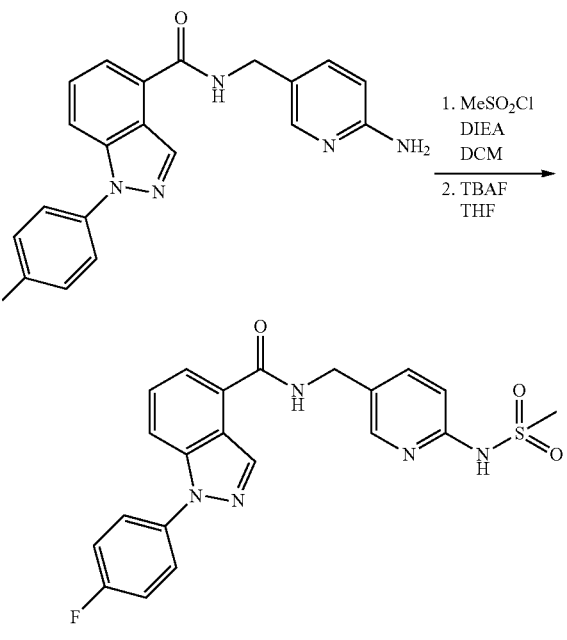

To a solution of 1-(4-fluoro-phenyl)-1H-indazole-4-carboxylic acid (6-amino-pyridin-3-ylmethyl)-amide (40.0 mg, 0.111 mmol) in dichloromethane (1.0 mL) was added DIEA (0.15 mL, 0.89 mmol). The solution was cooled to 0° C., treated with methanesulfonyl chloride (0.021 mL, 0.28 mmol), and gradually allowed to warm to room temperature. The solution was diluted $CH_2Cl_2$ (20 mL) and washed with saturated aqueous $NH_4Cl$ (3×10 mL), saturated aqueous $NaHCO_3$ (10 mL) and brine (10 mL). The organic layer was dried over $MgSO_4$, filtered and concentrated. The crude mixture was diluted with THF (0.5 mL) and a 1 M solution of TBAF in THF (1.0 mL, 1.0 mmol) was added. The solution was warmed at reflux for 6 hours. The solution was cooled to room temperature and quenched with saturated aqueous $NH_4Cl$ (15 mL), diluted with ethyl acetate (15 mL), and washed with $NaHCO_3$ (10 mL) and brine (10 mL). The organic layer was dried over $MgSO_4$, filtered and concentrated. The residue was purified by silica gel chromatography, eluting with a gradient of 0-10% MeOH in $CH_2Cl_2$ to afford the title compound as a solid.

Example 21

Synthesis of 1-(4-Fluoro-phenyl)-1H-indazole-4-carboxylic acid (6-ethynyl-pyridin-3-ylmethyl)-amide (21)

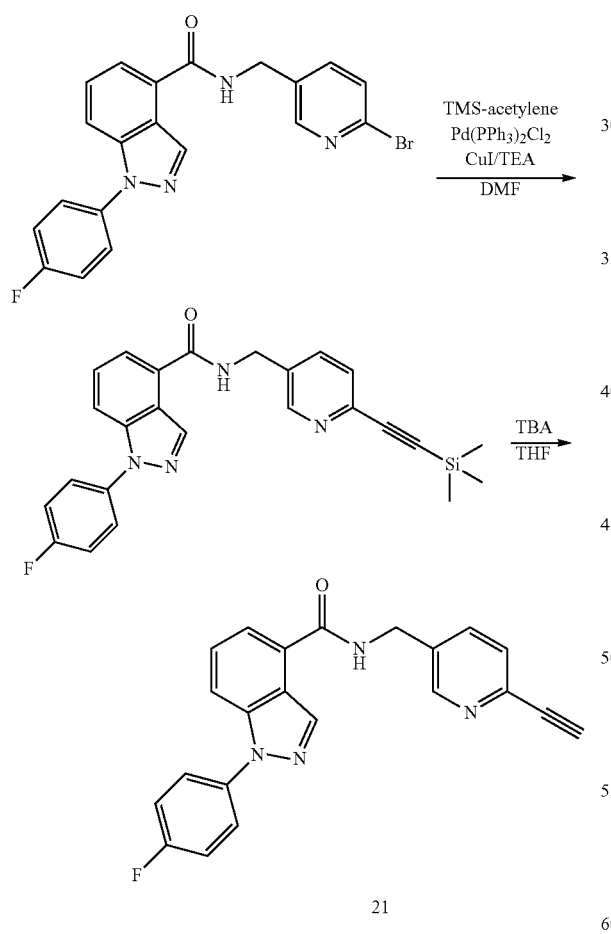

To a mixture of 1-(4-fluoro-phenyl)-1H-indazole-4-carboxylic acid (6-bromo-pyridin-3-ylmethyl)-amide (105 mg, 0.247 mmol), trimethylsilyl acetylene (0.105 mL, 0.741 mmol), copper(I) iodide (4.7 mg, 0.025 mmol) and $Pd(PPh_3)_2Cl_2$ (8.7 mg, 0.012 mmol) was added triethylamine (1.0 mL) and anhydrous DMF (0.25 mL). After 16 hours, the mixture was diluted with diethyl ether (50 mL) and quenched with saturated aqueous ammonium chloride (50 mL). The organic layer was washed with saturated aqueous ammonium chloride (50 mL) and brine (50 mL), dried over $MgSO_4$ and concentrated. The crude solid was purified by silica gel chromatography eluting with a gradient of 0-50% ethyl acetate in hexanes to afford 1-(4-fluoro-phenyl)-1H-indazole-4-carboxylic acid (6-trimethylsilanylethynyl-pyridin-3-ylmethyl)-amide as a tan solid.

1-(4-Fluoro-phenyl)-1H-indazole-4-carboxylic acid (6-trimethylsilanylethynyl-pyridin-3-ylmethyl)-amide (70.0 mg, 0.158 mmol) was dissolved in THF (1.0 mL) and treated with a 1 M solution of TBAF in THF (0.16 mL, 0.16 mmol) at room temperature. The solution was stirred for 2 hours and then diluted with diethyl ether (10 mL) and quenched with water (10 mL). The aqueous layers were extracted with diethyl ether (3×5 mL). The combined organic layers were washed with brine (10 mL), dried over $MgSO_4$ and concentrated. The crude product was purified by silica gel chromatography eluting with a gradient of 0-70% ethyl acetate in hexanes to afford the title compound as a white solid.

Example 22

Synthesis of 1-(4-Fluoro-phenyl)-1H-indazole-4-carboxylic acid (6-methanesulfonylmethyl-pyridin-3-ylmethyl)-amide (22)

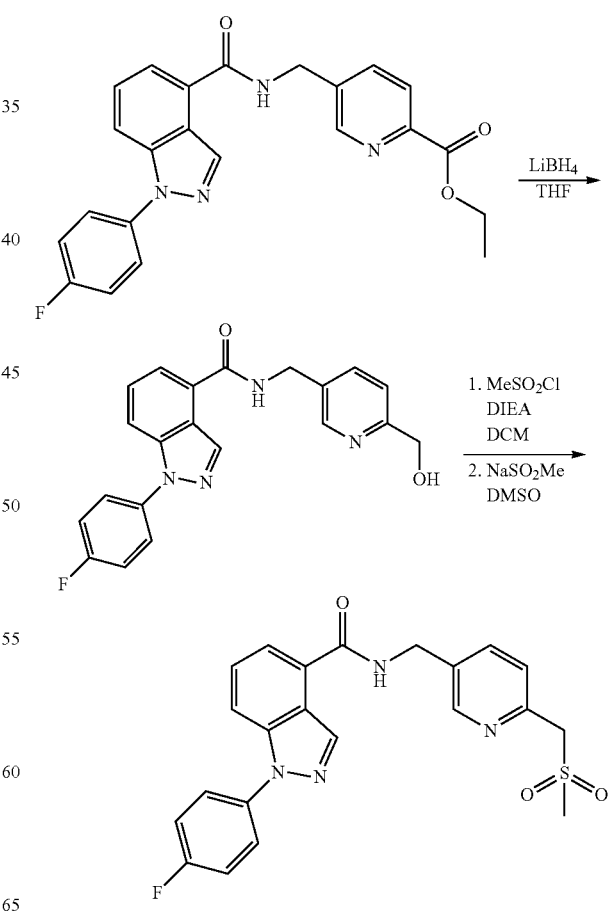

To a solution of the 5-({[1-(4-fluoro-phenyl)-1H-indazole-4-carbonyl]-amino}-methyl)-pyridine-2-carboxylic acid ethyl ester (40.0 mg, 0.0960 mmol) in THF (3.0 mL) was added lithium borohydride (12 mg, 0.57 mmol). The mixture was warmed at reflux for 18 hours. The solution was cooled to room temperature, quenched with water (5 mL) and diluted with ethyl acetate (5 mL). The organic layer was separated and the aqueous layer was extracted with ethyl acetate (2×5 mL). The combined organic layers were washed with brine (5 mL), dried over MgSO$_4$, filtered and concentrated. The residue was purified by silica gel chromatography eluting with a gradient of 0-10% MeOH in CH$_2$Cl$_2$ to afford the alcohol intermediate as an off-white solid.

To a solution of the alcohol (27 mg, 0.071 mmol) in CH$_2$Cl$_2$ (2 mL) was added DIEA (0.037 mL, 0.21 mmol) and methanesulfonyl chloride (0.07 mL, 0.09 mmol) at 0° C. The resulting mixture was stirred at 0° C. for 1 hour and quenched with saturated aqueous ammonium chloride (2 mL), washed with brine (2 mL), dried over MgSO$_4$ and concentrated. The resultant crude mesylate was dissolved in DMSO (1 mL) and treated with sodium methanesulfinate (8.7 mg, 0.086 mmol) at room temperature. The mixture was stirred for 19 hours, and diluted with water (20 mL) and ethyl acetate (20 mL). The organic layer was separated and the aqueous layer was extracted with ethyl acetate (3×20 mL). The combined organic layers were washed with water (2×10 mL), saturated aqueous NaHCO$_3$ (25 mL), brine (25 mL), dried over MgSO$_4$, filtered and concentrated. The residue was purified by silica gel chromatography eluting with a gradient of 0-10% MeOH in CH$_2$Cl$_2$ to afford the title compound as a white solid.

Example 23

Synthesis of 6-Bromo-1-(4-fluoro-phenyl)-1H-indazole-4-carboxylic acid 4-methylsulfamoyl-benzylamide (23)

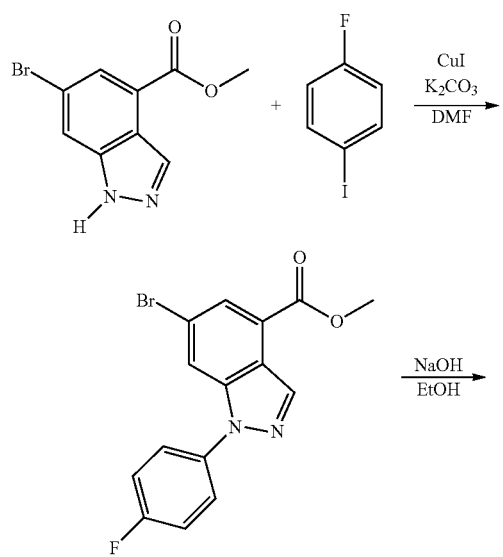

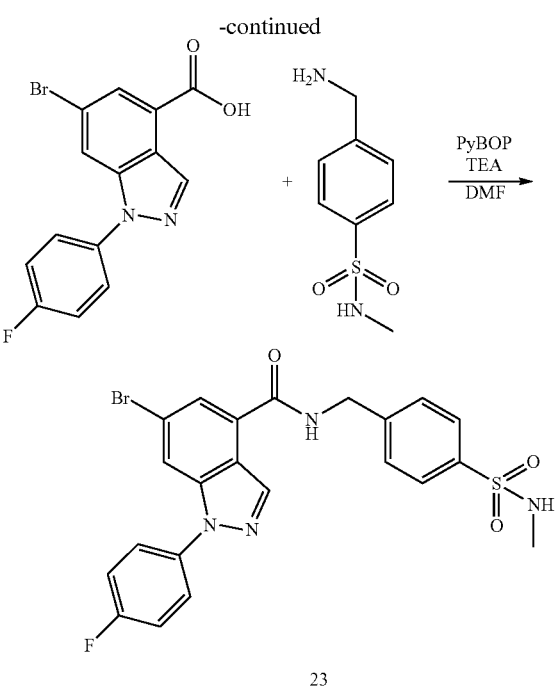

A mixture of 6-bromo-4-indazolecarboxylic acid methyl ester (2.0 g, 7.8 mmol), copper(I) iodide (0.4 g, 0.2 mmol), potassium carbonate (1.2 g, 8.5 mmol) and 4-fluoroiodobenzene (1.8 g, 8.5 mmol) was charged in a sealed tube at room temperature. The tube was evacuated and back-filled with argon, and DMF (10 mL) and rac-trans-N,N'-dimethylcyclohexane-1,2-diamine (0.20 g, 1.4 mmol) was added. The solution was stirred at 120° C. for 3 hours, cooled to room temperature, and diluted with water (30 mL) and ethyl acetate (50 mL). The organic layer was separated, washed with brine (10 mL) and dried over sodium sulfate. The solvent was removed in vacuo. The residue was purified by silica gel chromatography eluting with a gradient of 0-30% ethyl acetate in hexanes to afford 6-bromo-1-(4-fluoro-phenyl)-1H-indazole-4-carboxylic acid methyl ester.

To a stirred solution of 6-bromo-1-(4-fluoro-phenyl)-1H-indazole-4-carboxylic acid methyl ester (1.7 g, 4.8 mmol) in water (15 mL) and methanol (15 mL) was added a solution of 2 N aqueous sodium hydroxide (10 mL, 20 mmol). The solution was warmed at reflux for 1 hour. The reaction mixture was cooled to room temperature and acidified with 1 N aqueous HCl (pH=3-4) to afford a precipitate which was collected by filtration, washed with MeOH and air dried to afford 6-bromo-1-(4-fluoro-phenyl)-1H-indazole-4-carboxylic acid.

To a stirred room temperature solution of 6-bromo-1-(4-fluoro-phenyl)-1H-indazole-4-carboxylic acid (0.25 g, 0.70 mmol) in DMF (15 mL) was added PyBOP (0.45 g, 0.90 mmol) and triethylamine (0.20 g, 1.6 mmol). After 15 minutes, 4-aminomethyl-N-methyl-benzenesulfonamide (0.15 g, 0.7 mmol) was added. After 5 hours, the reaction was quenched with water (30 mL), and extracted with ethyl acetate (30 mL). The combined organic layers were washed with brine (30 mL) and dried over sodium sulfate and concentrated in vacuo. The residue was purified by silica gel chromatography eluting with a gradient of 30-50% ethyl acetate in hexanes to afford the title compound.

The following compound was also prepared by methods described in Example 23.

6-Bromo-1-(4-fluoro-phenyl)-1H-indazole-4-carboxylic acid 3-trifluoromethyl-benzylamide, and
6-Bromo-1-(4-fluoro-phenyl)-1H-indazole-4-carboxylic acid [(S)-1-(6-bromo-pyridin-3-yl)-propyl]-amide.

Example 24

Synthesis of 6-Cyano-1-(4-fluoro-phenyl)-1H-indazole-4-carboxylic acid 4-methylsulfamoyl-benzylamide (24)

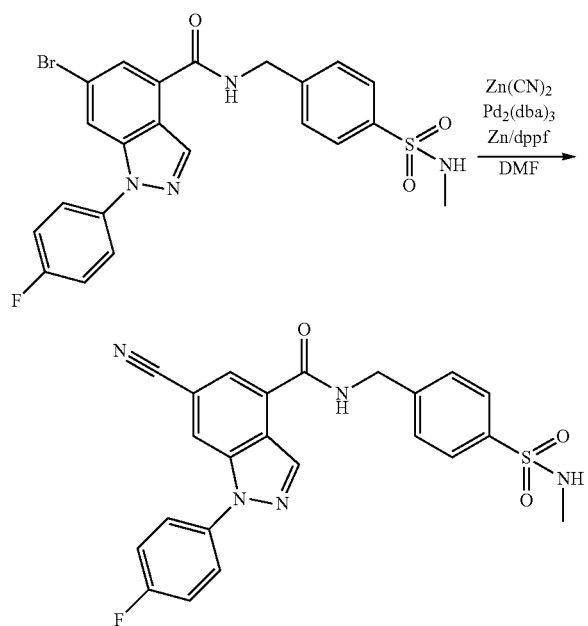

24

A mixture of 6-bromo-1-(4-fluoro-phenyl)-1H-indazole-4-carboxylic acid 4-methylsulfamoyl-benzylamide (0.04 g, 0.08 mmol), Pd$_2$(dba)$_3$ (0.009 g, 0.01 mmol), 1,1-bis(diphenylphosphino)ferrocene (dppf) (0.005 g, 0.01 mmol), zinc cyanide (0.01 g, 0.09 mmol) and zinc powder (0.002 g, 0.02 mmol) were charged in a sealed tube with anhydrous DMF (3 mL) at room temperature. The reaction mixture was heated at 120° C. for 3 hours. The solution was cooled to room temperature and diluted with saturated aqueous ammonium chloride (10 mL) and ethyl acetate (20 mL). The organic layer was separated and washed with brine (10 mL) and dried over sodium sulfate. The solvent was removed in vacuo. The residue was purified by silica gel chromatography eluting with a gradient of 20-70% ethyl acetate in hexanes to afford the title compound.

Example 25

Synthesis of 1-(4-Fluoro-phenyl)-6-methanesulfonyl-1H-indazole-4-carboxylic acid 4-methylsulfamoyl-benzylamide (25)

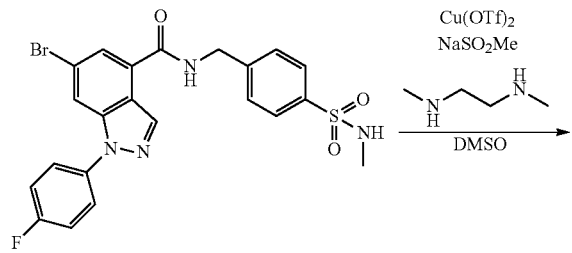

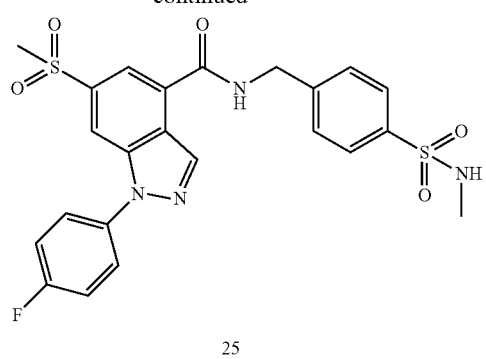

25

A mixture of 6-bromo-1-(4-fluoro-phenyl)-1H-indazole-4-carboxylic acid 4-methylsulfamoyl-benzylamide (0.07 g, 0.1 mmol), copper(II) triflate (0.05 g, 0.1 mmol), N,N'-dimethylethylenediamine (0.04 mL, 0.4 mmol), sodium methanesulfinate (0.02 g, 0.2 mmol) was charged in a sealed tube with DMSO (5 mL). The tube was capped and the solution was degassed with argon for 5 minutes. The mixture was heated in a microwave at 110° C. for 40 minutes and cooled to room temperature. The solution was diluted with ethyl acetate (30 mL) and washed with saturated aqueous ammonium chloride (10 mL), saturated aqueous NaHCO$_3$ (5 mL) and brine (5 mL) and dried over sodium sulfate. The solvent was removed in vacuo. The residue was purified by silica gel chromatography eluting with a gradient of 20-50% ethyl acetate in hexanes to afford the title compound.

Example 26

Synthesis of 1-(4-Fluoro-phenyl)-6-hydroxy-1H-indazole-4-carboxylic acid 4-methylsulfamoyl-benzylamide (26)

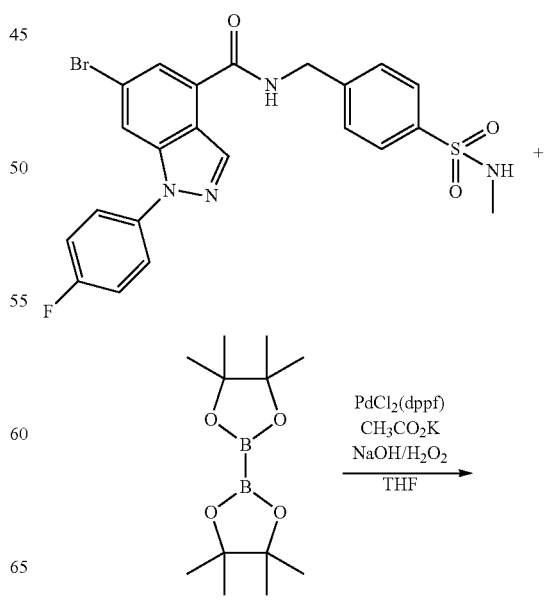

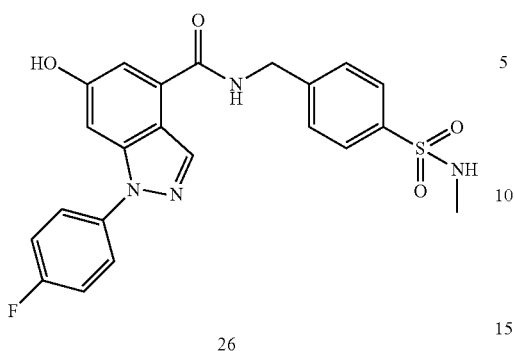

26

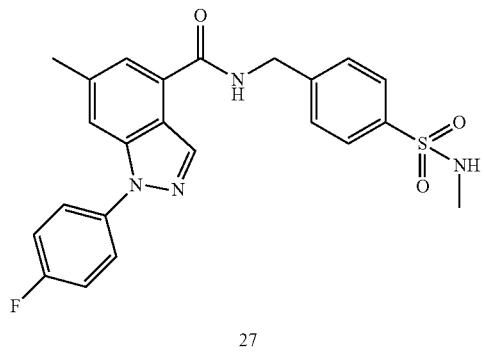

27

A mixture of 6-bromo-1-(4-fluoro-phenyl)-1H-indazole-4-carboxylic acid 4-methylsulfamoyl-benzylamide (0.1 g, 0.2 mmol), bis(pinacolato)diboron (0.1 g, 0.4 mmol), PdCl$_2$ (dppf) (0.04 g, 0.05 mmol), potassium acetate (0.05 g, 0.5 mmol) was charged in a sealed tube with anhydrous THF (7 mL). The solution was warmed at 80° C. for 16 hours. The reaction mixture was cooled to room temperature and quenched with water (15 mL) and diluted with CH$_2$Cl$_2$ (20 mL). The organic layer was separated and washed with brine (10 mL) and dried over sodium sulfate. The solvent was removed in vacuo. The residue was dissolved in THF (10 mL), and a solution of 30% H$_2$O$_2$ in water (0.15 mL, 0.5 mmol) and NaOH (0.01 g, 0.3 mmol) were added. The mixture was stirred at 10° C. for 3 hours and then quenched with water (10 mL) and diluted with CH$_2$Cl$_2$ (20 mL). The organic layer was washed with brine (10 mL) and dried over sodium sulfate. The solvent was removed in vacuo. The residue was purified by reversed-phase HPLC, eluting with a gradient of 5-100% CH$_3$CN in water. The desired fractions were combined and diluted with saturated aqueous NaHCO$_3$ (20 mL) and ethyl acetate (20 mL). The organic layer was separated, dried over sodium sulfate and concentrated to afford the title compound.

A mixture of 6-bromo-1-(4-fluoro-phenyl)-1H-indazole-4-carboxylic acid 4-methylsulfamoyl-benzylamide (0.05 g, 0.1 mmol), methylboronic acid (0.01 g, 0.2 mmol), tetrakis (triphenylphosphine)palladium (0.06 g, 0.05 mmol) and a solution of 2 N aqueous sodium carbonate (0.1 mL, 0.2 mmol) was added in a sealed tube with DMF (5 mL). The tube was capped and the resulting solution was degassed with argon for 5 minutes. The reaction was heated to 120° C. by microwave irradiation for 2.5 hours. The reaction was cooled to room temperature and quenched with saturated aqueous ammonium chloride (5 mL) and diluted with ethyl acetate (20 mL). The organic layer was separated, washed with brine (10 mL) and dried over sodium sulfate and concentrated. The residue was purified by silica gel chromatography eluting with a gradient of 20-50% ethyl acetate in hexanes to afford the title compound.

Example 28

Synthesis of 1-(4-Fluoro-phenyl)-6-methylamino-1H-indazole-4-carboxylic acid 4-methylsulfamoyl-benzylamide (28)

Example 27

Synthesis of 1-(4-Fluoro-phenyl)-6-methyl-1H-indazole-4-carboxylic acid 4-methylsulfamoyl-benzylamide (27)

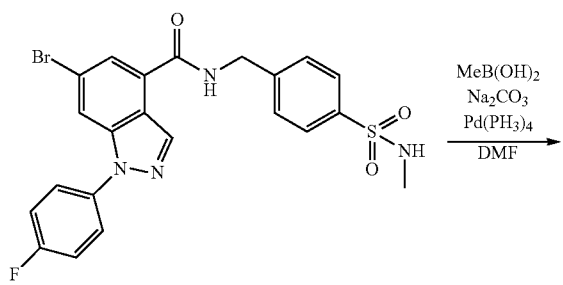

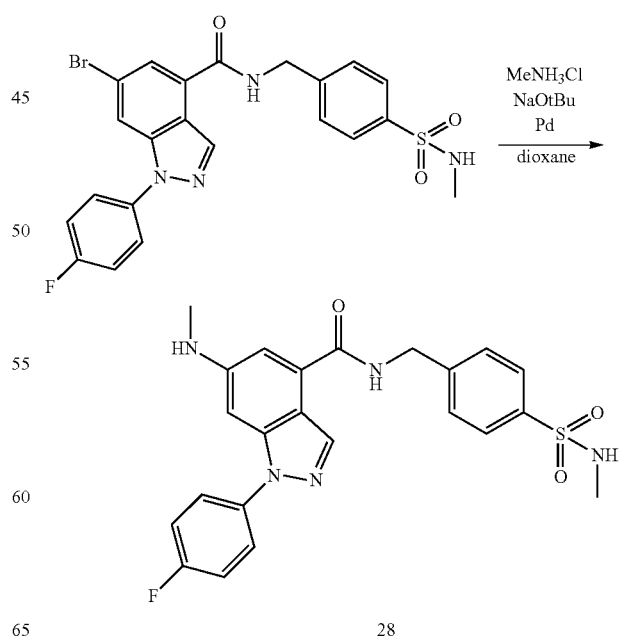

28

A mixture of 6-bromo-1-(4-fluoro-phenyl)-1H-indazole-4-carboxylic acid 4-methylsulfamoyl-benzylamide (0.05 g, 0.1 mmol), methylamine hydrochloride (0.01 g, 0.2 mmol), palladium(II) acetate di-t-butylbiphenylphosphine (0.005 g, 0.01 mmol) and sodium t-butoxide (0.03 g, 0.25 mmol) was charged in a sealed tube with dioxane (5 mL). The tube was capped, degassed with argon for 5 minutes and warmed at 90° C. for 2 hours. The reaction was cooled to room temperature and filtered through diatomaceous earth, and diluted with water (5 mL) and ethyl acetate (20 mL). The organic layer was separated and washed with brine (10 mL), dried over sodium sulfate, and concentrated. The residue was purified by reversed-phase HPLC eluting with a gradient of 5-100% $CH_3CN$ in water. The desired fractions were combined and diluted with saturated aqueous $NaHCO_3$ (20 mL) and ethyl acetate (20 mL). The organic layer was separated, dried over sodium sulfate and concentrated to afford the title compound.

The following compounds were also prepared by methods described in Example 28:
1-(4-Fluoro-phenyl)-6-[(2-methoxy-ethyl)-methyl-amino]-1H-indazole-4-carboxylic acid 4-methylsulfamoyl-benzylamide,
6-Dimethylamino-1-(4-fluoro-phenyl)-1H-indazole-4-carboxylic acid 4-methylsulfamoyl-benzylamide, and
6-(2-Dimethylamino-ethylamino)-1-(4-fluoro-phenyl)-1H-indazole-4-carboxylic acid 4-methylsulfamoyl-benzylamide.

Example 29

Synthesis of 1-(4-Fluoro-phenyl)-4-(4-methylsulfamoyl-benzylcarbamoyl)-1H-indazole-6-carboxylic acid ethyl ester (29)

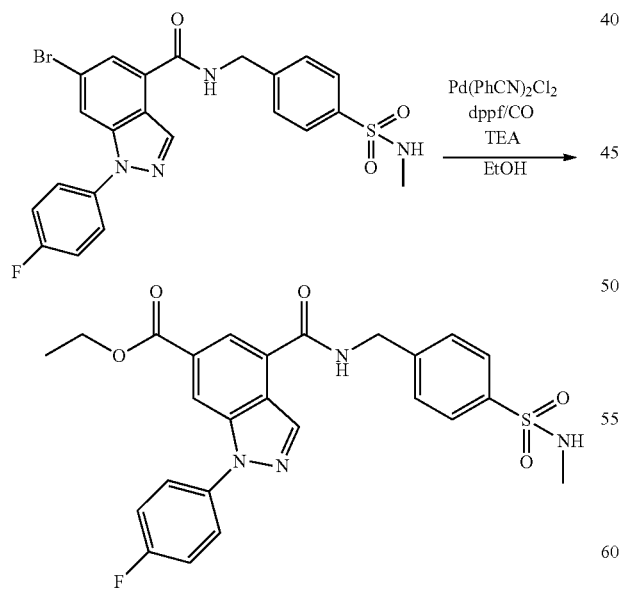

29

A mixture of 6-bromo-1-(4-fluoro-phenyl)-1H-indazole-4-carboxylic acid 4-methylsulfamoyl-benzylamide (0.2 g, 0.4 mmol), triethylamine (0.1 g, 0.9 mmol), dichlorobis(benzonitrile)palladium (0.02 g, 0.05 mmol) and 1,1-bis(diphenylphosphino)ferrocene (0.03 g, 0.05 mmol) was charged in a sealed tube with absolute ethanol (15 mL). The solution was placed under 15 bars of carbon monoxide and warmed at 140° C. for 4 hours. The mixture was cooled to room temperature and returned to atmospheric pressure. The reaction was diluted with water (30 mL) and the solid was collected by filtration. The filtrate was diluted with water (20 mL) and ethyl acetate (20 mL). The organic layer was separated and washed with brine (10 mL) and dried over sodium sulfate and concentrated. The residue was purified by silica gel chromatography eluting with a gradient of 30-70% ethyl acetate in hexanes to afford the title compound.

Example 30

Synthesis of 1-(4-Fluoro-phenyl)-4-(4-methylsulfamoyl-benzylcarbamoyl)-1H-indazole-6-carboxylic acid (30)

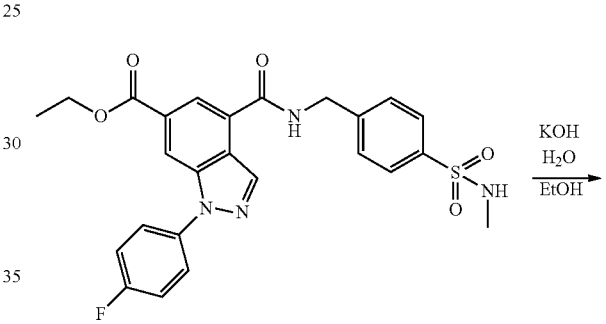

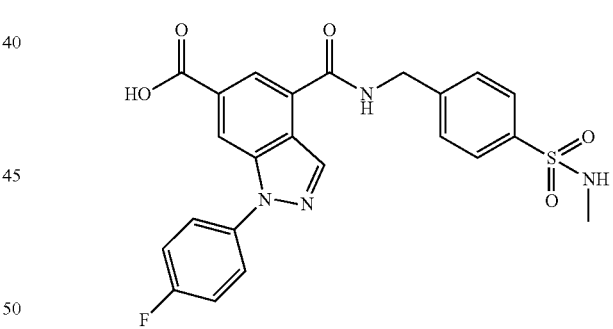

30

To a stirred solution of 1-(4-fluoro-phenyl)-4-(4-methylsulfamoyl-benzylcarbamoyl)-1H-indazole-6-carboxylic acid ethyl ester (0.13 g, 0.26 mmol) in $H_2O$ (10 mL) and EtOH (20 mL) was added a 2 N solution of aqueous KOH (10 mL, 20 mmol). The mixture was warmed at reflux for 1 hour and cooled to room temperature. The mixture was acidified with 2 N aqueous HCl (pH=3-4) and diluted with ethyl acetate (30 mL). The organic layer was separated and washed with brine (20 mL), dried over sodium sulfate, filtered and concentrated. The residue was triturated with diethyl ether (10 mL) to afford the title compound.

Example 31

Synthesis of 1-(4-Fluoro-phenyl)-1H-indazole-4,6-dicarboxylic acid 6-methylamide 4-(4-methylsulfamoyl-benzylamide) (31)

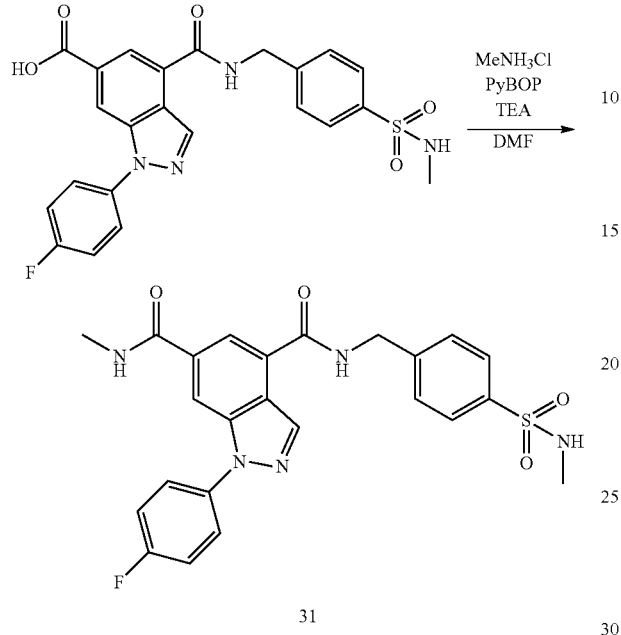

To a stirred solution of 1-(4-fluoro-phenyl)-4-(4-methyl-sulfamoyl-benzylcarbamoyl)-1H-indazole-6-carboxylic acid (0.04 g, 0.1 mmol) in DMF (20 mL) was added PyBOP (0.05 g, 0.2 mmol) and TEA (0.03 g, 0.2 mmol) at room temperature. The resulting solution was stirred for 15 minutes and then methylamine hydrochloride (0.007 g, 0.2 mmol) was added. The reaction was stirred for 5 hours and diluted with water (20 mL) and ethyl acetate (30 mL). The organic layer was separated and washed with brine (10 mL), dried over sodium sulfate and concentrated in vacuo. The residue was purified by silica gel chromatography eluting with a gradient of 30-50% ethyl acetate in hexanes afford the title compound.

The following compound was also prepared by methods described in Example 31:
1-(4-Fluoro-phenyl)-1H-indazole-4,6-dicarboxylic acid 6-[(2-hydroxy-ethyl)-amide]-4-(4-methylsulfamoyl-benzylamide).

Example 32

Synthesis of 6-Cyano-1-(4-fluoro-phenyl)-1H-indazole-4-carboxylic acid 4-(1-methyl-piperidin-4-yl-sulfamoyl)-benzylamide (32)

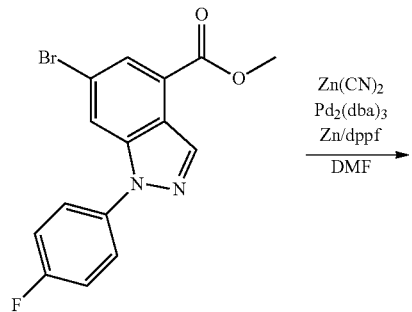

-continued

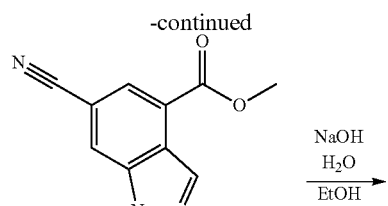

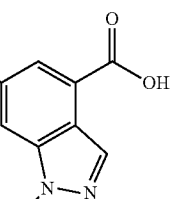

+

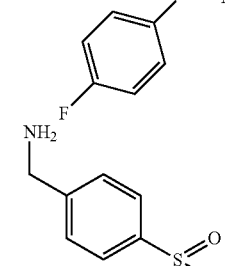

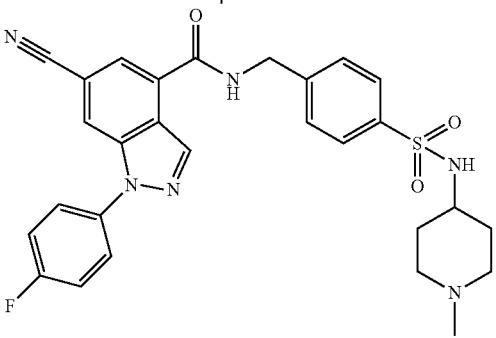

32

A sealed tube was charged with 6-bromo-1-(4-fluoro-phenyl)-1H-indazole-4-carboxylic acid methyl ester (1.5 g, 4.3 mmol), $Pd_2(dba)_3$ (0.4 g, 0.4 mmol), zinc cyanide (0.6 g, 5 mmol), dppf (0.3 g, 0.4 mmol) and zinc powder (0.2 g, 3 mmol) and DMF (20 mL). The reaction solution was degassed with argon for 15 minutes and warmed at 120° C. for 3 hours. The reaction was cooled to room temperature, diluted with saturated aqueous ammonium chloride (10 mL) and ethyl acetate (50 mL). The organic layer was separated and washed with brine (10 mL), dried over sodium sulfate, filtered and concentrated. The residue was purified by silica gel chromatography eluting with a gradient of 0-20% ethyl acetate in hexanes to afford 6-cyano-1-(4-fluoro-phenyl)-1H-indazole-4-carboxylic acid methyl ester.

To a stirred solution of 6-cyano-1-(4-fluoro-phenyl)-1H-indazole-4-carboxylic acid methyl ester (0.30 g, 1.1 mmol) in water (10 mL) and methanol (10 mL) was added a 2 N aqueous sodium hydroxide (10 mL, 20 mmol). The mixture was warmed at reflux for 1 hour, cooled to room temperature, and acidified with 1 N aqueous HCl (pH=3-4). The white solid was collected by filtration, washed with MeOH (10 mL) and dried to afford 6-cyano-1-(4-fluoro-phenyl)-1H-indazole-4-carboxylic acid.

To a stirred solution of 6-cyano-1-(4-fluoro-phenyl)-1H-indazole-4-carboxylic acid (0.040 g, 0.14 mmol) in DMF (15 mL) was added PyBOP (0.1 g, 0.2 mmol) and triethylamine (0.04 g, 0.3 mmol) at room temperature. After 15 minutes, 4-aminomethyl-N-(1-methyl-piperidin-4-yl)-benzene-sulfonamide (0.05 g, 0.16 mmol) was added. After 5 hours, the mixture was diluted with water (30 mL) and ethyl acetate (30 mL). The organic layer separated and washed with brine (20 mL), dried over sodium sulfate, filtered and concentrated. The residue was purified by silica gel chromatography eluting with a gradient of 30-50% ethyl acetate in hexanes to afford the title compound.

The following compounds were also prepared by methods described in Example 32:

6-Cyano-1-(4-fluoro-phenyl)-1H-indazole-4-carboxylic acid 3-methanesulfonyl-benzylamide, 6-Cyano-1-(4-fluoro-phenyl)-1H-indazole-4-carboxylic acid (6-bromo-pyridin-3-ylmethyl)-amide, 6-Cyano-1-(4-fluoro-phenyl)-1H-indazole-4-carboxylic acid (6-methanesulfonyl-pyridin-3-ylmethyl)-amide, 6-Cyano-1-(4-fluoro-phenyl)-1H-indazole-4-carboxylic acid (6-methanesulfonylamino-pyridin-3-ylmethyl)-amide, 6-Cyano-1-(4-fluoro-phenyl)-1H-indazole-4-carboxylic acid 4-(4-methyl-piperazine-1-sulfonyl)-benzylamide, and 6-Cyano-1-(4-fluoro-phenyl)-1H-indazole-4-carboxylic acid 4-[methyl-(1-methyl-piperidin-4-yl)-sulfamoyl]-benzylamide.

Example 33

Synthesis of 1-(4-Fluoro-phenyl)-1H-indazole-4-carboxylic acid [(S)-1-(6-bromo-pyridin-3-yl)-propyl]-amide (33)

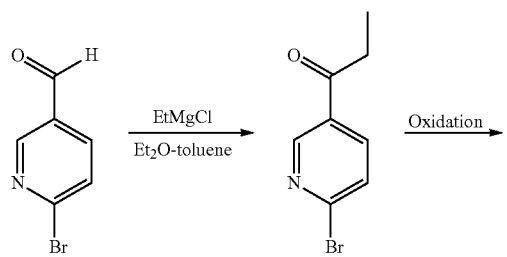

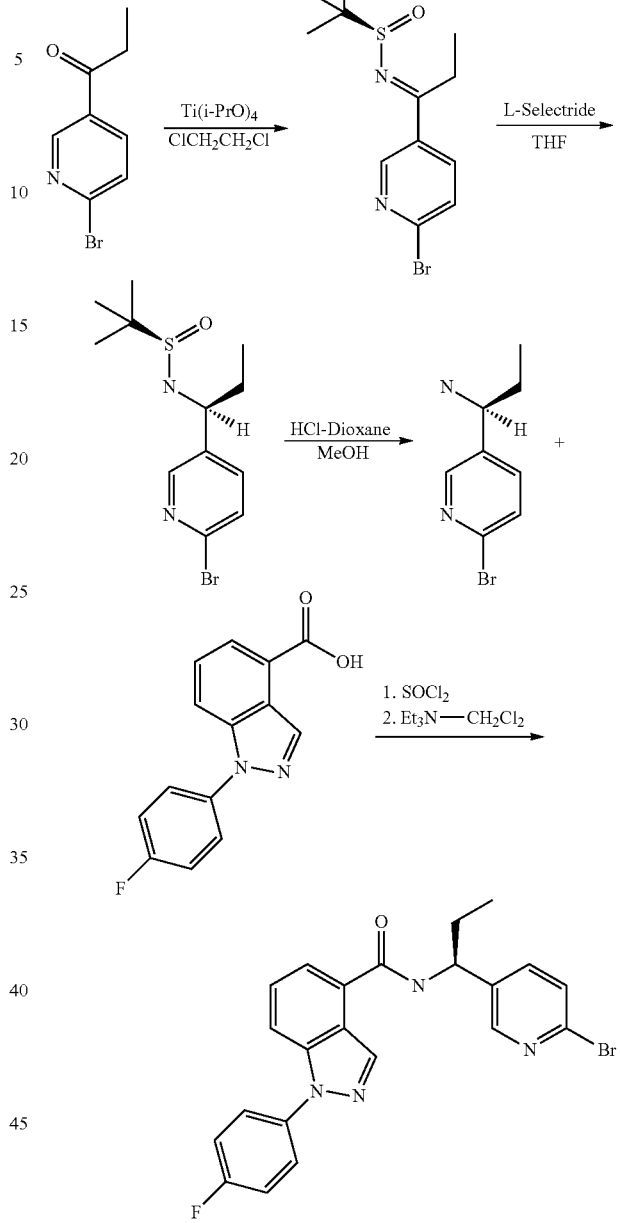

To a chilled (0° C.) solution of 6-bromo-pyridine-3-carboxaldehyde (15.0 g, 80.6 mmol) in a 1:1 mixture of ether-toluene (400 mL) was added a 2 M solution of ethyl magnesium chloride (40.0 mL, 80.0 mmol) in THF over a 15 minute period. The solution was stirred for 4 hours, and a more polar product was observed by TLC (ethyl acetate-hexanes 3:7). The mixture was diluted with saturated aqueous ammonium chloride (300 mL) and the organic phase separated. The aqueous layer was extracted with ethyl acetate (2×100 mL). The combined organic layers were washed with brine (2×50 mL), dried over magnesium sulfate, filtered and concentrated. The crude material was passed through a pad of silica gel eluting 0-100% dichloromethane in hexanes. The material from the pad was purified by silica gel chromatography eluting with a gradient of 2-15% ethyl acetate in hexanes to afford 1-(6-bromo-pyridin-3-yl)-propan-1-ol.

To a solution of 1-(6-bromo-pyridin-3-yl)-propan-1-ol (12.95 g, 59.93 mmol) in THF (200 mL) was added activated MnO$_2$ (6.4 g, 63 mmol). The mixture was stirred at room temperature overnight. The reaction was monitored by TLC (ethyl acetate-hexanes 4:6) indicating starting material and a new less polar product. To the mixture was added additional MnO$_2$ (6.0 g, 59 mmol) and the mixture stirred over the weekend. The reaction was monitored by TLC (ethyl acetate-hexanes 3:7) indicting starting material was still present. The mixture was warmed at reflux for 6 hours. Starting material was still evident by TLC. The mixture was filtered through diatomaceous earth and concentrated. The resulting solid was triturated with diethylether to afford 4 grams of white solid. The filtrate was concentrated dissolved in dichloromethane and combined with the 4 grams of solid and the Dess-Martin periodinane (19 g, 44.8 mmol) was added. The mixture was stirred for 1 hour and was then diluted with saturated aqueous potassium carbonate (200 mL) and concentrated. The resulting solid was collected by filtration, washed with water and dried in the funnel by pulling vacuum overnight. The solid was then suspended in dichloromethane and filtered. The filtrate was collected and passed through a pad of silica gel eluting with diethylether to afford 1-(6-bromo-pyridin-3-yl)-propan-1-one.

A mixture of 1-(6-bromo-pyridin-3-yl)-propan-1-one (11.8 g, 55.1 mmol), (R)-(+)-2-methyl-2-propanesulfinamide (8.0 g, 66 mmol) and titanium isopropoxide (18.0 mL, 61.4 mmol) in dichloroethane (65 mL) was warmed at reflux for 2 days. The reaction was monitored by TLC (ethyl acetate-hexanes 2:8) indicating a new more polar product than starting ketone, however ketone was still evident. The mixture was diluted with first dichloromethane (600 mL) and then water (15 mL) was added. The mixture was stirred for 10 minutes and then magnesium sulfate added. The mixture was filtered through diatomaceous earth and concentrated. The residue was purified by silica gel chromatography eluting with a gradient of 0-40% ethyl acetate in hexanes and then a gradient of 0-40% ethyl acetate in dichloromethane to afford 2-methyl-propane-2-sulfinic acid [1-(6-bromo-pyridin-3-yl)-prop-(E)-ylidene]-amide.

To a chilled (−78° C.) solution of 2-methyl-propane-2-sulfinic acid [1-(6-bromo-pyridin-3-yl)-prop-(E)-ylidene]-amide (10.4 g, 32.8 mmol) in THF (150 mL) was added a 1 N solution of lithium tri-sec-butylborohydride (L-Selectride) (33.0 mL, 33.0 mmol) in THF. The reaction was monitored by TLC (ethyl acetate-ether 3:7) indicating a single diastereomer when compared to a mixture of diastereomers prepared by reduction with lithium borohydride in THF. After 6 hours, the mixture was quenched with saturated aqueous ammonium chloride (100 mL) and extracted with ethyl acetate (3×100 mL). The combined organic layers were washed with saturated aqueous ammonium chloride (2×50 mL), brine (50 mL), dried over magnesium sulfate, filtered and concentrated. The crude material was purified by silica gel chromatography eluting with a gradient of 0-20% diethylether in dichloromethane to afford 7.5 g of material which was triturated with diethylether to afford in two crops 2-methyl-propane-2-sulfinic acid [(S)-1-(6-bromo-pyridin-3-yl)-propyl]-amide which was consistent with a single diastereomer by $^1$H NMR. This material and the filtrate were purified separately by silica gel chromatography using a gradient of 0-40% ethyl acetate in dichloromethane. The material from the columns was recrystallized from dichloromethane-hexanes-ether to afford in 3 crops 2-methyl-propane-2-sulfinic acid [(S)-1-(6-bromo-pyridin-3-yl)-propyl]-amide which was consistent with a single diastereomer.

To a solution of 2-methyl-propane-2-sulfinic acid [(S)-1-(6-bromo-pyridin-3-yl)-propyl]-amide (5.35 g, 16.8 mmol) in methanol (25 mL) was added a solution of 4 N HCl in dioxane (10.0 mL, 40.0 mmol). The mixture was monitored by TLC for the disappearance of starting material (ethyl acetate-hexanes 3:7). After 2 hours, the mixture was concentrated to near dryness to afford a white solid which was diluted with diethylether and collected by filtration to afford (S)-1-(6-bromo-pyridin-3-yl)-propylamine hydrochloride.

A suspension of 1-(4-fluoro-phenyl)-1H-indazole-4-carboxylic acid (258 mg, 1.00 mmol) was heated at reflux in thionyl chloride (5 mL) until the solid dissolved. After 45 minutes, the mixture was concentrated to dryness. The yellow residue was diluted with dichloromethane and (S)-1-(6-bromo-pyridin-3-yl)-propylamine hydrochloride (288 mg, 1.00 mmol) was added followed by triethylamine (1.0 mL, 7.2 mmol). After 30 minutes, the reaction was diluted with saturated aqueous ammonium chloride (10 mL) and extracted with ethyl acetate (4×10 mL). The combined organic layers were washed with brine (3×10 mL), dried over magnesium sulfate, filtered and concentrated. The crude material was diluted with dichloromethane and purified by silica gel chromatography eluting with a gradient of 0-100% ethyl acetate in hexanes. The material from the column was triturated with ether to afford 1-(4-fluoro-phenyl)-1H-indazole-4-carboxylic acid [(S)-1-(6-bromo-pyridin-3-yl)-propyl]-amide.

1-(4-Fluoro-phenyl)-1H-indazole-4-carboxylic acid [(S)-1-(6-bromo-pyridin-3-yl)-propyl]-amide was converted to 1-(4-fluoro-phenyl)-1H-indazole-4-carboxylic acid [(S)-1-(6-methanesulfonyl-pyridin-3-yl)-propyl]-amide as described in Example 7.

Example 34

Synthesis of 6-Bromo-1-(4-fluoro-phenyl)-1H-indazole-4-carboxylic acid [(S)-1-(6-methanesulfonyl-pyridin-3-yl)-propyl]-amide (34) and 1-(4-Fluoro-phenyl)-6-methanesulfonyl-1H-indazole-4-carboxylic acid [(S)-1-(6-methanesulfonyl-pyridin-3-yl)-propyl]-amide (35)

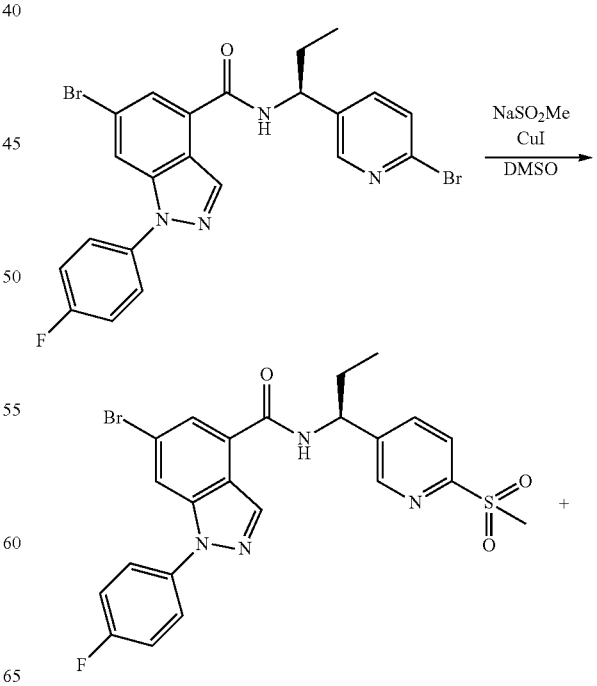

34

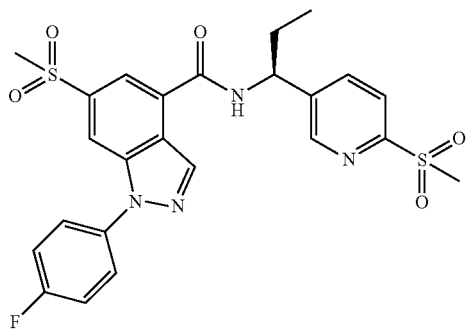

A microwave tube was charged with 6-bromo-1-(4-fluorophenyl)-1H-indazole-4-carboxylic acid [(S)-1-(6-bromo-pyridin-3-yl)-propyl]-amide (90.0 mg, 0.170 mmol, prepared as described in Example 23), copper (I) iodide (143 mg, 0.75 mmol) and sodium methanesulfinate (77.0 mg, 0.75 mmol) in DMSO (20 mL). The tube was capped and the solution was degassed with argon for 3 minutes. The mixture was warmed in the microwave at 130° C. After 40 minutes, the reaction was diluted with saturated aqueous ammonium chloride (100 mL), saturated aqueous sodium bicarbonate (50 mL) and extracted with ethyl acetate. The combined organic layers were washed with brine, dried over sodium sulfate and concentrated in vacuo. The crude mixture was purified via reversed-phase HPLC to afford the title compounds.

ASSESSMENT OF BIOLOGICAL PROPERTIES

Compounds are assessed for the ability to block the interaction of CCR1 and its ligand in a functional cellular assay measuring calcium flux in response to MIP-1α in CCR1-transfected cells.

Method A: Non-adherent cells purchased from Chemicon Corporation (HTS005C), stably expressing recombinant CCR1 and G-alpha-16 are grown in RPMI 1640 medium (Mediatech 10-080-CM) supplemented with 10% heat-inactivated FBS, 0.4 mg/mL Geneticin and penicillin/streptomycin. On the day of the assay, the cells are transferred to a beaker and dye-loaded in bulk using a Fluo-4 NW Calcium Assay Kit with probenecid (Invitrogen F36205) at 0.8E6 cells/mL for 1 hour at room temperature. After 1 hour, they are seeded in a 384-well tissue culture-treated plate at a density of 20,000 cells/well. Appropriately diluted test compound is added to the well to achieve a top concentration of 3,000 nM (diluted 3-fold with 10 doses total). The final concentration of DMSO is 1%. The buffer is HBSS (Invitrogen 14025) with 20 mM HEPES at pH 7.4. The cells are allowed to incubate 1 hour in the dark at room temperature. The plates are transferred to the FLIPR TETRA where MIP-1 alpha in 1% BSA is added at the EC80 final concentration. Wells +/− MIP-1 alpha containing diluted DMSO instead of compound serve as the controls. Intracellular calcium flux is recorded on the FLIPR TETRA, using excitation at 470/495 nm and emission at 515/575 nm Data are analyzed using Activity Base software.

Method B: Non-adherent cells purchased from Chemicon Corporation (HTS005C), stably expressing recombinant CCR1 and G-alpha-16 are grown in RPMI 1640 medium (Mediatech 10-080-CM) supplemented with 10% FBS, 0.4 mg/mL Geneticin and penicillin/streptomycin. On the day of the assay, the cells are loaded with Calcium 4 dye (Molecular Devices R7448) with Probenecid (Invitrogen P346400) at 8E5 cells/mL for 1 hour at room temperature. After 1 hour, they are seeded in a 384-well tissue culture-treated plate at a density of 20,000 cells/well. Appropriately diluted test compound is added to the well to achieve a top concentration of 3,000 nM (diluted 4-fold with 10 doses total). The final concentration of DMSO is 1%. The buffer is HBSS (Invitrogen 14025) with 20 mM HEPES at pH 7.4. The cells incubate 30 minutes at 37 C and then 30 minutes at room temperature. The plates are transferred to the HAMAMATSU FDSS6000 where MIP-1alpha in 1% BSA is added at the EC80 final concentration. All plates must be read within 4 hours of the start of dye-loading. Wells +/− MIP-1alpha containing diluted DMSO instead of compound serve as the controls. Data are analyzed using Activity Base software.

In general, the preferred potency range ($IC_{50}$) of compounds in the above assays is between 0.1 nM to 10 μM, the more preferred potency range is 0.1 nM to 1 μM, and the most preferred potency range is 0.1 nM to 100 nM.

Representative compounds of the invention have been tested in the above assay and have shown activity as CCR1 antagonists.

TABLE II (Method A)

| Name | Method A $IC_{50}$ (nM) |
|---|---|
| 1-(4-Fluoro-phenyl)-1H-indazole-4-carboxylic acid 3,5-dimethoxy-benzylamide | 25 |
| 1-(4-Fluoro-phenyl)-1H-indazole-4-carboxylic acid 4-methanesulfonyl-benzylamide | 68 |
| 1-(4-Fluoro-phenyl)-1H-indazole-4-carboxylic acid 3-bromo-benzylamide | 76 |
| 1-(4-Fluoro-phenyl)-1H-indazole-4-carboxylic acid 3-methanesulfonyl-benzylamide | 61 |
| 1-(4-Fluoro-phenyl)-1H-indazole-4-carboxylic acid 2-chloro-4-methylsulfamoyl-benzylamide | 4.0 |
| 1-(4-Fluoro-phenyl)-1H-indazole-4-carboxylic acid [(S)-1-(3-bromo-phenyl)-butyl]-amide | 19 |
| 1-(4-Fluoro-phenyl)-1H-indazole-4-carboxylic acid [1-(3-trifluoromethyl-phenyl)-ethyl]-amide | 14 |
| 1-(4-Fluoro-phenyl)-1H-indazole-4-carboxylic acid 2-chloro-4-methanesulfonyl-benzylamide | 6.7 |
| 1-(4-Fluoro-phenyl)-1H-indazole-4-carboxylic acid 3-trifluoromethyl-benzylamide, | 22 |
| 1-(6-Fluoro-pyridin-3-yl)-1H-indazole-4-carboxylic acid 3-trifluoromethyl-benzylamide | 17 |
| 1-(4-Fluoro-phenyl)-1H-indazole-4-carboxylic acid (2-methoxy-pyridin-4-ylmethyl)-amide | 22 |
| 1-(4-Fluoro-phenyl)-1H-indazole-4-carboxylic acid 2-fluoro-4-methylsulfamoyl-benzylamide | 5.4 |
| 1-(4-Fluoro-phenyl)-1H-indazole-4-carboxylic acid (2-cyano-pyridin-4-ylmethyl)-amide | 120 |
| 1-(4-Fluoro-phenyl)-1H-indazole-4-carboxylic acid 4-methylsulfamoyl-benzylamide | 4.5 |
| 1-(4-Fluoro-phenyl)-1H-indazole-4-carboxylic acid 4-(morpholine-4-sulfonyl)-benzylamide | 14 |
| 1-(4-Fluoro-phenyl)-1H-indazole-4-carboxylic acid 4-dimethylsulfamoyl-benzylamide | 5.6 |
| 1-(4-Fluoro-phenyl)-1H-indazole-4-carboxylic acid 4-isopropylsulfamoyl-benzylamide | 5.5 |
| 1-(4-Fluoro-phenyl)-1H-indazole-4-carboxylic acid 4-(2-methoxy-ethylsulfamoyl)-benzylamide | 10 |
| 1-(4-Fluoro-phenyl)-6-methanesulfonyl-1H-indazole-4-carboxylic acid 4-methylsulfamoyl-benzylamide | 28 |
| 6-Cyano-1-(4-fluoro-phenyl)-1H-indazole-4-carboxylic acid 4-methylsulfamoyl-benzylamide | 0.3 |
| 1-(4-Fluoro-phenyl)-6-methyl-1H-indazole-4-carboxylic acid 4-methylsulfamoyl-benzylamide | 20 |
| 1-(4-Fluoro-phenyl)-1H-indazole-4-carboxylic acid 4-(isopropylsulfamoyl-methyl)-benzylamide | 55 |

TABLE II-continued (Method A)

| Name | Method A IC$_{50}$ (nM) |
|---|---|
| 1-(4-Fluoro-phenyl)-1H-indazole-4-carboxylic acid 4-(2-hydroxy-ethylsulfamoyl)-benzylamide | 9.2 |
| 1-(4-Fluoro-phenyl)-1H-indazole-4-carboxylic acid 4-(2-acetylamino-ethylsulfamoyl)-benzylamide | 110 |
| 1-(4-Fluoro-phenyl)-1H-indazole-4-carboxylic acid 4-(4-methyl-piperazine-1-sulfonyl)-benzylamide | 12 |
| 1-(4-Fluoro-phenyl)-1H-indazole-4-carboxylic acid 4-(tetrahydro-pyran-4-ylsulfamoyl)-benzylamide | 20 |
| [4-({[1-(4-Fluoro-phenyl)-1H-indazole-4-carbonyl]-amino}-methyl)-pyridin-2-yloxy]-acetic acid ethyl ester | 140 |
| 1-(4-Fluoro-phenyl)-1H-indazole-4-carboxylic acid 4-[methyl-(1-methyl-piperidin-4-yl)-sulfamoyl]-benzylamide | 44 |
| 1-(4-Fluoro-phenyl)-1H-indazole-4-carboxylic acid 4-(4-dimethylamino-piperidine-1-sulfonyl)-benzylamide | 23 |
| 6-Cyano-1-(4-fluoro-phenyl)-1H-indazole-4-carboxylic acid 3-methanesulfonyl-benzylamide | 2.0 |
| 6-Cyano-1-(4-fluoro-phenyl)-1H-indazole-4-carboxylic acid (6-bromo-pyridin-3-ylmethyl)-amide | 21 |
| 1-(4-Fluoro-phenyl)-1H-indazole-4-carboxylic acid 3-methylsulfamoyl-benzylamide | 55 |
| 1-(4-Fluoro-phenyl)-1H-indazole-4-carboxylic acid 3-dimethylsulfamoyl-benzylamide | 45 |
| 6-Cyano-1-(4-fluoro-phenyl)-1H-indazole-4-carboxylic acid (6-methanesulfonyl-pyridin-3-ylmethyl)-amide | 7.1 |
| 6-Cyano-1-(4-fluoro-phenyl)-1H-indazole-4-carboxylic acid 4-(4-methyl-piperazine-1-sulfonyl)-benzylamide | 1.5 |
| 6-Cyano-1-(4-fluoro-phenyl)-1H-indazole-4-carboxylic acid (6-methanesulfonylamino-pyridin-3-ylmethyl)-amide | 4.4 |
| 6-Cyano-1-(4-fluoro-phenyl)-1H-indazole-4-carboxylic acid 4-(1-methyl-piperidin-4-ylsulfamoyl)-benzylamide | 18 |
| 6-Cyano-1-(4-fluoro-phenyl)-1H-indazole-4-carboxylic acid 4-[methyl-(1-methyl-piperidin-4-yl)-sulfamoyl]-benzylamide | 5.1 |

TABLE III (Method B)

| Name | Method B IC$_{50}$ (nM) |
|---|---|
| 1-(4-Fluoro-phenyl)-1H-indazole-4-carboxylic acid [(S)-1-(6-methanesulfonyl-pyridin-3-yl)-propyl]-amide | 2 |
| 6-Bromo-1-(4-fluoro-phenyl)-1H-indazole-4-carboxylic acid [(S)-1-(6-methanesulfonyl-pyridin-3-yl)-propyl]-amide | 23 |

METHOD OF USE

The compounds of the invention are effective antagonists of the interactions between CCR1 and its chemokine ligands and thus inhibit CCR1-mediated activity. Therefore, in one embodiment of the invention, there is provided methods of treating autoimmune disorders using compounds of the invention. In another embodiment, there is provided methods of treating inflammatory disorders using compounds of the invention.

Without wishing to be bound by theory, by antagonizing the interactions between CCR1 and its chemokine ligands, the compounds block chemotaxis of pro-inflammatory cells including monocytes, macrophages dendritic cells, eosinophils, and T cells (TH1) cells and other CCR1 positive cells to inflamed tissues and thereby ameliorate the chronic inflammation associated with autoimmune diseases. Thus, the inhibition of CCR1 activity is an attractive means for preventing and treating a variety of autoimmune disorders, including inflammatory diseases, autoimmune diseases, organ (Horuk et al. (2001) JBC 276 p. 4199) and bone marrow transplant rejection and other disorders associated with an influx of pro-inflammatory cells. For example, the compounds of the invention may be used to prevent or treat acute or chronic inflammation, allergies, contact dermatitis, psoriasis, rheumatoid arthritis, multiple sclerosis, type 1 diabetes, inflammatory bowel disease, Guillain-Barre syndrome, Crohn's disease, ulcerative colitis, graft versus host disease (and other forms of organ or bone marrow transplant rejection), Alzheimer's disease (Halks-Miller et al. (2003) Ann Neurol 54 p. 638), Asthma (Jouber et al. (2008) J. Immun 180 p. 1268) chronic kidney disease (Topham et al. (1999) J. Clin. Invest. 104 p. 1549), sepsis (He et al. (2007) Am J. Physio 292 p. G1173), autoimmune myocarditis (Futamats et al. (2006) J Mol Cell Cardiology 40 p. 853) and systemic lupus erythematosus. In particular, the compounds may be used to prevent or treat rheumatoid arthritis and multiple sclerosis. Other disorders associated with the trafficking of pro-inflammatory cells will be evident to those of ordinary skill in the art and can also be treated with the compounds and compositions of this invention.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased antagonist activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by Remington: The Science and Practice of Pharmacy, 20th Edition, A. Gennaro (ed.), Lippincott Williams & Wilkins, 2000; Handbook of Pharmaceutical Additives, Michael & Irene Ash (eds.), Gower, 1995; Handbook of Pharmaceutical Excipients, A. H. Kibbe (ed.), American Pharmaceutical Ass'n, 2000; H. C. Ansel and N. G. Popovish, Pharmaceutical Dosage Forms and Drug Delivery Systems, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

The invention claimed is:
1. A compound of the formula (I)

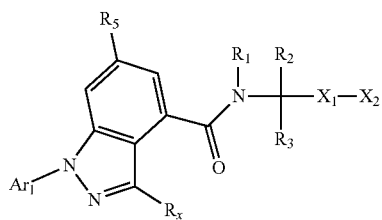

wherein
Ar$_1$ is phenyl optionally substituted by one to three R$_a$;
X$_1$ is a —(CH$_2$)$_n$— wherein one or more hydrogen atoms can be replaced by R$_a$;
X$_2$ is Ar$_2$, —S(O)$_m$—Ar$_2$ or —S(O)$_m$NR$_e$R$_f$ or —S(O)$_m$NH—Ar$_2$;
Ar$_2$ is carbocycle, heteroaryl or heterocycle each optionally substituted by one to three R$_b$;
R$_1$ is hydrogen, C$_{1-6}$ alkyl or C$_{1-6}$alkoxyC$_{1-6}$alkyl;
R$_2$, R$_3$ are each independently hydrogen or C$_{1-6}$ alkyl optionally substituted by R$_a$;
R$_a$ is C$_{1-6}$ alkyl, C$_{3-10}$ cycloalkyl, C$_{1-6}$ alkoxy, C$_{1-6}$ alkylthio, C$_{1-6}$ alkylsulfonyl, C$_{1-6}$ alkoxycarbonyl, amino, mono- or di-C$_{1-6}$ alkylamino, C$_{3-6}$ cycloalkylamino, C$_{1-6}$ alkylaminocarbonyl, C$_{1-6}$ acyl, C$_{1-6}$ acylamino, C$_{1-6}$ dialkylaminocarbonyl, hydroxyl, halogen, cyano, nitro, oxo, R$_4$—S(O)$_m$—NH—, R$_4$—NH—S(O)$_m$—, aryl or carboxyl;
R$_b$ is hydroxyl, carboxyl, halogen, —(CH$_2$)$_n$—CN, nitro, oxo, C$_{1-6}$ alkyl, C$_{2-6}$ alkenyl, C$_{2-6}$ alkynyl, C$_{3-10}$ cycloalkyl, C$_{1-6}$ alkoxy, C$_{1-6}$ alkoxycarbonyl, —(CH$_2$)$_n$—NR$_c$R$_d$, R$_4$—S(O)$_m$—, R$_4$—S(O)$_m$—NR$_e$—, R$_4$—NR$_e$—S(O)$_m$—, —NR$_f$—C(O)—R$_e$, —(CH$_2$)$_x$—C(O)—(CH$_2$)$_n$—NR$_c$R$_d$, heterocyclyl, aryl or heteroaryl, each substituent on R$_b$ where possible is optionally halogenated or substituted with 1 to 3 C$_{1-6}$ alkyl, C$_{1-6}$ acyl, C$_{1-6}$ alkoxycarbonyl, C$_{1-6}$ alkyl—S(O)$_m$—, aryl or carboxyl;
each R$_c$, R$_d$ are independently hydrogen, C$_{1-6}$ alkyl, C$_{1-6}$ acyl, C$_{3-10}$ cycloalkyl, C$_{1-6}$ alkoxy, hydroxyl C$_{1-6}$ alkyl, C$_{1-6}$ alkylC$_{1-6}$ alkoxy, C$_{1-6}$ alkylsulfonyl, C$_{1-6}$ alkoxycarbonyl or —(CH$_2$)$_n$—NR$_e$R$_f$;
each R$_e$, R$_f$ are independently hydrogen, C$_{1-6}$ alkyl, C$_{3-10}$ cycloalkyl, C$_{1-6}$ alkoxy, hydroxyC$_{1-6}$ alkyl or C$_{1-6}$ acyl;
R$_4$ is hydrogen, C$_{1-6}$ alkyl, heterocyclyl, aryl or heteroaryl each optionally substituted with C$_{1-6}$ alkyl, C$_{1-6}$ alkoxy, halogen, hydroxyl, amino, mono- or di-C$_{1-6}$ alkylamino, C$_{1-6}$ alkoxycarbonyl or C$_{1-6}$ acylamino;
R$_5$ is hydrogen or R$_a$;
R$_x$ is hydrogen or halogen;
each n, x are independently 0-3;
each m is independently 0-2;
or a pharmaceutically acceptable salt thereof.

2. The compound to claim 1 and wherein
Ar$_1$ is phenyl optionally substituted by one to three R$_a$;
X$_1$ is a —(CH$_2$)$_n$—;
Ar$_2$ is aryl, furanyl, pyranyl, benzoxazolyl, benzothiazolyl, benzimidazolyl, benzimidazolonyl, tetrahydropyranyl, dioxanyl, tetrahydrofuranyl, oxazolyl, isoxazolyl, thiazolyl, pyrazolyl, pyrrolyl, imidazolyl, thienyl, thiadiazolyl, thiomorpholinyl, 1,1-dioxo-1λ$^6$-thiomorpholinyl, morpholinyl, pyridinyl, pyridinonyl, pyrimidinyl, pyridazinyl, pyrazinyl, triazinyl, pyrrolidinyl, piperidinyl, piperazinyl, purinyl, quinolinyl, dihydro-2H-quinolinyl, isoquinolinyl, quinazolinyl, indazolyl, thieno[2,3-d]pyrimidinyl, indolyl, isoindolyl, benzofuranyl, benzopyranyl or benzodioxolyl each optionally substituted by one to three R$_b$;
R$_1$ is hydrogen or C$_{1-4}$ alkyl;
R$_2$, R$_3$ are each independently hydrogen or C$_{1-3}$ alkyl;
R$_a$ is C$_{1-5}$ alkyl, C$_{3-7}$ cycloalkyl, C$_{1-5}$ alkoxy, C$_{1-5}$ alkoxycarbonyl, amino, C$_{1-5}$ acyl, C$_{1-5}$ acylamino, halogen, cyano, nitro, hydroxyl, C$_{1-5}$ alkyl—S(O)$_m$—NH—, C$_{1-5}$ alkyl—NH—S(O)$_m$— or carboxyl;
R$_b$ is hydroxyl, carboxyl, halogen, cyano, —CH$_2$—CN, C$_{1-5}$ alkyl, C$_{2-5}$ alkynyl, C$_{3-7}$ cycloalkyl, C$_{1-5}$ alkoxy, C$_{1-5}$ alkoxycarbonyl, —(CH$_2$)$_x$—NR$_c$R$_d$, R$_4$—S(O)$_m$—, R$_4$—S(O)$_m$—NR$_e$—, R$_4$—NR$_e$—S(O)$_m$—, —NR$_f$—C(O)—R$_e$, —(CH$_2$)$_x$—C(O)—(CH$_2$)$_n$—NR$_c$R$_d$, phenyl, pyrazolyl, pyrrolyl, imidazolyl, thiadiazolyl, pyridinyl, pyridinonyl, pyrimidinyl, pyridazinyl, pyrazinyl, pyrrolidinyl, piperidinyl or piperazinyl, each substituent on R$_b$ where possible is optionally halogenated or substituted with 1 to 3 C$_{1-6}$ alkyl, C$_{1-6}$ acyl, C$_{1-6}$ alkoxycarbonyl, C$_{1-6}$ alkyl—S(O)$_m$—, phenyl, naphthyl or carboxyl;
R$_4$ is hydrogen, C$_{1-5}$ alkyl, phenyl, naphthyl, oxazolyl, isoxazolyl, thiazolyl, pyrazolyl, pyrrolyl, imidazolyl, thienyl, thiadiazolyl, thiomorpholinyl, 1,1-dioxo-1λ$^6$-thiomorpholinyl, morpholinyl, pyridinyl, pyridinonyl, pyrimidinyl, pyridazinyl, pyrazinyl, triazinyl, pyrrolidinyl, piperidinyl, piperazinyl or tetrahydropyranyl, each optionally substituted with halogen, hydroxyl, C$_{1-5}$alkyl, C$_{1-5}$ alkoxy, amino, mono-or di-C$_{1-5}$ alkylamino, C$_{1-5}$ alkoxycarbonyl or C$_{1-5}$ acylamino;
R$_x$ is hydrogen.

3. The compound to claim 2 and wherein
Ar$_1$ is phenyl optionally substituted by one to three R$_a$;
Ar$_2$ is phenyl, naphthyl, benzimidazolyl, benzimidazolonyl, thiomorpholinyl, 1,1-dioxo-1λ$^6$-thiomorpholinyl, morpholinyl, pyridinyl, pyridinonyl, pyrimidinyl, pyridazinyl, pyrazinyl, piperidinyl, piperazinyl, indolyl, isoindolyl, benzofuranyl or benzopyranyl each optionally substituted by one to three R$_b$;
R$_1$ is hydrogen or C$_{1-3}$ alkyl;
R$_2$, R$_3$ are each independently hydrogen or C$_{1-3}$ alkyl;

$R_a$ is $C_{1-5}$ alkyl, $C_{3-6}$ cycloalkyl, $C_{1-5}$ alkoxy, $C_{1-5}$ alkoxycarbonyl, halogen, cyano, hydroxyl, $C_{1-5}$ alkyl—S(O)$_m$—NH—, $C_{1-5}$ alkyl—NH—S(O)$_m$— or carboxyl;

$R_b$ is hydroxyl, carboxyl, halogen, cyano, —CH$_2$—CN, $C_{1-5}$ alkyl, $C_{2-4}$ alkynyl, $C_{3-7}$ cycloalkyl, $C_{1-5}$ alkoxy, $C_{1-5}$ alkoxycarbonyl, —(CH$_2$)$_n$—NR$_c$R$_d$, R$_4$—S(O)$_m$—, R$_4$—S(O)$_m$—NR$_e$—, R$_4$—NR$_e$—S(O)$_m$—, —NR$_f$—C(O)—R$_e$, —(CH$_2$)$_x$—C(O)—(CH$_2$)$_n$—NR$_c$R$_d$, phenyl, pyrazolyl, pyrrolyl, imidazolyl, thiadiazolyl, pyridinyl, pyridinonyl, pyrimidinyl, pyridazinyl, pyrazinyl, pyrrolidinyl, piperidinyl or piperazinyl, each substituent on R$_b$ where possible is optionally halogenated or substituted with 1 to 3 $C_{1-6}$ alkyl, $C_{1-6}$ acyl, $C_{1-6}$ alkoxycarbonyl, $C_{1-6}$ alkyl—S(O)$_m$—, phenyl, naphthyl or carboxyl;

each $R_c$, $R_d$ are independently hydrogen, $C_{1-6}$ alkyl, $C_{1-6}$ acyl, $C_{3-10}$ cycloalkyl, $C_{1-6}$ alkoxy, hydroxyC$_{1-6}$ alkyl, $C_{1-6}$ alkylC$_{1-6}$ alkoxy, $C_{1-6}$ alkylsulfonyl, $C_{1-6}$ alkoxycarbonyl or —(CH$_2$)$_n$—NR$_e$R$_f$;

each $R_e$, $R_f$ are independently hydrogen, $C_{1-6}$ alkyl, $C_{3-10}$ cycloalkyl, $C_{1-6}$ alkoxy, hydroxyC$_{1-6}$ alkyl or $C_{1-6}$ acyl;

$R_4$ is hydrogen, $C_{1-5}$ alkyl, phenyl, naphthyl, oxazolyl, isoxazolyl, thiazolyl, pyrazolyl, pyrrolyl, imidazolyl, thienyl, thiadiazolyl, thiomorpholinyl, 1,1-dioxo-1λ$^6$-thiomorpholinyl, morpholinyl, pyridinyl, pyridinonyl, pyrimidinyl, pyridazinyl, pyrazinyl, triazinyl, pyrrolidinyl, piperidinyl or piperazinyl, each optionally substituted with halogen, hydroxyl, $C_{1-5}$ alkoxy, amino, mono-or di-$C_{1-5}$ alkylamino, $C_{1-5}$ alkoxycarbonyl or $C_{1-5}$ acylamino;

$R_5$ is hydrogen, CN, methyl, —S(O)$_2$—CH$_3$.

4. The compound to claim 3 and wherein Ar$_1$ is phenyl optionally substituted by one to three R$_a$;

$X_1$ is a —(CH$_2$)$_n$—;

$X_2$ is Ar$_2$;

Ar$_2$ is phenyl, naphthyl, benzimidazolyl, benzimidazolonyl, morpholinyl, pyridinyl or pyridinonyl, each optionally substituted by one to two R$_b$;

$R_1$ is hydrogen or $C_{1-3}$ alkyl;

$R_2$, $R_3$ are each independently hydrogen or $C_{1-3}$ alkyl;

$R_a$ is $C_{1-5}$ alkyl, $C_{3-6}$ cycloalkyl, $C_{1-5}$ alkoxy, $C_{1-5}$ alkoxycarbonyl, halogen, cyano, hydroxyl, $C_{1-5}$ alkyl—S(O)$_m$—NH—, $C_{1-5}$ alkyl—NH—S(O)$_m$— or carboxyl;

$R_b$ is carboxyl, halogen, cyano, —CH$_2$—CN, $C_{1-4}$ alkyl, CF$_3$, $C_{1-4}$ alkoxy, $C_{1-4}$ alkoxycarbonyl, ethynyl, phenyl, imidazolyl, piperidinyl, piperazinyl, or $R_b$ is NH$_2$—S(O)$_2$—,
NH$_2$—C(O)—CH$_2$—,
—N(C$_{1-3}$ alkyl)$_2$,
—N(C$_{1-3}$ alkyl)$_2$C(O)—C$_{1-3}$ alkyl,
—C(O)NH—C$_{1-3}$ alkyl,
—C(O)N(C$_{1-3}$ alkyl)$_2$,
—C(O)NH—(CH$_2$)$_{1-2}$—O—C$_{1-3}$alkyl,
—C(O)NH$_2$,
—S(O)$_2$—C$_{1-3}$ alkyl,
—S(O)$_2$—(CH$_2$)$_{1-2}$—C(O)—O—C$_{1-3}$alkyl,
—S(O)$_2$—NH—C$_{1-3}$ alkyl,
—S(O)$_2$—N(C$_{1-3}$ alkyl)$_2$,
—CH$_2$—S(O)$_2$—N(C$_{1-3}$ alkyl)$_2$,
—S(O)$_2$NH—(CH$_2$)$_{1-2}$—O—C$_{1-3}$alkyl,
—S(O)$_2$NH—(CH$_2$)$_{1-2}$—N(C$_{1-3}$alkyl)$_2$,
—S(O)$_2$NH—(CH$_2$)$_{1-2}$—OH,
—S(O)$_2$NH—(CH$_2$)$_{1-2}$—NHC(O)C$_{1-3}$alkyl),
—S(O)$_2$NH—(tetrahydropyran-4-yl),
—S(O)$_2$NR$_e$(1—C$_{1-3}$alkylpiperidin-4-yl),
—S(O)$_2$NH—(4—C$_{1-3}$ alkylpiperazin-1-yl),
—S(O)$_2$NH—(4-diC$_{1-3}$alkylaminopiperidin-4-yl),
—S(O)$_2$-morpholinyl,
—C(O)—O—C$_{1-3}$ alkyl,
—CH$_2$—C(O)—O—C$_{1-3}$ alkyl,
—SCF$_3$ or
—SCH$_3$.

5. The compound to claim 4 and wherein Ar$_1$ is

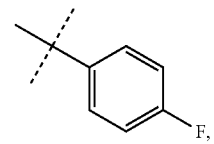

and the combination of

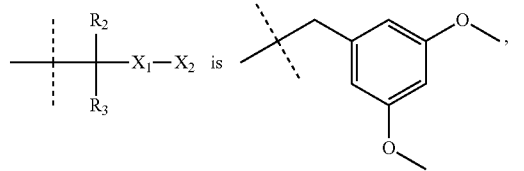 is

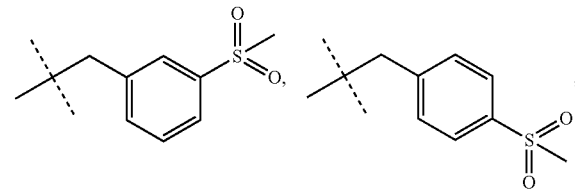

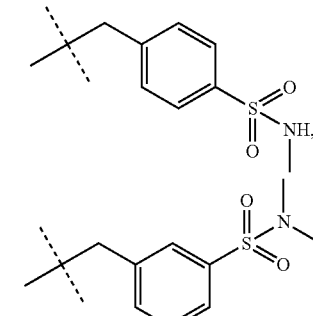

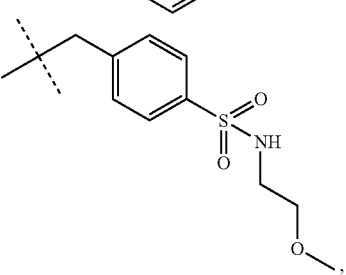

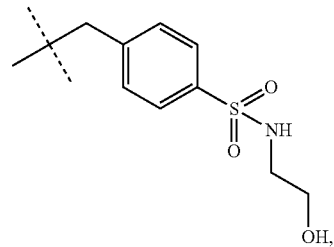

141
-continued
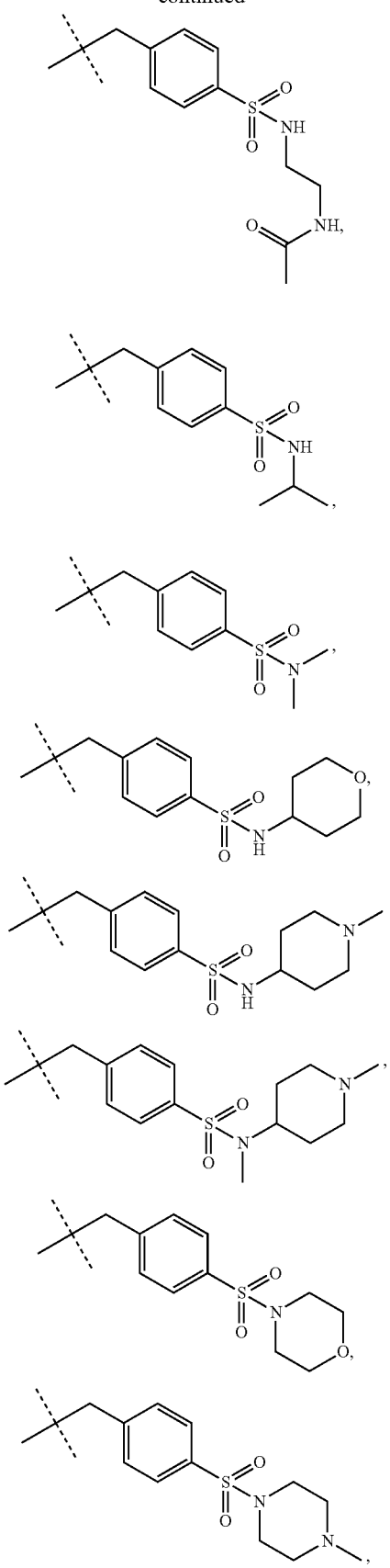
142
-continued
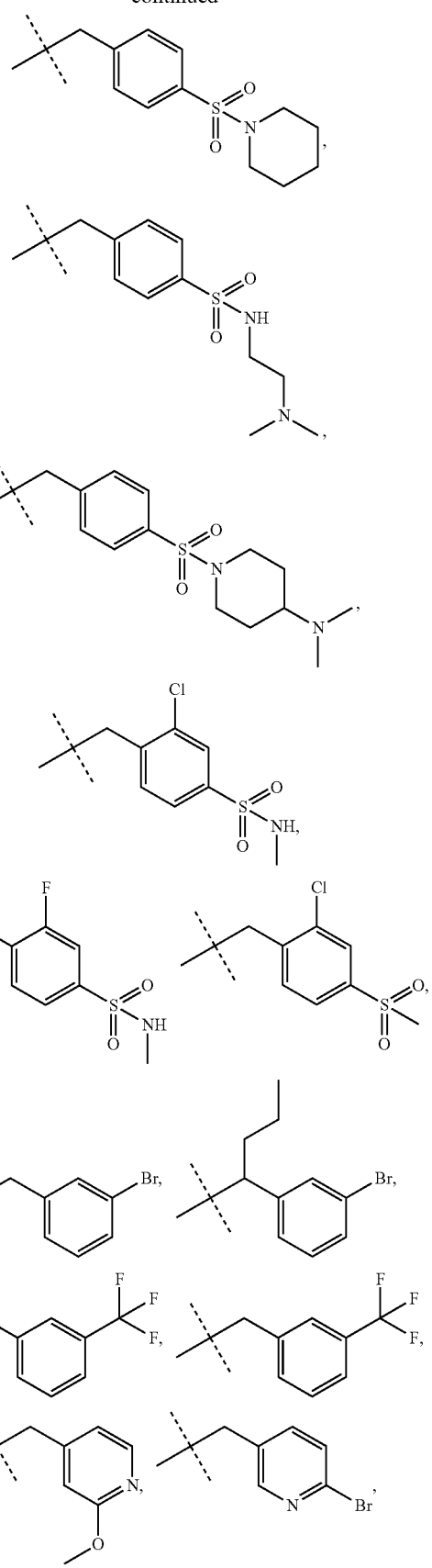

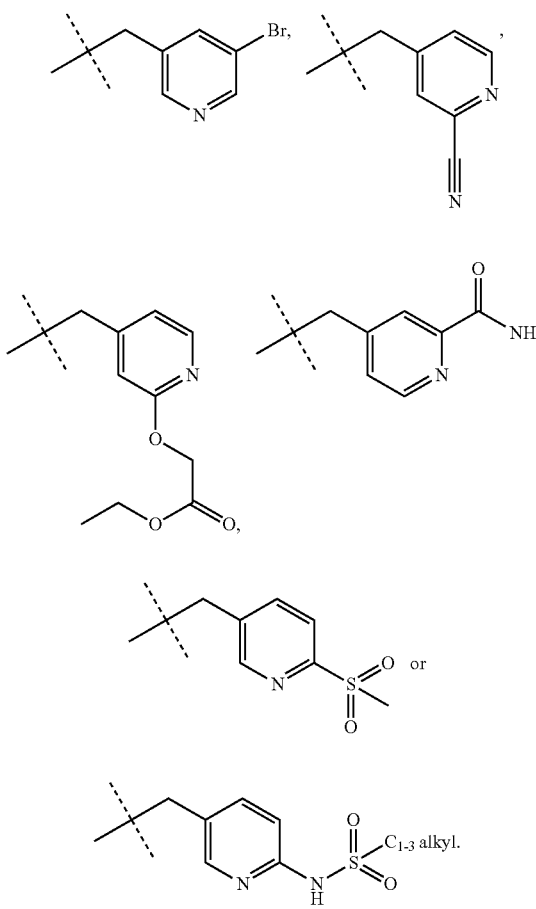
6. A compound chosen from
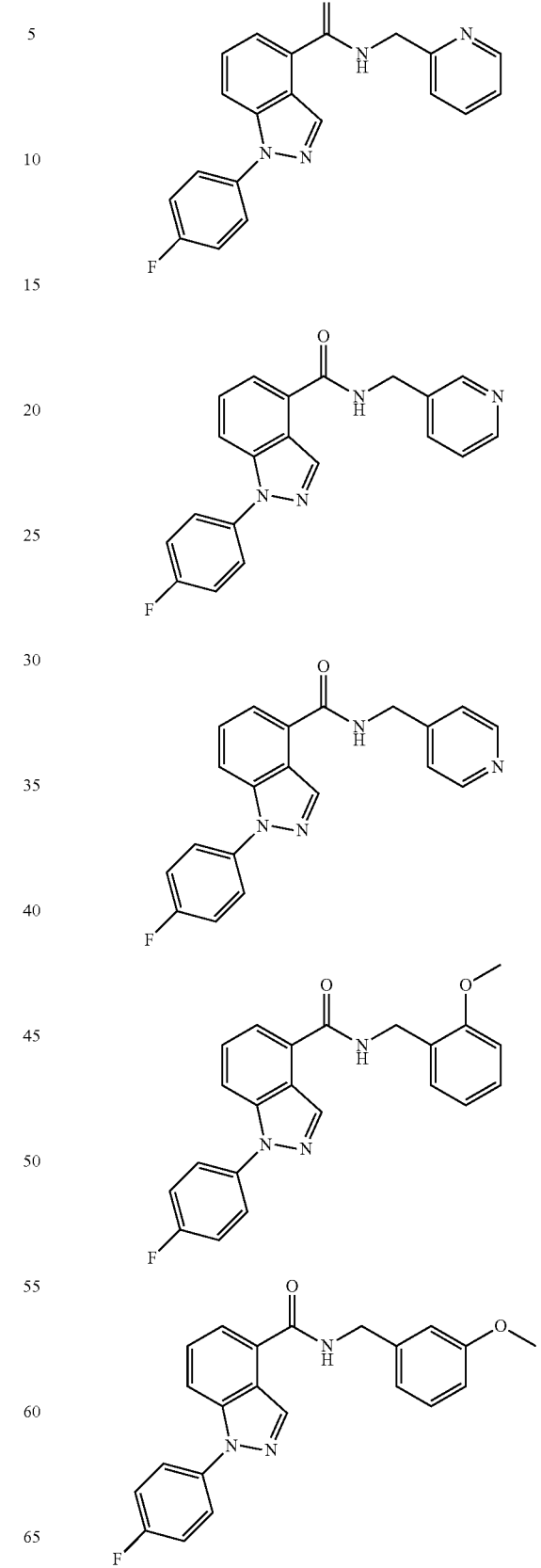

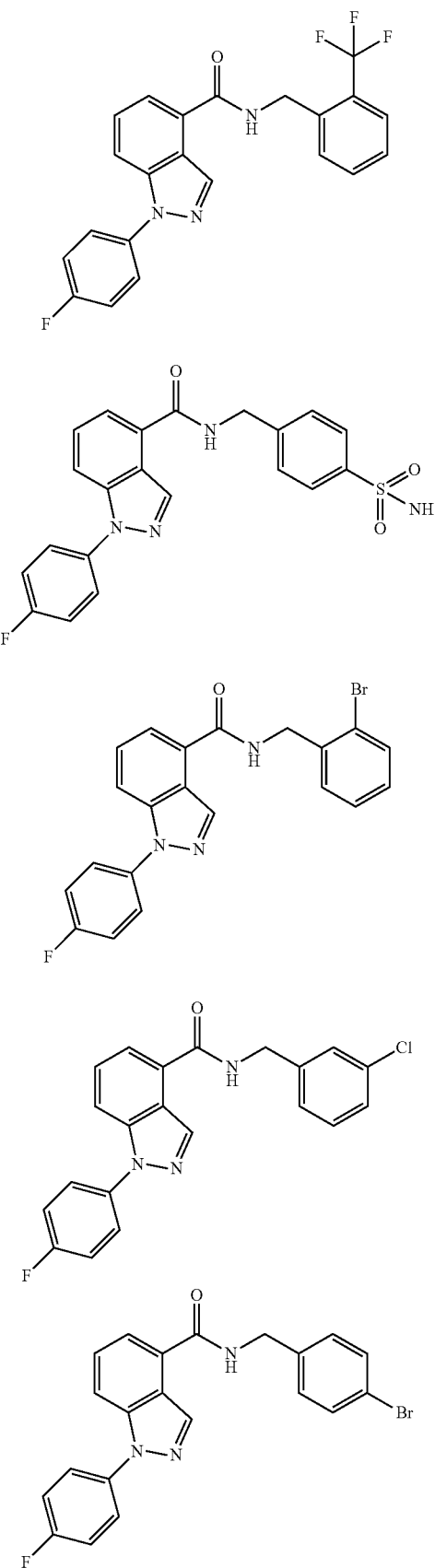
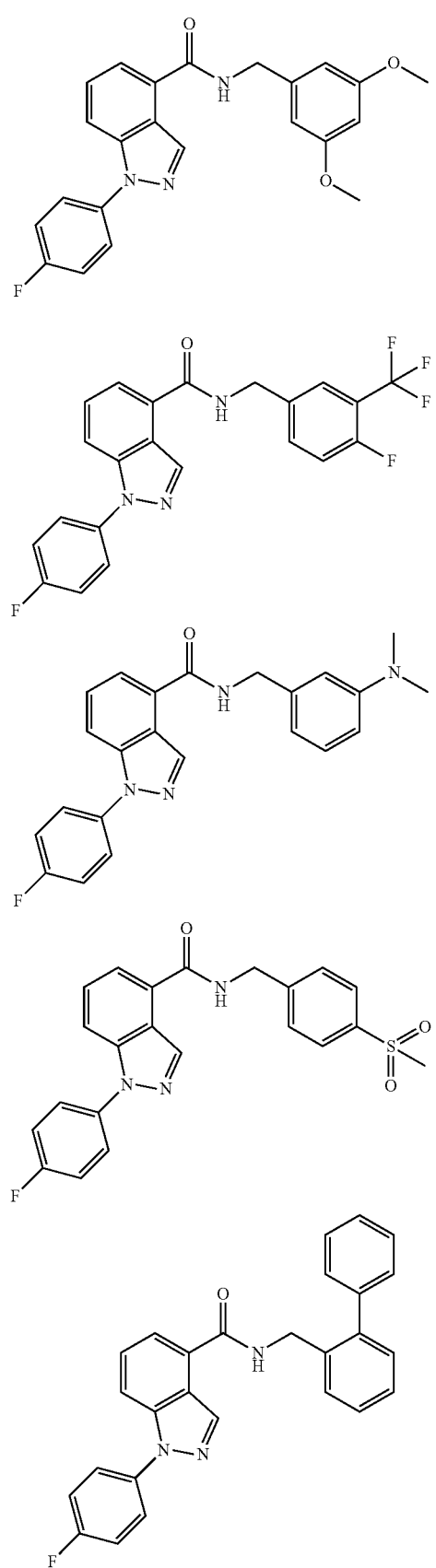

147
-continued
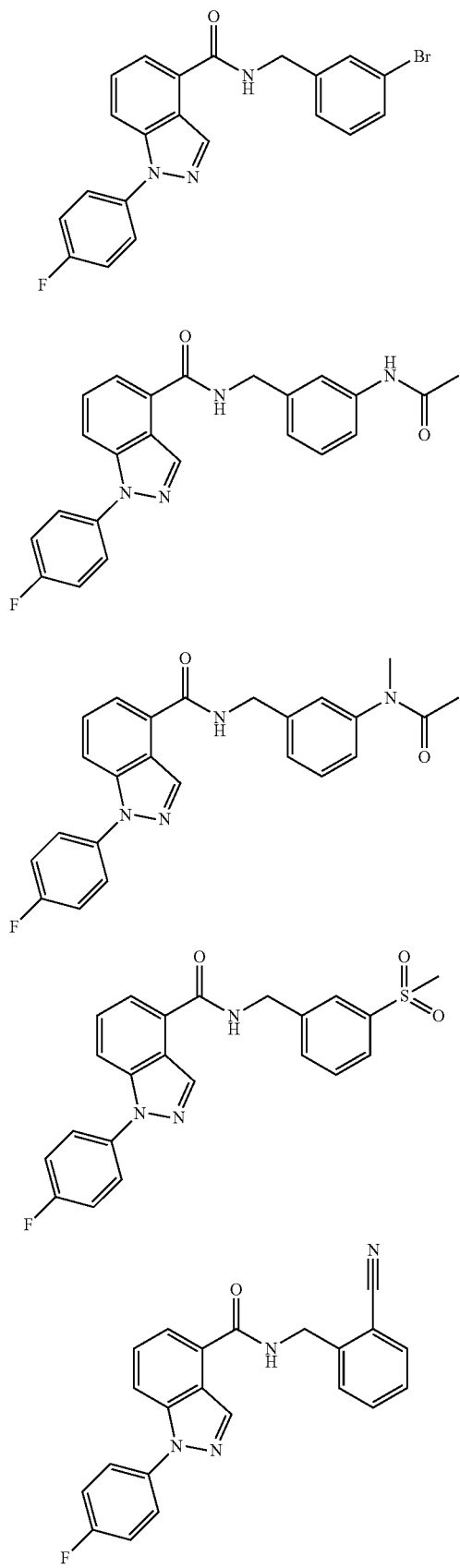
148
-continued
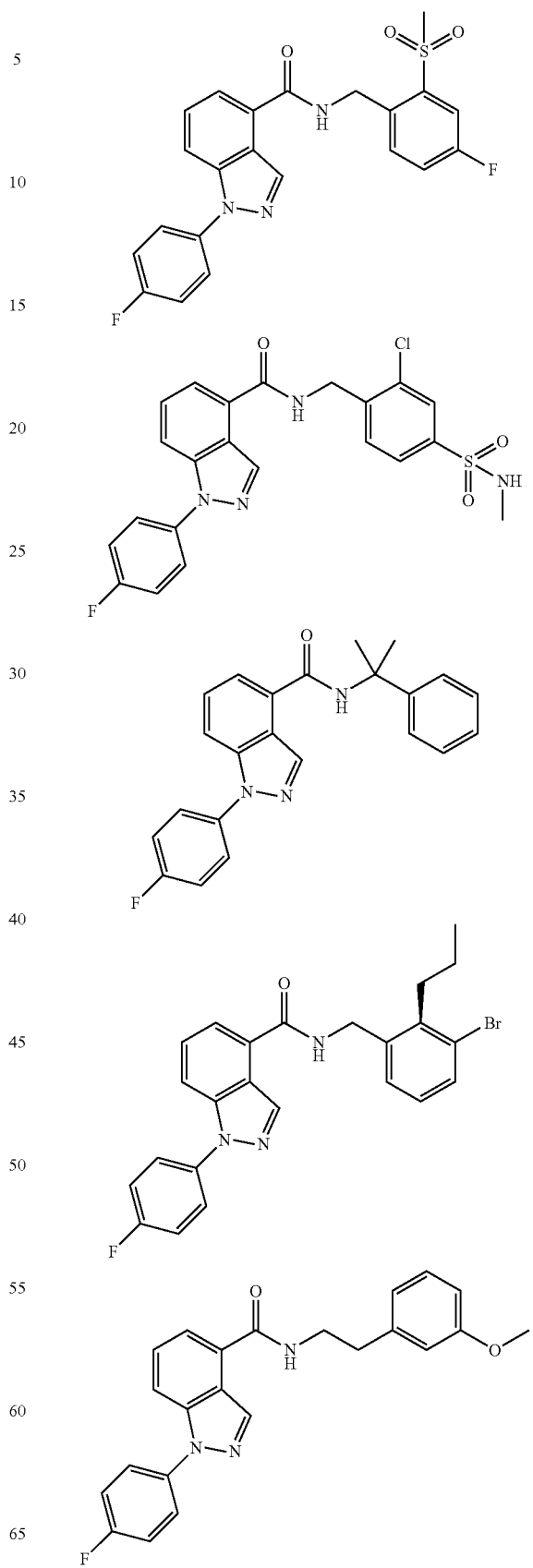

149
-continued
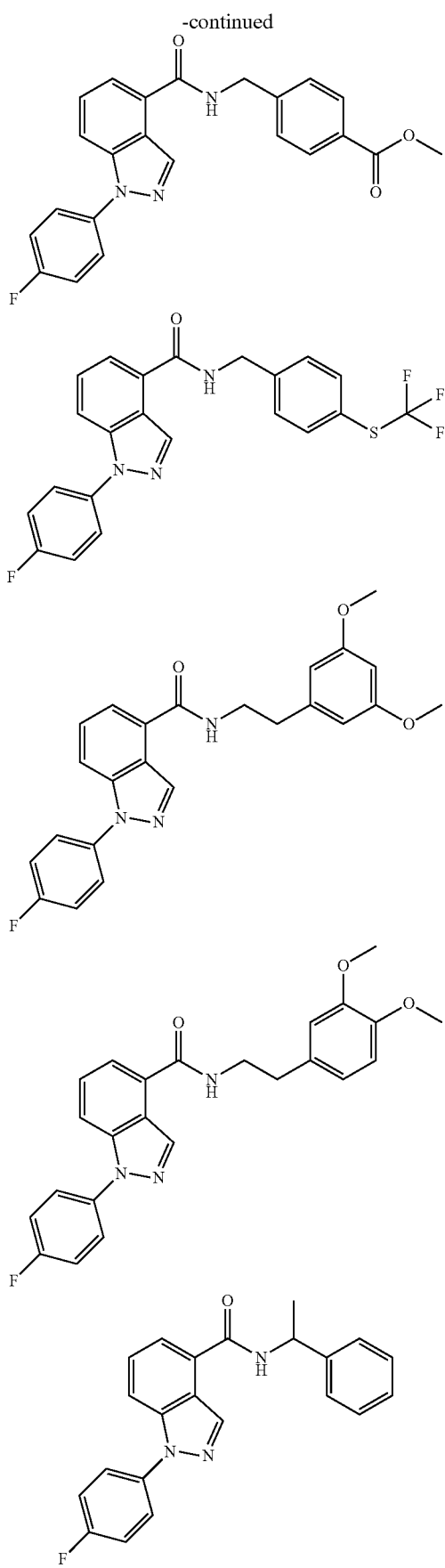
150
-continued
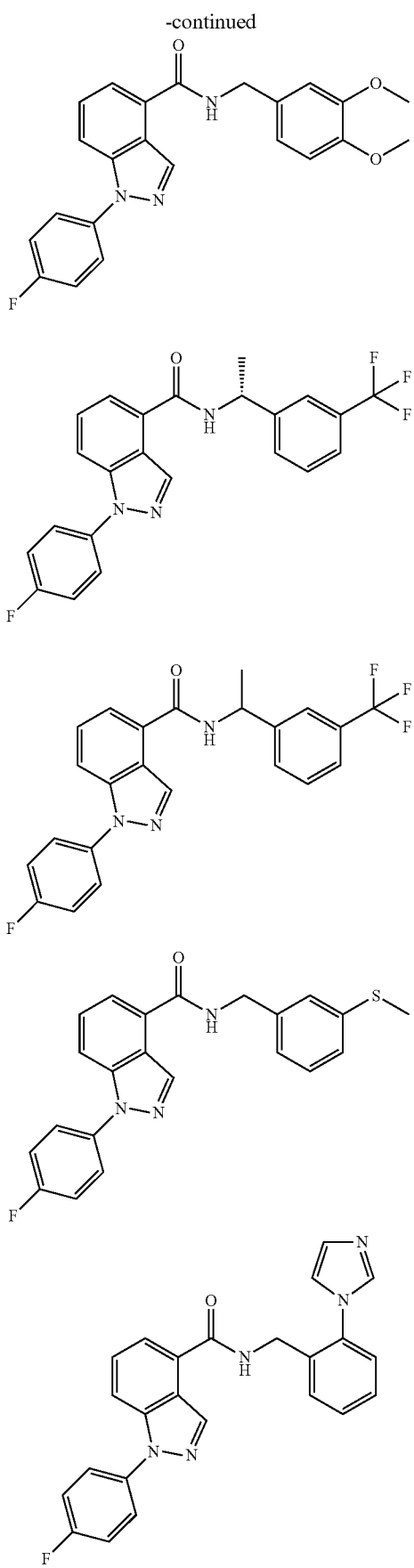

151
-continued
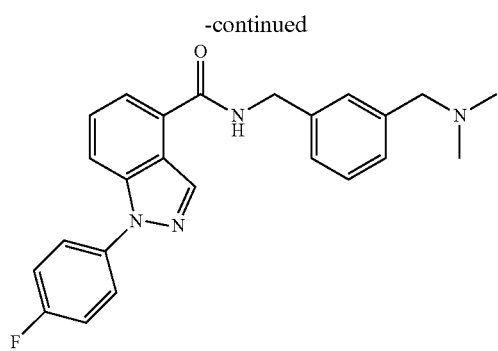
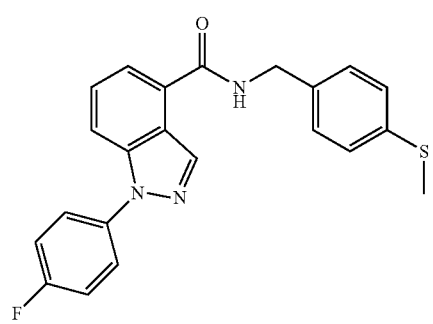
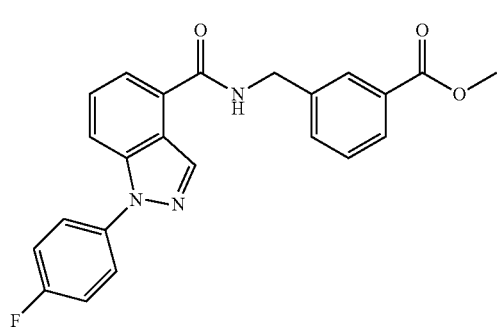
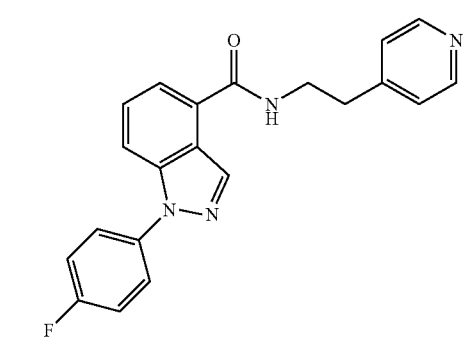
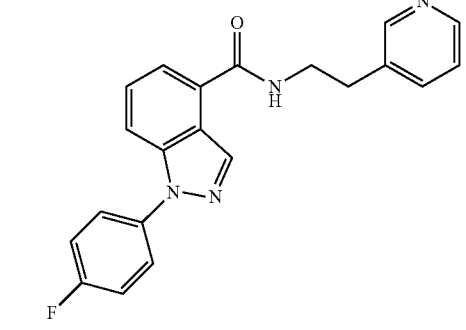
152
-continued
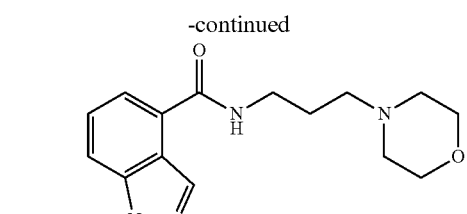
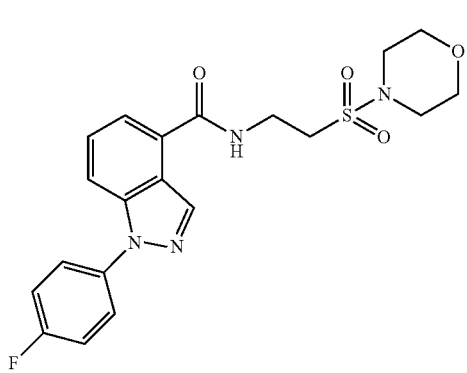
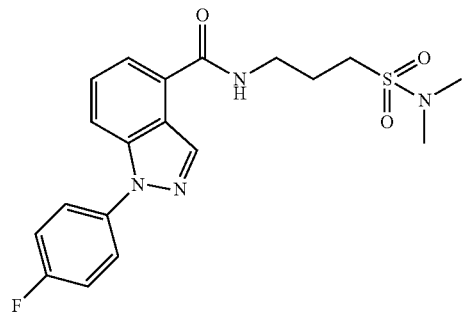
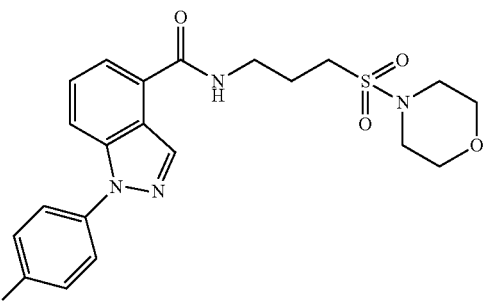
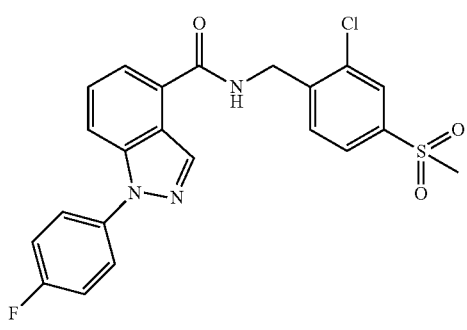

153
-continued
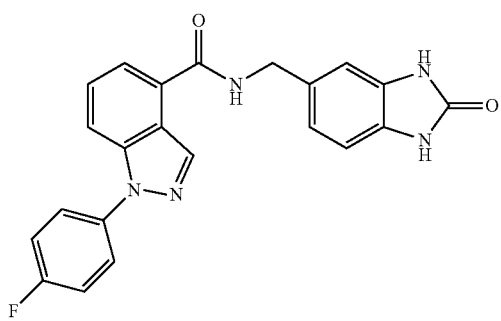
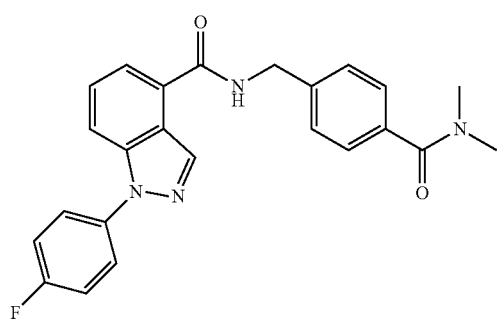
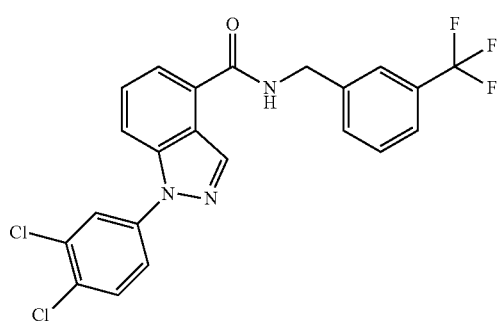
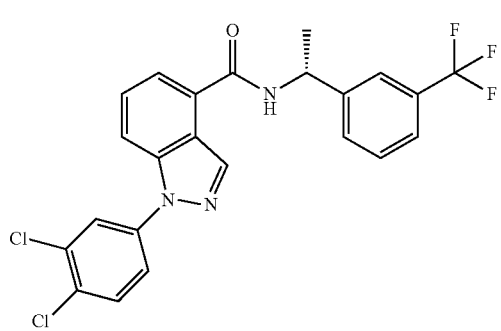
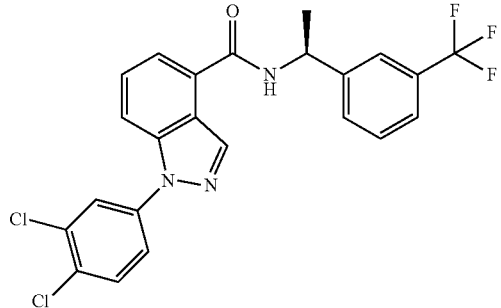
154
-continued
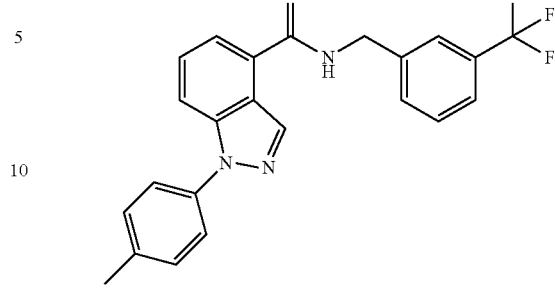
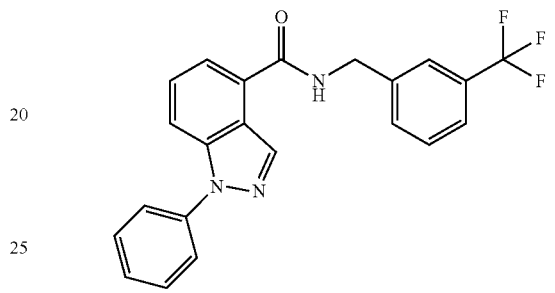
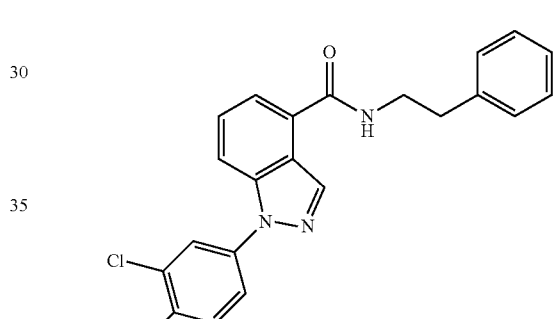
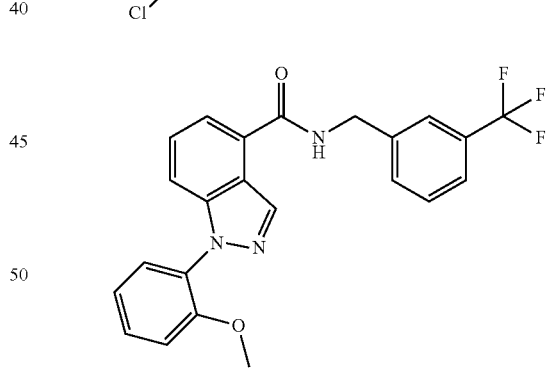
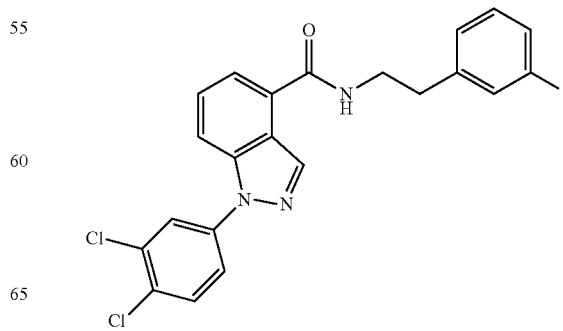

155
-continued
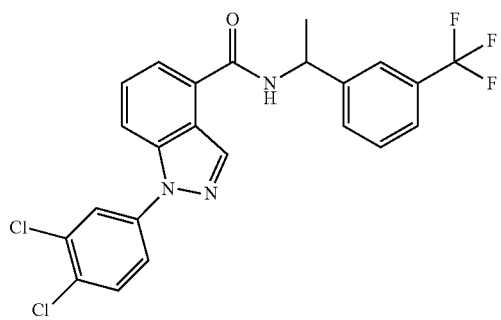
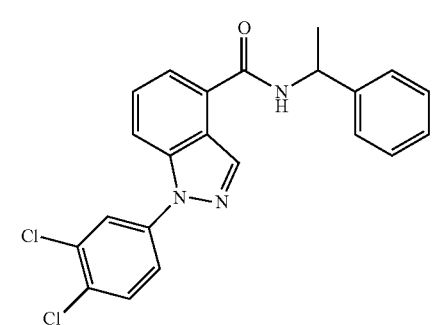
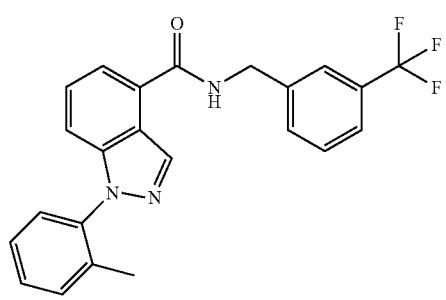
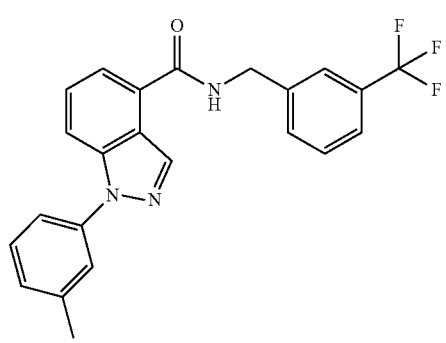
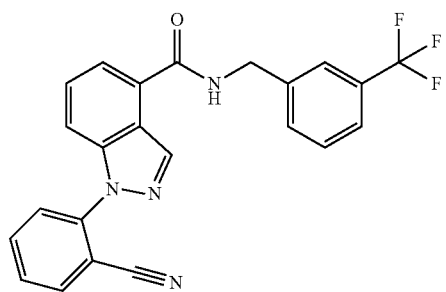
156
-continued
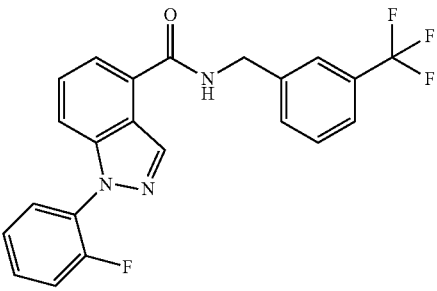
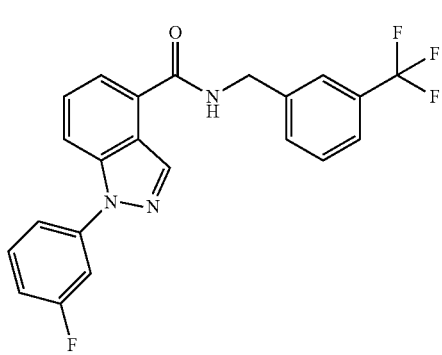
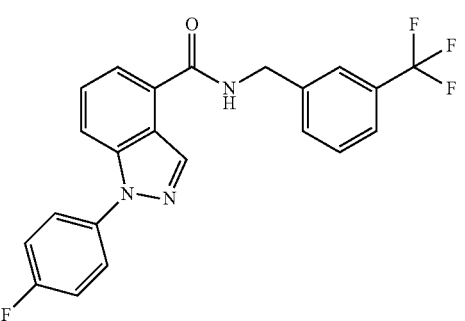
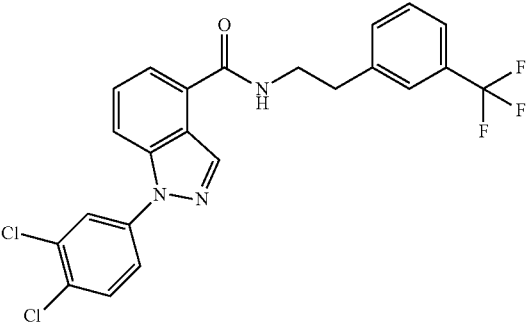
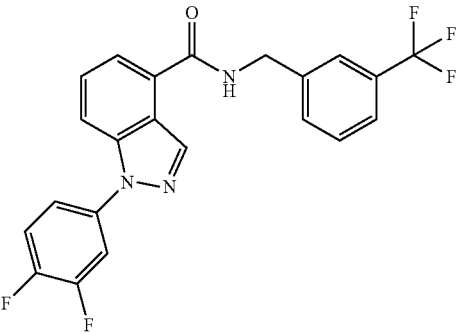

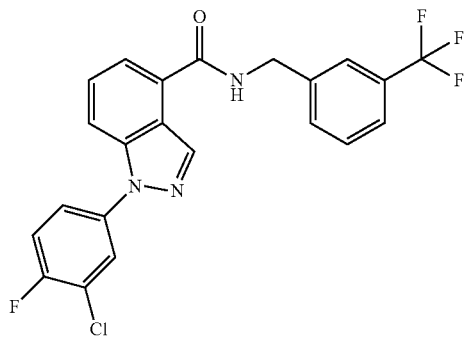
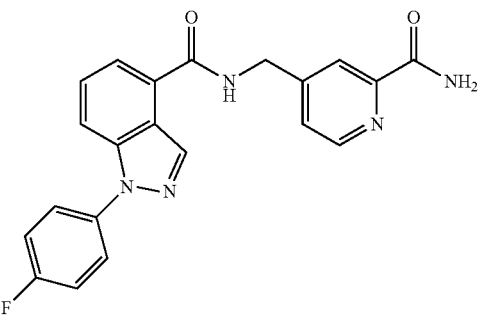
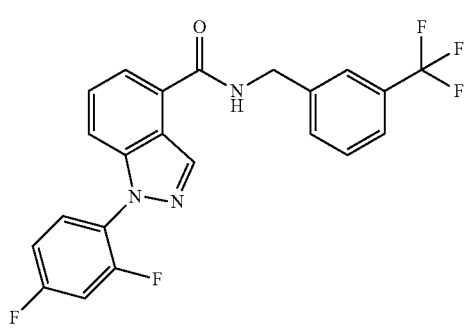
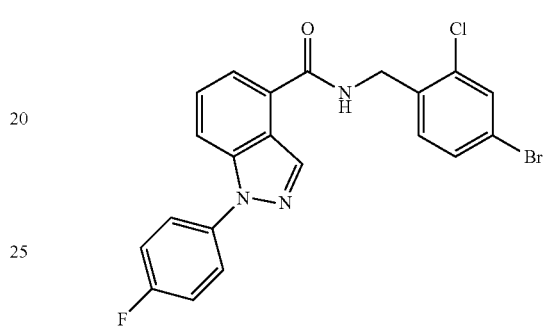
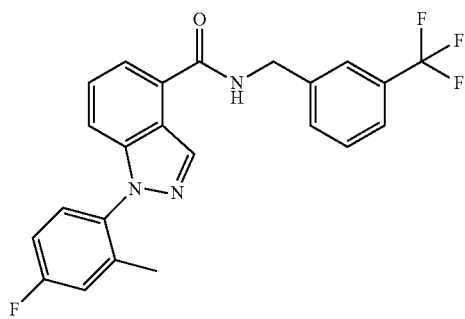
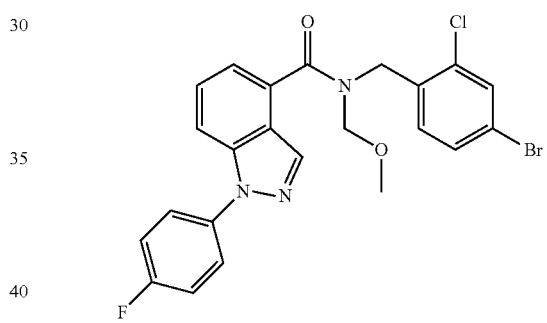
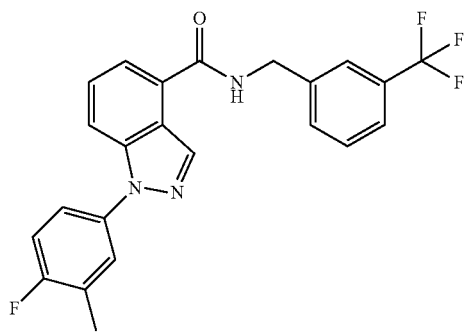
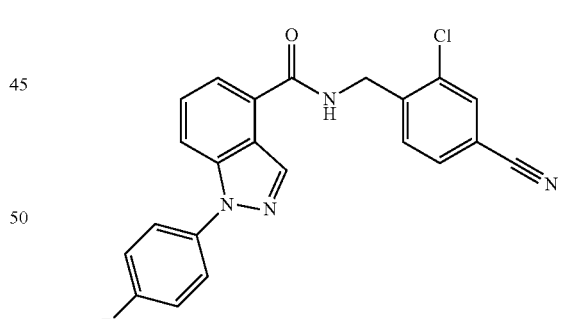
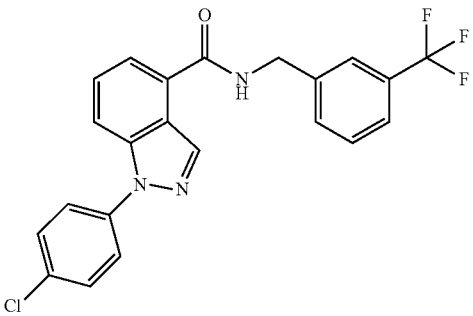
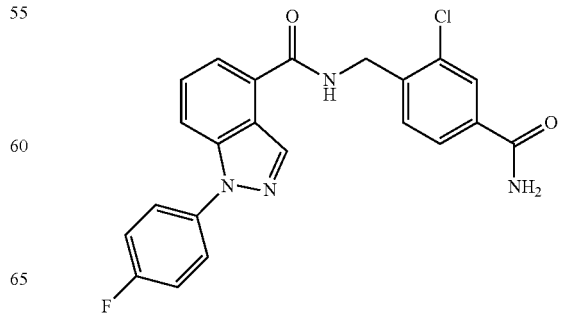

159
-continued
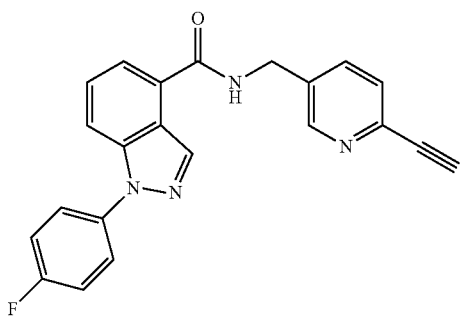
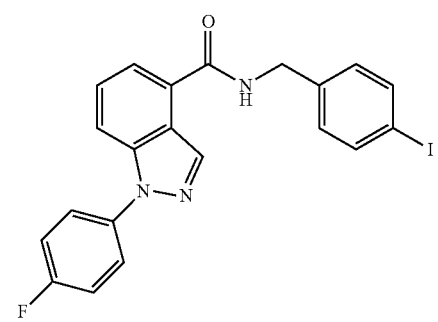
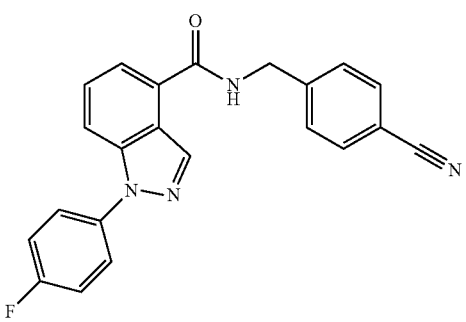
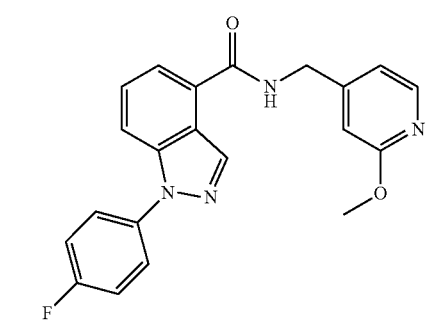
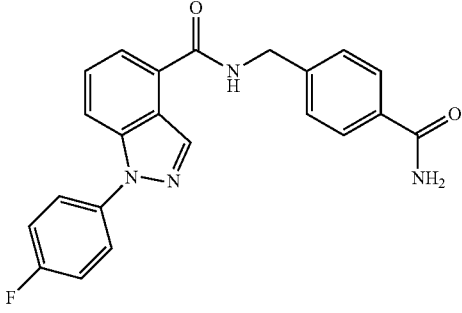
160
-continued
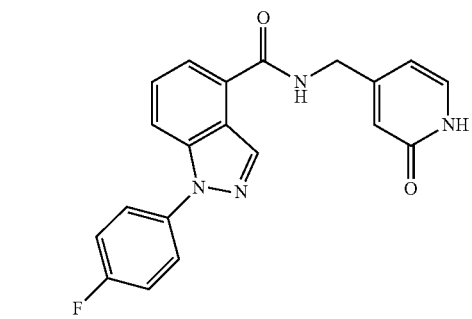
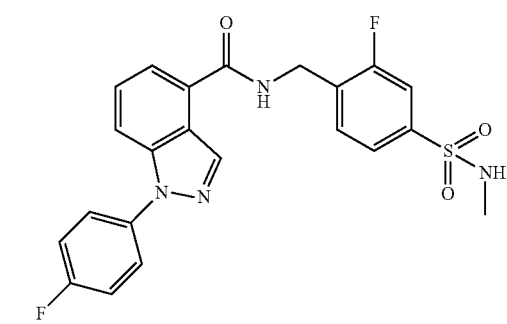
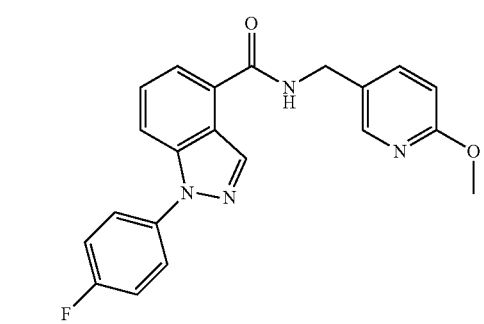
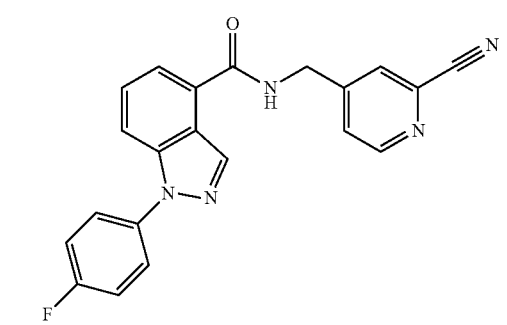
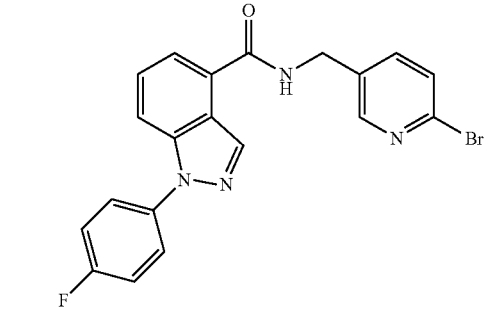

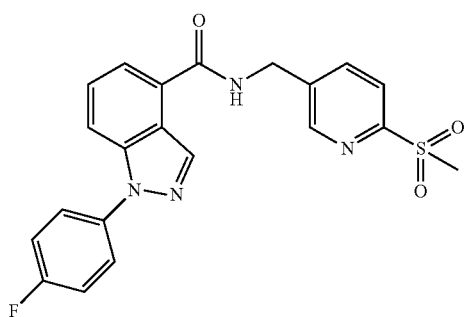
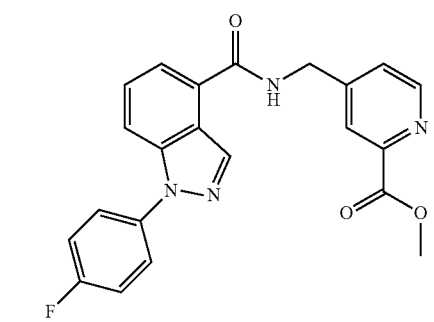
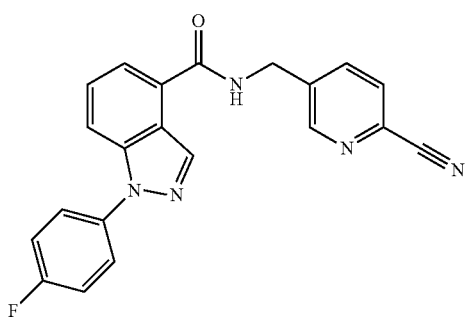
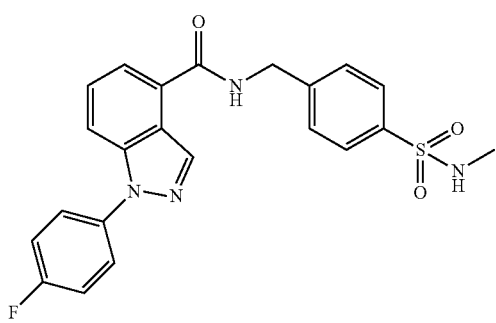
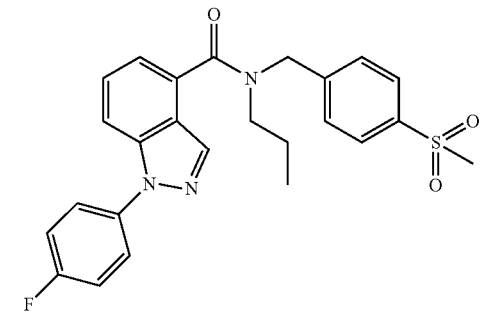
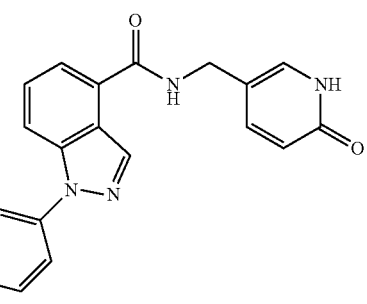
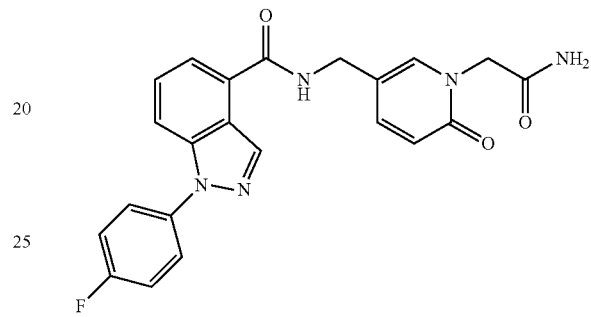
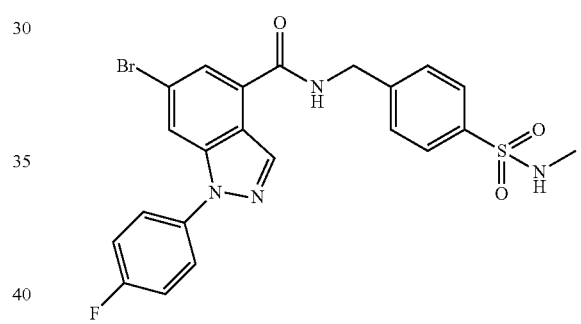
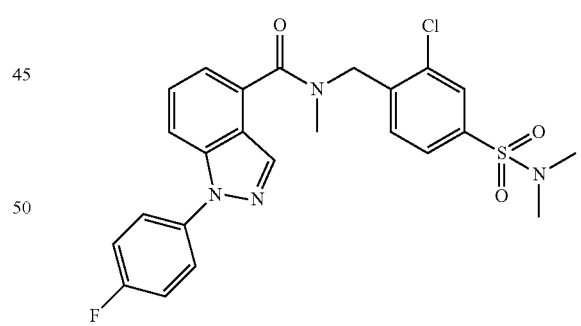
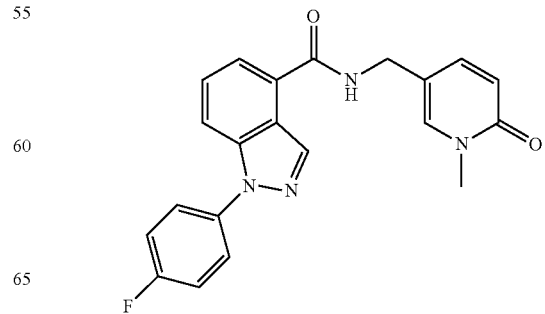

163
-continued
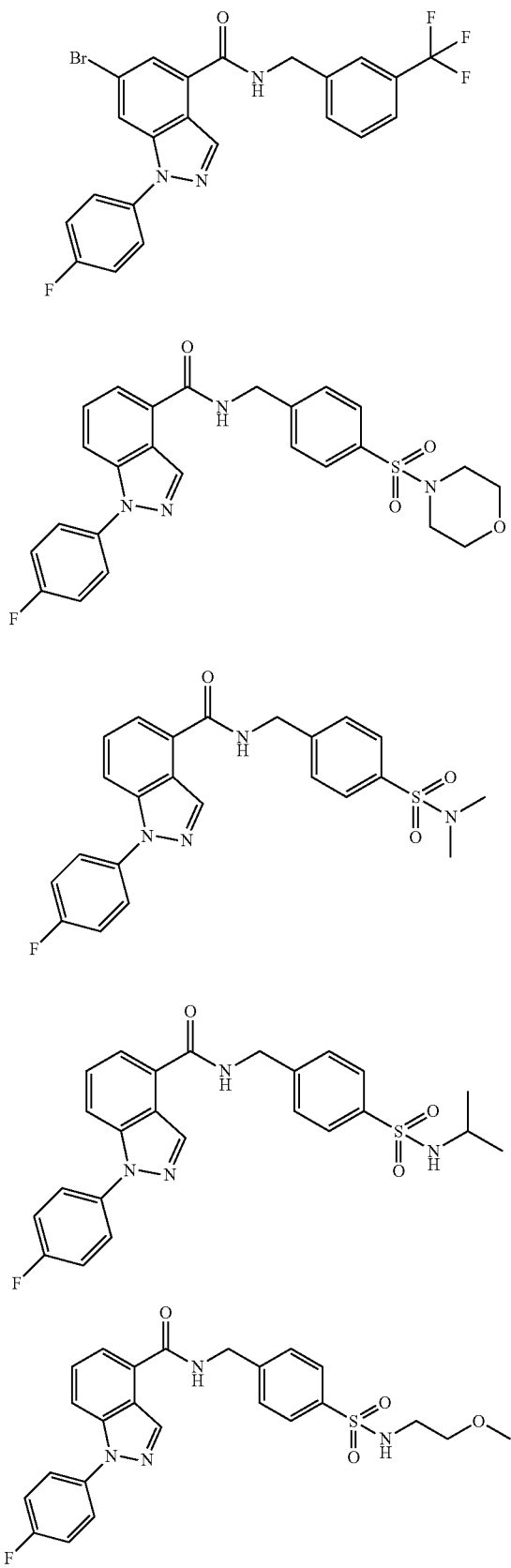
164
-continued
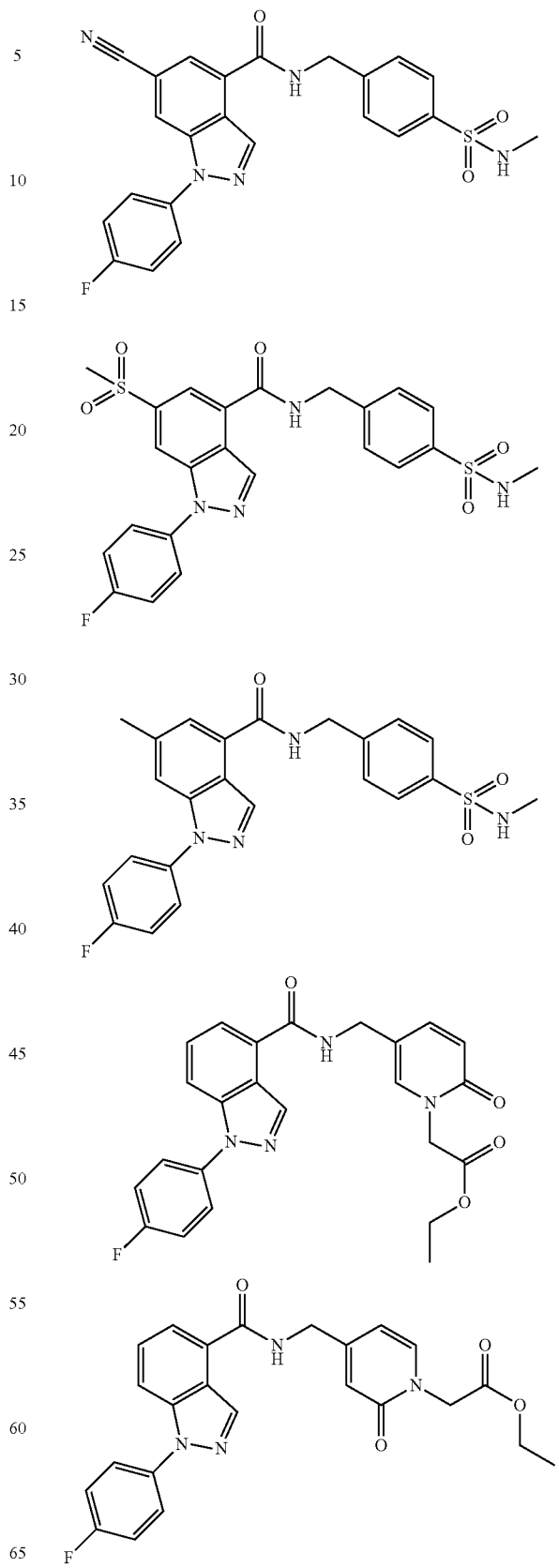

165
-continued
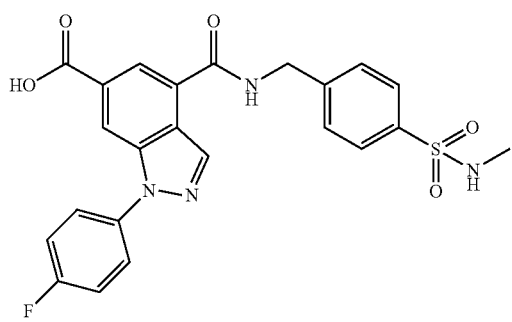
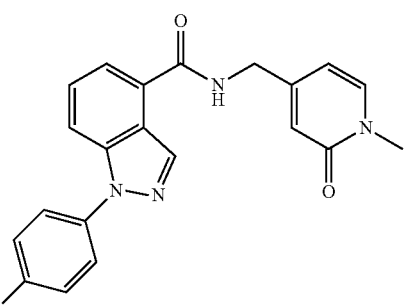
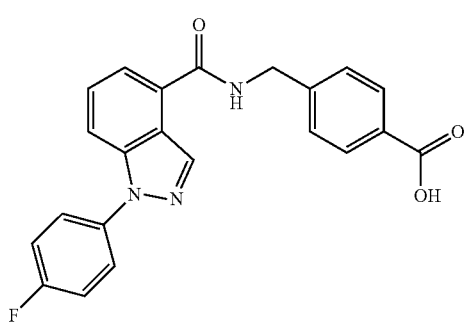
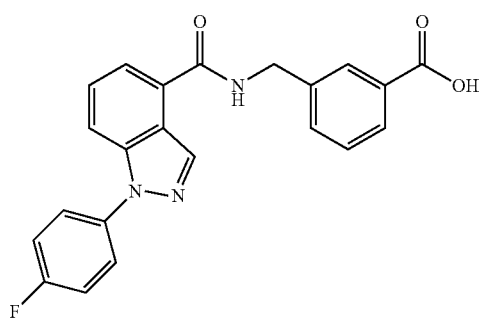
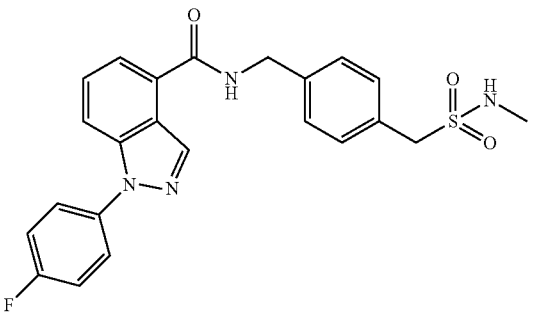
166
-continued
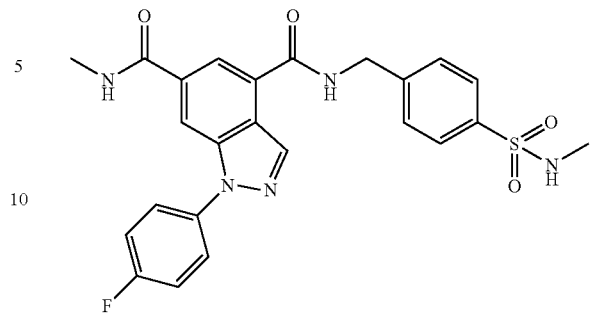
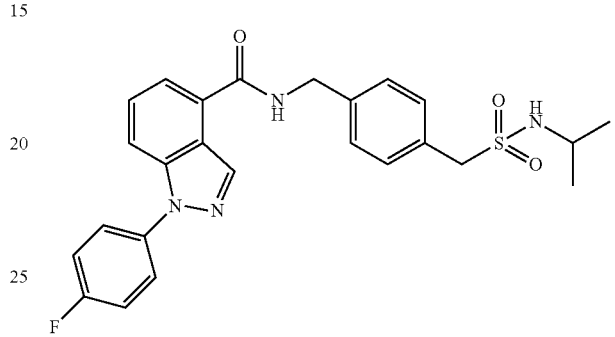
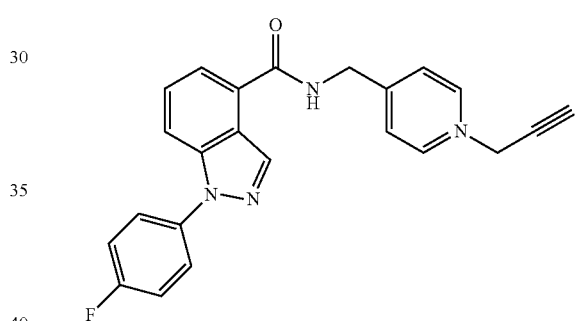
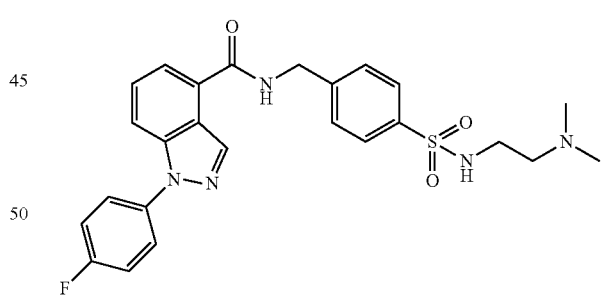
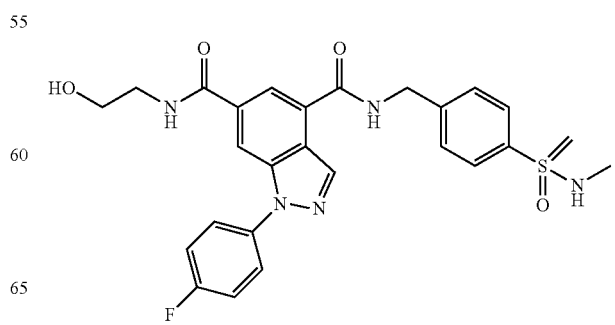

167
-continued
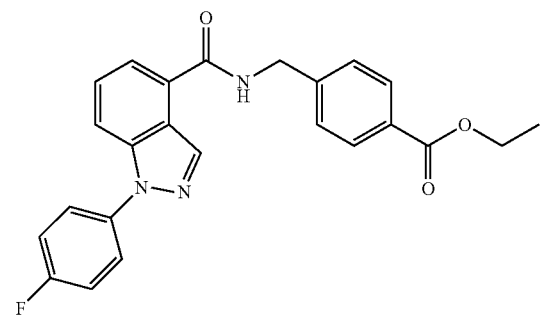
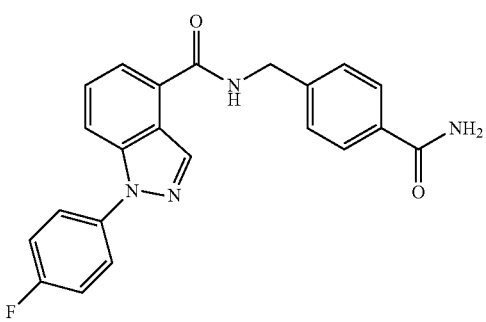
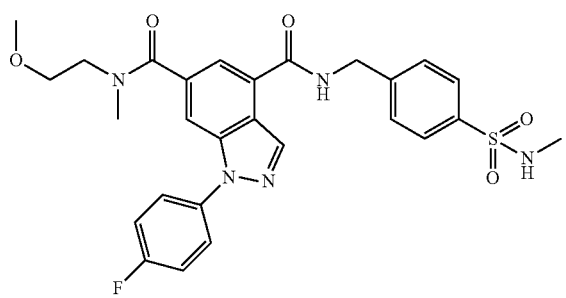
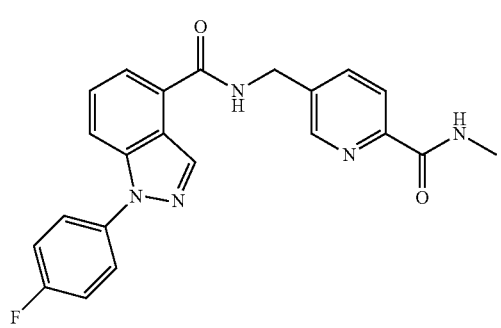
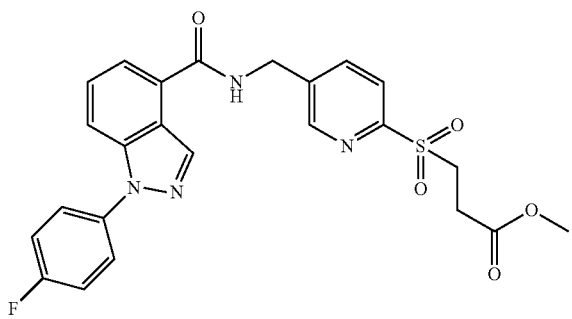
168
-continued
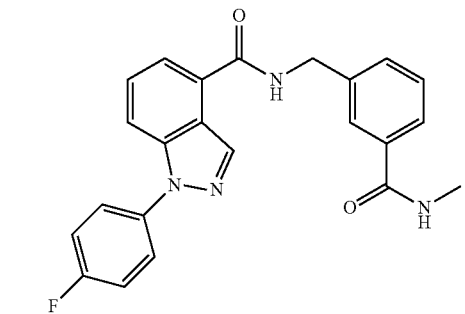
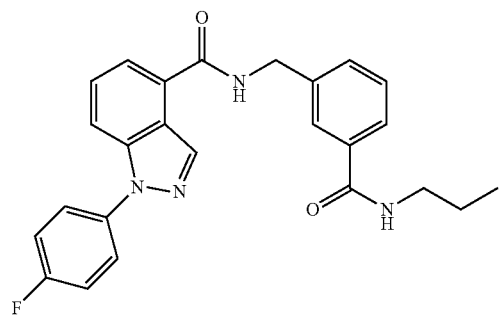
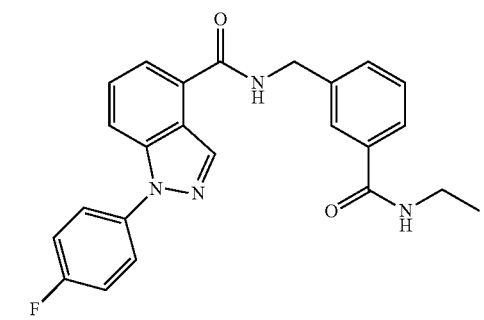
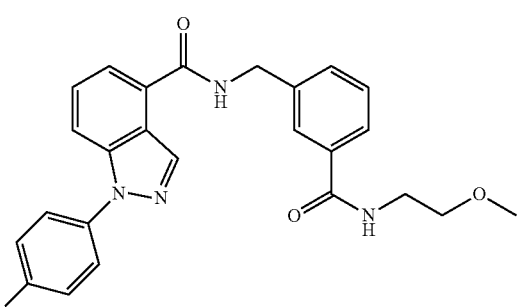
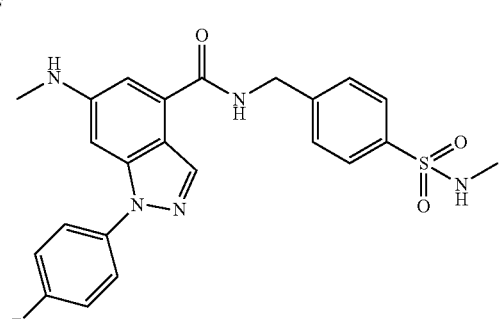

169
-continued
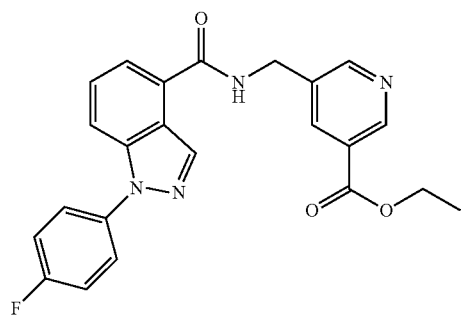
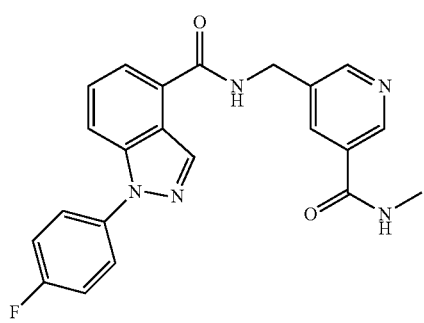
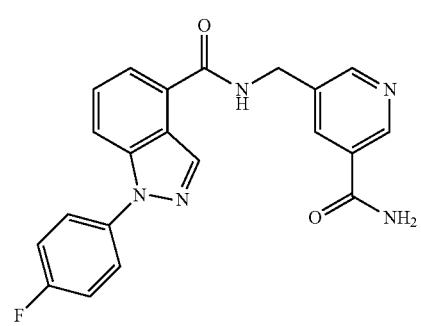
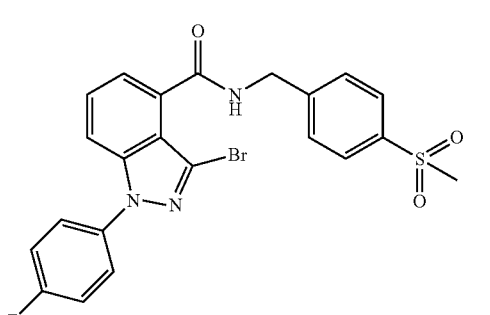
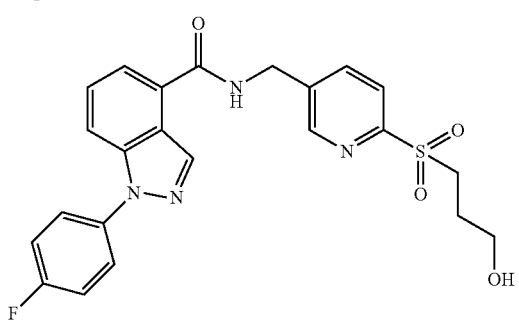
170
-continued
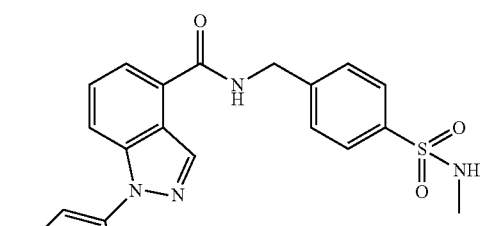
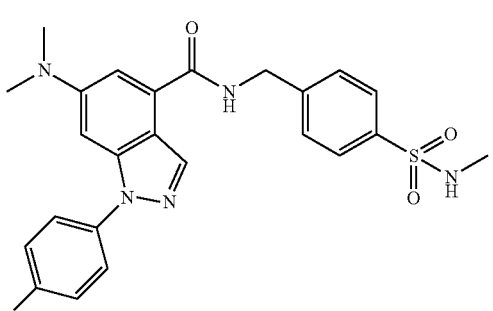
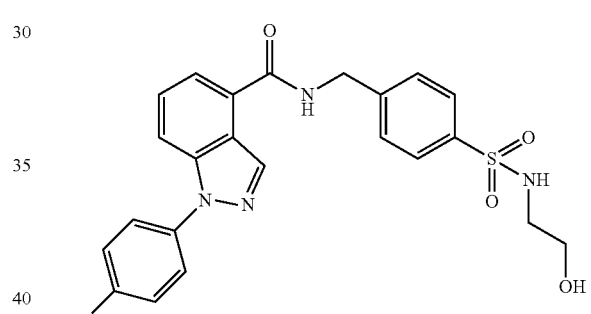
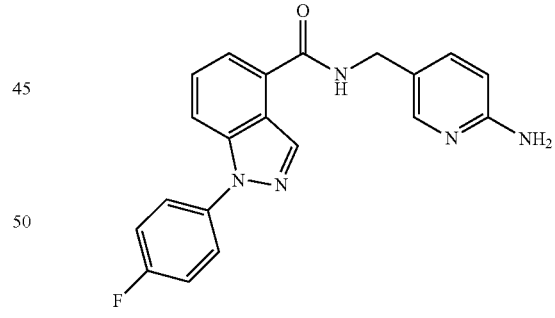
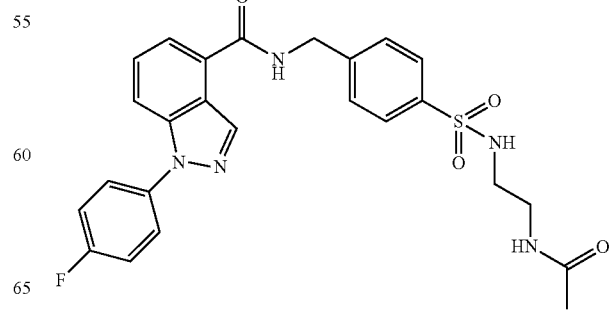

171
-continued
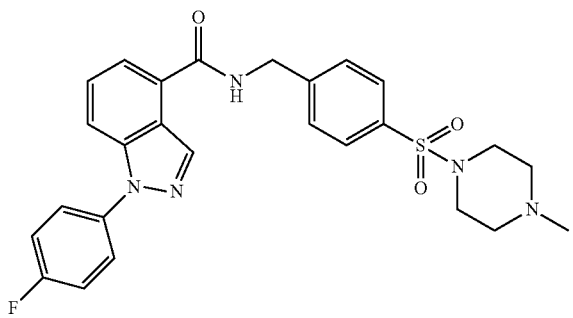
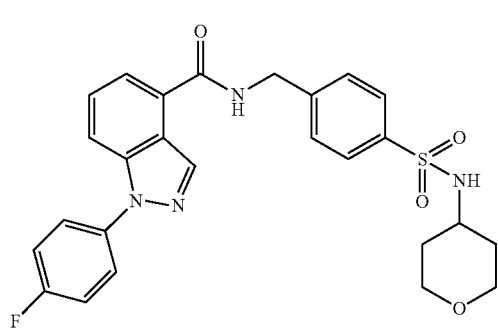
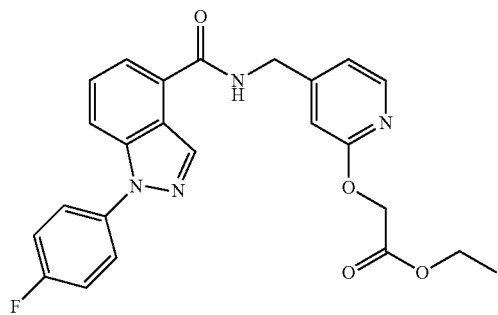
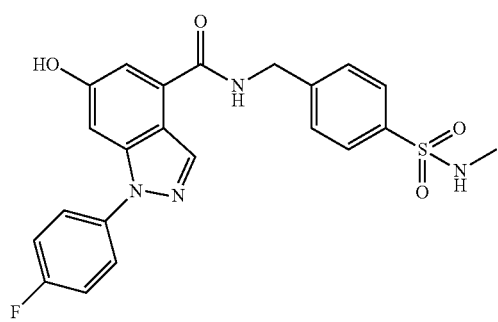
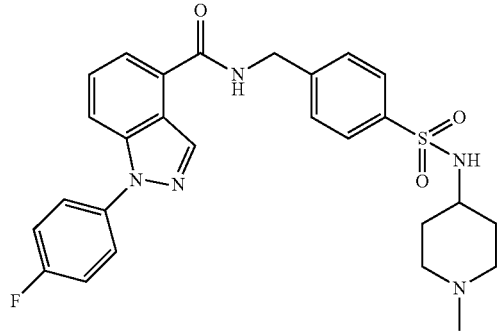
172
-continued
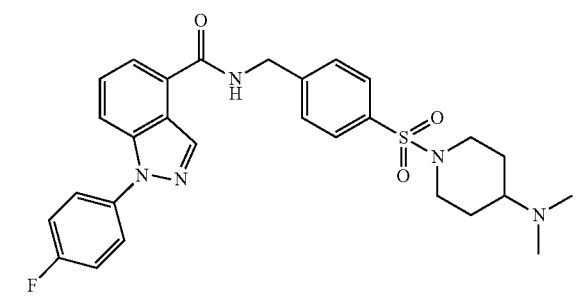
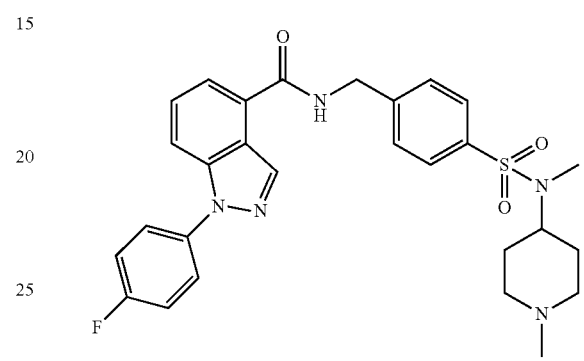
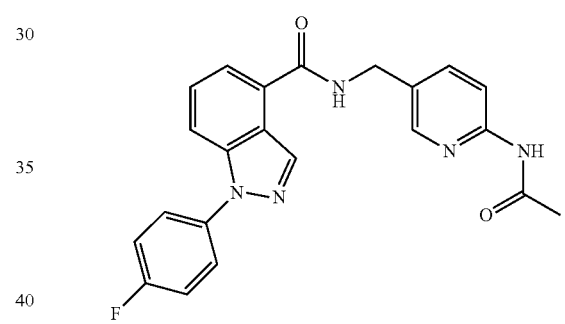
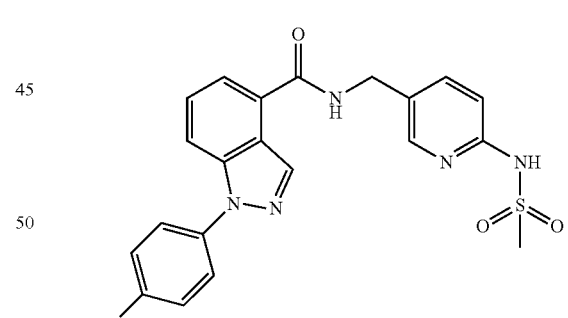
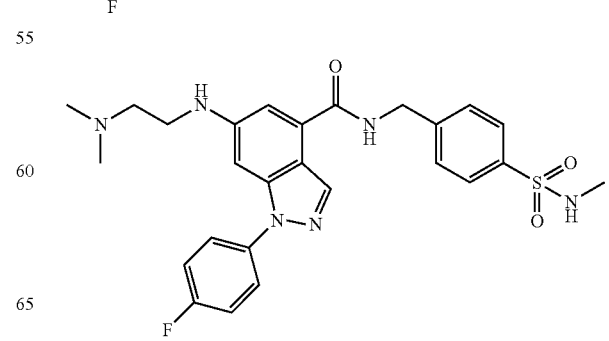

173
-continued
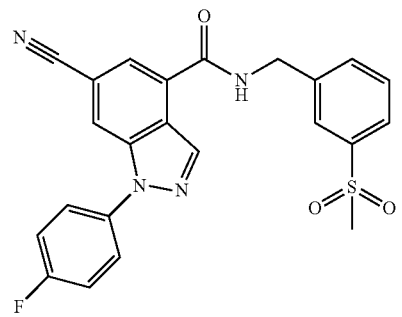
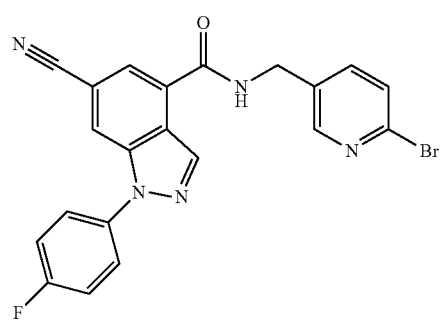
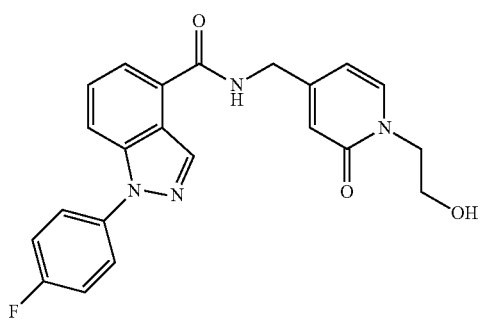
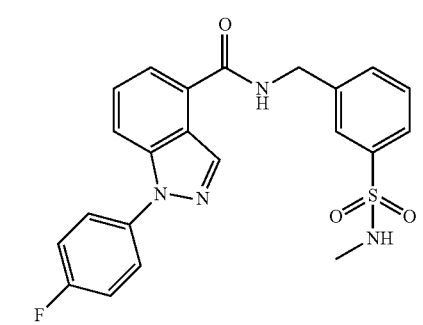
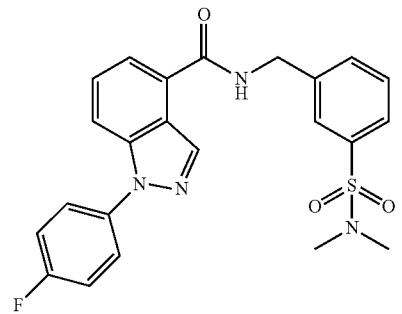
174
-continued
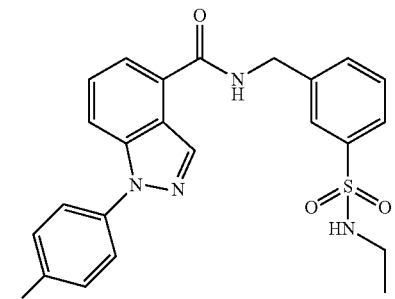
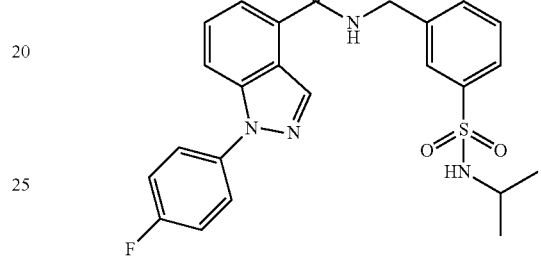
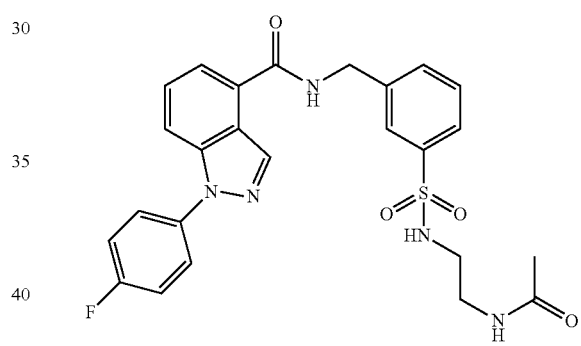
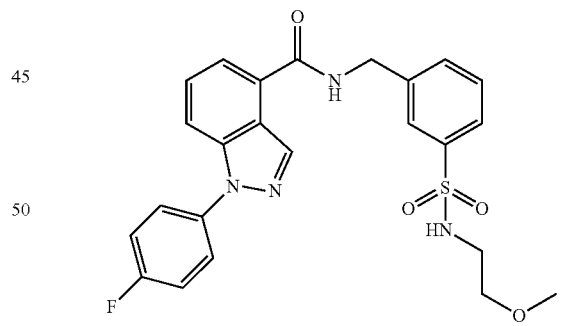
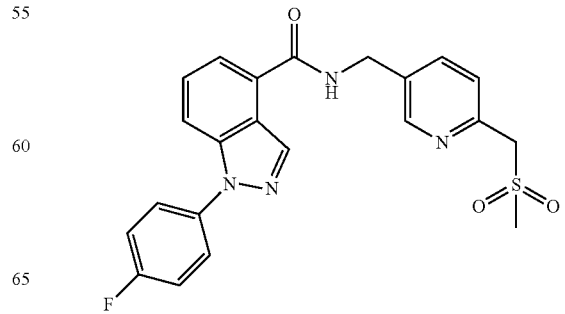

175
-continued
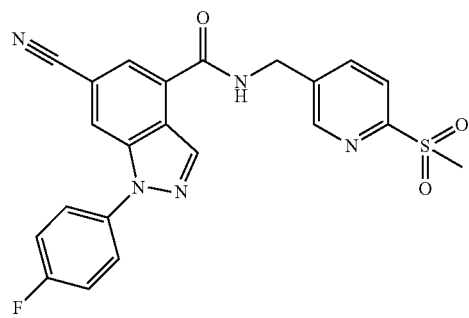
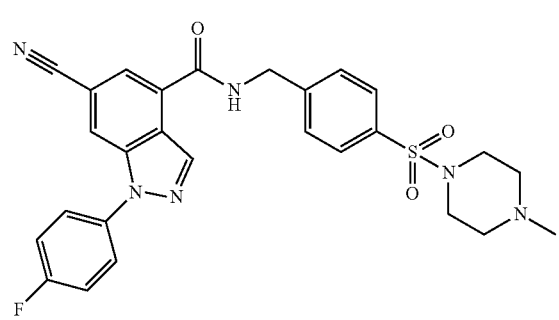
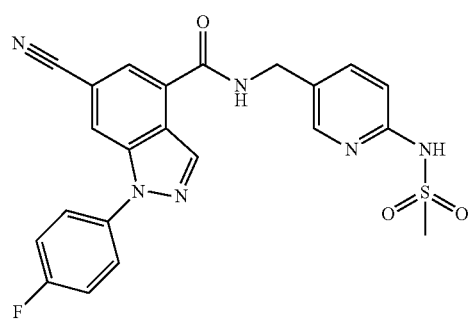
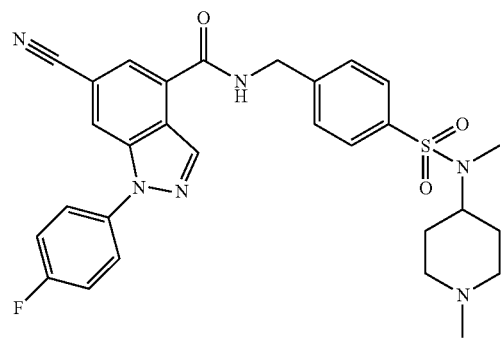
176
-continued
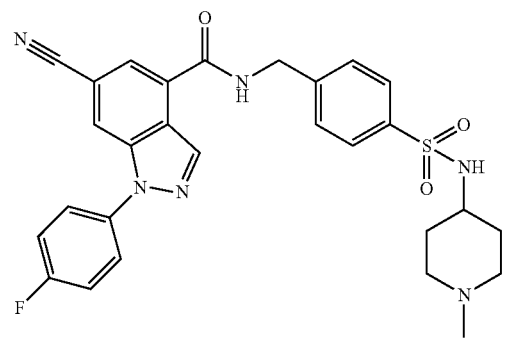
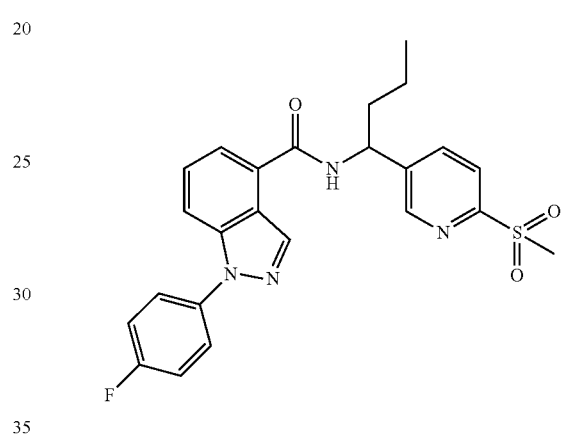
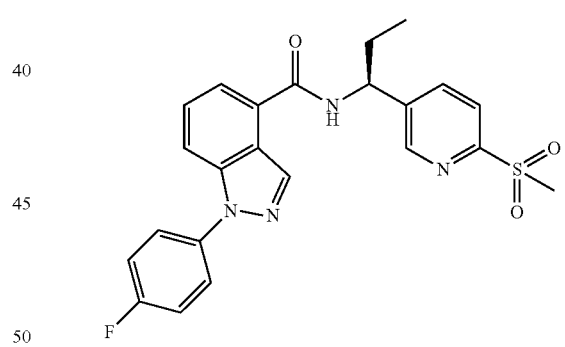
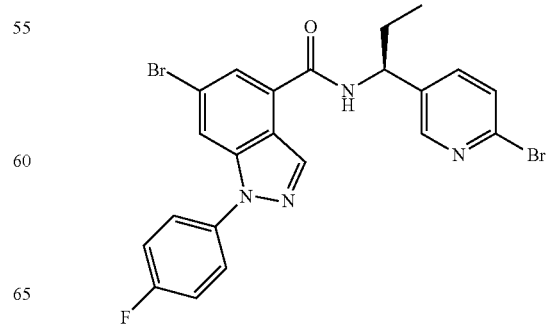

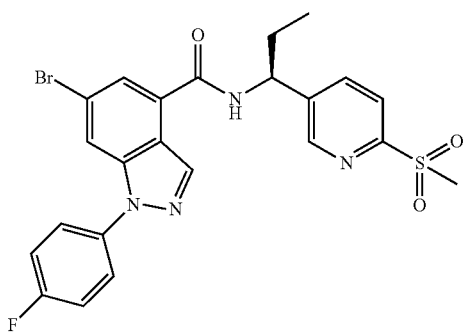
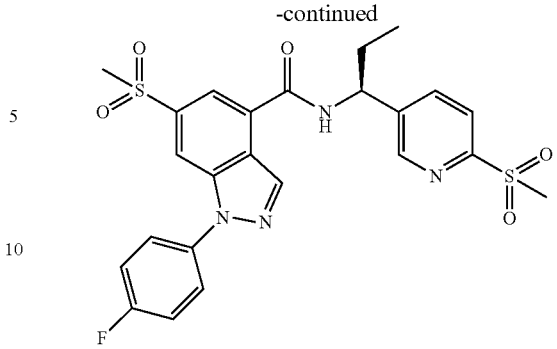
or a pharmaceutically acceptable salt thereof.
7. A pharmaceutical composition comprising a pharmaceutically effective amount of a compound according to claim 1.
* * * * *